(12) United States Patent
Mahley et al.

(10) Patent No.: US 7,964,598 B2
(45) Date of Patent: Jun. 21, 2011

(54) APOE4 DOMAIN INTERACTION INHIBITORS AND METHODS OF USE THEREOF

(75) Inventors: Robert W. Mahley, San Francisco, CA (US); Karl H. Weisgraber, Walnut Creek, CA (US); Yadong Huang, San Francisco, CA (US)

(73) Assignee: The J. David Gladstone Institutes, San Francisco, CA (US)

( * ) Notice: Subject to any disclaimer, the term of this patent is extended or adjusted under 35 U.S.C. 154(b) by 1135 days.

(21) Appl. No.: 11/244,268

(22) Filed: Oct. 4, 2005

(65) Prior Publication Data

US 2006/0073104 A1     Apr. 6, 2006

Related U.S. Application Data

(63) Continuation-in-part of application No. 09/782,757, filed on Feb. 12, 2001, now abandoned, which is a continuation-in-part of application No. 09/070,675, filed on Apr. 30, 1998, now abandoned, which is a continuation-in-part of application No. 08/659,785, filed on Jan. 19, 1996, now abandoned.

(60) Provisional application No. 60/005,550, filed on Oct. 17, 1995.

(51) Int. Cl.
| | |
|---|---|
| A61K 31/535 | (2006.01) |
| A61K 31/42 | (2006.01) |
| A61K 31/38 | (2006.01) |
| A01N 43/76 | (2006.01) |
| A01N 43/12 | (2006.01) |
| C07D 498/00 | (2006.01) |
| C07D 487/00 | (2006.01) |

(52) U.S. Cl. ............ 514/238.8; 514/375; 514/443; 548/218; 548/302.1

(58) Field of Classification Search ........... 514/235.8, 514/375, 443; 548/218, 302.1
See application file for complete search history.

(56) References Cited

U.S. PATENT DOCUMENTS

| | | | |
|---|---|---|---|
| 4,582,779 A * | 4/1986 | Kubota et al. ............. | 430/409 |
| 4,983,586 A | 1/1991 | Bodor | |
| 5,002,935 A | 3/1991 | Bodor | |
| 5,017,566 A | 5/1991 | Bodor | |
| 5,153,179 A | 10/1992 | Eibl | |
| 2002/0009439 A1 | 1/2002 | Mahley et al. | |
| 2004/0223916 A1 | 11/2004 | Burt et al. | |

FOREIGN PATENT DOCUMENTS

| | | | |
|---|---|---|---|
| GB | 1079075 | * | 8/1967 |
| JP | 08-292183 A | | 11/1996 |
| JP | 11-242026 A | | 9/1999 |
| WO | WO 94/13798 | | 6/1994 |
| WO | WO 95/06456 | | 3/1995 |
| WO | WO 95/06470 | | 3/1995 |
| WO | WO 97/14437 A1 | | 4/1997 |

OTHER PUBLICATIONS

"Sigma Catalog" 2000, Sigma Chemical Company, p. 145, col. 1. XP002278833.
Elokdah et al. Design, Synthesis, and Biological Evaluation of Thio-Containing Compounds with Serum HDL-Cholesterol-Elevating Properties. (2004) J. Med.Chem., 47, 681-695.
Alberts, Mark J., et al., (1995) "ApoE Genotype and Survival from Intracerebral Haemorrhage", The Lancet 346:575.
Beffert, U., et al., (1995) "Apolipoprotein E Uptake is Increased in the Presence of Beta Amyloid Peptides and Reduced by Blockade of the Low Density Lipoprotein Receptor", Society for Nueroscience 21:6.
Baba et al. (1991) "Intracarotid infusion of leukotriene C4 selectively increases blood-brain barrier permeability after focal ischemia in rats." J. Cereb. Blood Flow Metab., vol. 11:638-643.
Battey et al. (1994) "The 39-kDa receptor-associated protein regulates ligand binding by the very low density lipoprotein receptor." J. Biol. Chem., vol. 269:23268-23273.
Bellosta et al. (1995) "Stable expression and secretion of apolipoproteins E3 and E4 in mouse neuroblastoma cells produces differential effects of neurite outgrowth." J. Biol. Chem., vol. 270:27063-27071.
Bickel et al. (1993) "Pharmacologic effects in vivo in brain by vector-mediated peptide drug delivery." Proc. Natl. Acad. Sci. USA, vol. 90:2618-2622.
Bilheimer et al. (1972) "The metabolism of very low density lipoproteins I. Preliminary in vitro and in vivo observations." Biochem. Biophys. Acta., vol. 260:212-221.
Borth (1992) "$\alpha_2$-macroglobulin, a multifunctional binding protein with targeting characteristics." Faseb J., vol. 6:3345-3353.
Bottenstein et al. (1980) "Fibronectin and polylysine requirement for proliferation of neuroblastoma cells in defined medium." Exp. Cell Res., vol. 129:361-366.
Boyles et al. (1985) "Apolipoprotein E associated with astrocytic glia of the central nervous system and with nonmyelinating glia of the peripheral nervous system." J. Clin. Invest., vol. 76:1501-1513.
Boyles et al. (1989) "A role for apolipoprotein E, apolipoprotein A-1, and low density lipoprotein receptors in cholesterol transport." J. Clin. Invest., vol. 83:1015-1031.
Chappell et al. (1993) "Lipoprotein lipase induces catabolism of normal triglyceride-rich lipoproteins via the low density lipoprotein receptor-related protein/$\alpha_2$-macroglobulin recentor in vitro " J Biol. Chem., vol. 268:14168-14175.
Chen et al. (1988) "Calcium phosphate-mediated gene transfer: A highly efficient transfection system for stably transforming cells with plasmid DNA." Bio Techniques, vol. 6:632-638.

(Continued)

Primary Examiner — Sreeni Padmanabhan
Assistant Examiner — Kendra D Carter
(74) Attorney, Agent, or Firm — Paula A. Borden; Bozicevic, Field & Francis LLP

(57) ABSTRACT

The present invention provides compounds that inhibit apoE4 domain interaction; and compositions, including pharmaceutical compositions, comprising the compounds. The present invention provides methods of treating apoE4-related disorders. The methods generally involve administering to an individual in need thereof a therapeutically effective amount of an apoE4 domain interaction inhibitor.

5 Claims, 33 Drawing Sheets

OTHER PUBLICATIONS

Corder et al. (1993) "Gene dose of apolipoprotein E type 4 allele and the risk of Alzheimer's disease in late onset families." *Science*, vol. 261:921-923.

Crowther (1993) "Tau protein and paired helical filaments of Alzheimer's disease." *Curr. Opin. Struct. Biol.*, vol. 3:202-206.

Dong et al. (1994) "Human apolipoprotein E. Role of arginine 61 in mediating the lipoprotein preferences of the E3 and E4 isoforms." *J. Biol. Chem.*, vol. 269:22358-22365.

Dong et al. (1995) "Apolipdprotein E4 preference for very low density lipoproteins results from domain interaction mediated by glutamic acid-255 and arginine-61." *Circulation*, vol. 92:I-427-I-428.

Elshourbagy et al. (1985) "Apolipoprotein E mRNA is abundant in the brain and adrenals, as well as in the liver, and is present in other peripheral tissues of rats and marmosets" *Proc Natl. Acad. Sci. USA.* vol. 82:203-207.

Feskens et al. (1994) "Apolipoprotein e4 allele and cognitive decline in elderly men." *BMJ*, vol. 309:1202-1206.

Forss-Petter et al. (1990) "Transgenic mice expressing β-galactosidase in mature nerons under neuron-specific enolase promoter control." *Neuron*, vol. 5:187-197.

Gennuso et al. (1993) "Effect of blood-brain barrier and blood-tumor barrier modification on central nervous system iposomal uptake." *Cancer Invest.*, vol. 11:118-128.

Godyna et al. (1995) "Identification of the low density lipoprotein receptor-related protein (LRP) as an endocytic receptor for thrombospondin-1." *J. Cell. Biol.*, vol. 129:1403-1410.

Goldstein et al. (1983) "Receptor-mediated endocytosis of low-density lipoprotein in cultured cells." *Met. Enzymol.*, vol. 98:241-260.

Handelmann et al. (1992) "Effects of apolipoprotein E, β-very low density lipoproteins, and cholesterol on the extension of neuritis by rabbit dorsal root ganglion neurons in vitro." *J. Lipid Res.*, vol. 33:1677-1688.

Helkala et al. (1995) "The association of apolipoprotein E polymorphism with memory: a population based study." *Neurosci. Letts.*, vol. 191:141-144.

Hoeg et al. (1987) "3-hydroxy-3-methylglutaryl-coenzyme A reductase inhibitors in the treatment of hypercholsterolemia." *JAMA*, vol. 258:3532-3536.

Holtzman et al. (1995) "LRP mediates apolipoprotein E-dependent neurite outgrowth in a CNS-derived neuronal cell line." *Soc. Neurosci.*, vol. 21:1009.

Humphries et al. (1989) "Decreasing sulfation of proteoglycans produced by cultured cells." *Met. Enzymol.*, vol. 179:428-434.

Hyman et al. "$\alpha_2$-macroglobulin receptor/low density lipoprotein receptor-related protein." *Annals new York Academy of Sciences*, pp. 88-95, (1994).

Ignatius et al. (1986) "Expression of apolipoprotein E during nerve degeneration and regeneration." *Proc. Natl. Acad. Sci. USA*, vol. 83:1125-1129.

Ignatius et al. (1987) "Lipoprotein uptake by neuronal growth cones in vitro." *Science*, vol. 236:959-962.

Innerarity et al. (1979) "Binding of arginine-rich (E) apoprotein after recombination with phospholipid vesicles to the low density lipoprotein receptors of fibroblasts." *J. Biol. Chem.*, vol. 254:4186-4190.

Innerarity et al. (1983) "The receptor-binding domain of human apolipoprotein E." *J. Biol. Chem.*, vol. 258:12341-12347.

Jackowski, Andres, (1995) "Neural Injury Repair: Hope for the Future as Barriers to Effective CNS Regeneration Become Clearer", *British Journal of Neurosurgery*, 9:303-317.

Ji et al. (1994) "Secretion-capture role for aoplipoprotein E in remnant lipoprotein metabolism involving cell surface heparan sulfate proteoglycans." *J. Biol. Chem.*, vol. 269:2764-2772.

Ji et al. (1994) "Lactoferrin binding to heparan sulfate proteoglycans and the LDL receptor-related protein." *Arterioscler. Thromb.*, vol. 14:2025-2032.

Ji et al. (1994) "Enhanced binding and uptake of remnant lipoproteins by hepatic lipase-secreting hepatoma cells in culture." *J. Biol. Chem.*, vol. 269:13429-13436.

Ji et al. (1993) "Role of heparan sulfate proteoglycans in the binding and uptake of apolipoprotein E-enriched remnant lipoproteins by cultured cells." *J. Biol. Chem.*, vol. 268:10160-10167.

Kostis et al. (1994) "Central nervous system effects of HMG CoA reductase inhibitors: Lovastatin and pravastatin on sleep and cognitive performance in patients with hypercholesterolemia." *J. Clin. Pharmacol.*, vol. 34:989-996.

Kounnas et al. (1992) "The $\alpha_2$-macroglobulin receptor/low density lipoprotein receptor-related protein binds and internalizes pseudomonas exotoxin A" *J. Biol. Chem.*, vol. 267:12420-12423.

Kowal (1989) "Low density lipoprotein receptor-related protein mediates uptake of cholesteryl esters derived from apoprotein E-enriched lipoproteins." *Proc. Natl. Acad. Sci USA*. vol. 86.5810-5814.

Lawn (1982) "Lipoprotein(a) in heart disease." *Scientific American*, pp. 54-60.

Levin (1980) "Relationship of octanol/water partition coefficient and molecular weight in rat brain capillary permeability." *J. Med. Chem.*, vol. 23:682-684.

Lopes et al. (1994) "Expression of $\alpha_2$-macroglobulin receptor/low density lipoprotein receptor-related protein is increased in reactive and neoplastic glial cells." *FEBS Lett.*, vol. 338:301-305.

Ma, J., et al., (1995) "Promotion of the Neurotoxicity of Alzheimer AƎ Protein by the Pathological Chaperones Act and ApoE4: Inhibition by AƎ-Related Peptides and ApoE2" *Society for Neuroscience* 21:1714.

Mahley (1988) "Apolipoprotein E: Cholesterol transport protein with expanding role in cell biology." *Science*, vol. 240:622-630.

Mahley "Apoliprotein E: Structure and function in lipid metabolism and neurobiology." *The Molecular and Genetic Bases of Neurological Disease*, $2^{nd}$ ed., 41 pgs. Total, (2003).

Mahley et al. (1994) "Role of heparan sulfate proteoglycans and the LDL receptor-related protein in remnant lipoprotein metabolism." *Ann. N.Y. Acad. Sci. USA*, vol. 737:39-52.

Mahley et al. (1991) "Chylomicron and chylomicron remnant catabolism." *Curr. Opin. Lipidol.*, vol. 2:170-176.

Mahley et al. (1987) "Canine hyperlipoproteinemia and atherosclerosis." *Am. J. Pathol.*, vol. 87:205-226.

Mahley et al. "Apoliprotein E: Structure, function, and possible roles in modulating neurite extension and cytoskeletal activity." *Research and Perspectives in Alzheimer's Disease*. pp. 1-16, (1996).

McKhann et al. (1984) "Clinical diagnosis of Alzheimer's disease." *Neurol.*, vol. 34:939-944.

Medh et al. (1995) "The 39-kDa receptor-associated protein modulates lipoprotein catabolism by binding to LDL receptors." *J. Biol. Chem.*, vol. 270:536-540.

Meilinger et al. (1995) "Removal of lactoferrin from plasma is mediated by binding to low density lipoprotein receptor-related protein/$\alpha_2$-macroglobulin receptor and transport to endosomes." *FEBS Lett.*, vol. 360:70-74.

Muller et al. (1985) "A specific 37,000-dalton protein that accumulates in regenerating but not in nonregenerating mammalian nerves." *Science*, vol. 228:499-501.

Nathan et al. (1995) "The inhibitory effect of apolipoprotein E4 on neurite outgrowth is associated with microtubule depolymerization." *J. Biol. Chem.*, vol. 270:19791-19799.

Nathan et al. (1994) "Differential effects of apolipoproteins E3 and E4 on neuronal growth in vitro." *Science*, vol. 264:850-852.

Nathan et al. (1994) "The inhibition of neurite outgrowth by apolipoprotein E4 is mediated through the low density lipoprotein receptor-related protein." *Soc. Neurosci*, vol. 20(part 2):1033.

Neuwelt et al. (1994) "Modification of the blood brain barrier in the chemotherapy of malignant brain tumors." *Fed. Proc.*, vol. 43:214-219.

Orlando et al. (1994) "Functional domains of the receptor-associated protein (RAP)." *Proc. Natl Acad. Sci. USA*, vol. 91:3161-3165.

Orth et al. (1994) "Low density lipoprotein receptor-related protein is necessary for the internalization of both issue-type plasminogen activator-inhibitor complexes and free tissue-type plasminogen activator." *J. Biol. Chem.*, vol. 269:21117-21122.

Pardridge (1992) "Recent developments in peptide drug delivery to the brain." *Pharmacol. Toxicol.*, vol. 71:3-10.

Pardridge (1994) "New approaches to drug delivery through the blood-brain barrier." *Tibtech*, vol. 12:239-245.

Petersen et al. (1995) "Apolipoprotein E status as a predictor of the development of Alzheimer's disease in memory-impaired individuals." *JAMA*, vol. 273:1274-1278.

Pitas et al. (1987) "Astrocytes synthesize apolipoprotein E and metabolize apolipoprotein E-containing lipoproteins." *Biochem. Biophys. Acta*, vol. 917:148-161.

Pitas et al. (1987) "Lipoproteins and their receptors in the central nervous system." *J. Biol. Chem.*, vol. 262:14352-14360.

Pitas et al. (1983) "Foam cells in explants of atherosclerotic rabbit aortas have receptors for β-very low density lipoproteins and modified low density lipoproteins." *Arteriosclerosis.* vol. 3.2-12.

Pitas et al. (1981) "Acetoacetylated lipoproteins used to distinguish fibroblasts from macrophages in vitro by fluorescence microscopy." *Arteriosclerosis*, vol. 1:177-185.

Pitas et al. (1980) "Cell surface receptor binding of phospholipid protein complexes containing different ratios of receptor-active and-inactive E apoprotein." *J. Biol. Chem.*, vol. 255:5454-5460.

Pittman et al. (1987) "Synthetic high density lipoprotein particles." *J. Biol. Chem.*, vol. 262:2435-2442.

Prudinger (1976) in Peptide Hormones, ed. J.A. Parsons, University Park Press, Baltimore, pp. 1-7.

Quon et al. (1991) "Formation of β-amyloid protein deposits in brains of transgenic mice." *Nature*, vol. 352:239-241.

Rebeck et al. (1995) "Multiple, diverse senile plaque-associated proteins are ligands of an apolipoprotein E receptor, the $\alpha_2$-macroglobulin receptor-low density-lipoproteinn receptor-related protein." *Annals of Neurology.* vol. 37:211-217.

Reed et al. (1994) "Lower cognitive performance in normal older adult male twins carrying the apolipoprotein E ε4 allele." *Arch. Neurol.*, vol. 51:1189-1192.

Roheim et al. (1979) "Apolipoproteins in human cerebrospinal fluid." *Proc. Natl. Acad. Sci. USA*, vol. 76:4646-4649.

Roses (1994) "The Alzheimer's diseases." *Curr. Neurol.*, vol. 14:111-141.

Rudinger, J., (1976) "Characteristics of the Amino Acids as Components of a Peptide Hormone Sequence", *Peptide Hormones* ed. J.A. Parsons, University Park Press, Baltimore. pp. 1-7.

Sambrook et al. (1989) *Molecular Cloning: A laboratory manual.*, $2^{nd}$ ed., Cold Spring Harbor Laboratory Press, Cold Spring Harbor, N.Y.

Saunders et al. (1993) "Association of apolipoprotein E allele ε4 with late-onset familial and sporadic Alzheimer's disease." *Neurol.*, vol. 43:1467-1472.

Selkoe (1991) "The molecular pathology of Alzheimer's disease." *Neuron*, vol. 6:487-498.

Schneider et al. (1985) "Purification of the LDL receptor." *Met. Enzymol.*, vol. 109:405-417.

Slater et al. (1988) "Mechanism of action and biological profile of HMG CoA reductase inhibitors. A new therapeutic alternative." *Drugs*, vol. 36(3):72-82.

Spooner et al. (1988) "The ionization and distribution behavior of oleic acid in chylomicrons and chylomicron-like mulsion particles and the influence of serum albumin." *J. Biol. Chem.*, vol. 263:1444-1453.

Strickland et al. (1991) "Primary structure of $\alpha_2$-macroglobulin receptor-associated protein." *J. Biol. Chem.*, vol. 266:13364-13369.

Strickland et al. (1995) "LDL receptor-related protein: a multiligand receptor for lipoprotein and proteinase catabolism." *FASEB J.*, vol. 9:890-898.

Strittmatter et al. (1994) "Hypothesis: Microtubule instability and paired helical filament formation in the Alzheimer disease brain are related to apolipoprotein E genotype." *Exp. Neurol.*, vol. 125:163-171.

Tikkanen et al. (1987) "Treatment of familial and non-familial hypercholesterolaemia: a review of HMG-CoA reductase inhibitors and probucol." *Eur. Heart. J.*, vol. 8(E):97-101.

Tuomanen (1993) "Breaching the blood-brain barrier." *Scientific American*, pp. 80-84.

Warshawsky et al. (1993) "Identification of domains on the 39-kDa protein that inhibit the binding of ligands to the low density lipoprotein receptor-related protein." *J. Biol. Chem.*, vol. 268:22046-22054.

Warshawsky et al. (1995) "Sites within the 39-kDa protein important for regulating ligand binding to the low-density lipoprotein receptor-related protein." *Biochem.*, vol. 34:3404-3415.

Warshawsky et al. (1994) "Identification of domains on the 39-kDa protein that inhibit the binding of ligands to the low density lipoprotein receptor-related protein." *Ann. N.Y. Acad. Sci.*, pp. 514-517.

Weisgraber et al. "The role of apolipoprotein E in the nervous system." *Curr. Opin. Lipidol.*, vol. 5:110-116, (1994).

Weisgraber, Karl H., et al., (1994) "Lipoproteins, Neurobiology, and Alzheimer's Disease: Structure and Function of Apolipoprotein E", *Current Opinion in Structural Biology* 4:507-515.

Willnow et al. (1994) "Genetic deficiency in low density lipoprotein receptor-related protein confers cellular resistance to pseudomonas exotoxin A." *J. Cell. Sci.*, vol. 107:719-726.

Willnow et al. (1994) "Molecular dissection of ligand binding sites on the low density lipoprotein receptor-related protein." *J. Biol. Chem.*, vol. 269:15827-15832.

Willnow et al. (1994) "Low density lipoprotein receptor-related protein and gp 330 bind similar ligands, including plasminogen activator-inhibitor complexes and lactoferrin, an inhibitor of chylomicron remnant clearance." *J. Biol. Chem.*, vol. 267:26172-26180.

Willnow et al. (1995) "Functional expression of low density lipoprotein receptor-related protein is controlled by receptor-associated protein in vivo." *Proc. Natl. Acad. Sci.*, vol. 92:4537-4541.

Wittmaack et al. (1995) "Localization and regulation of the human very low density lipoprotein/apolipoprotein-E receptor: Trophoblast expression predicts a role for the receptor in placental lipid transport." *Endocrinol.*, vol. 136:340-348.

Sigma Catalog, Biochemical and Organic Compounds for Research and Diagnostic Clinical Reagents, Sigma Chemical Co., St. Louis, pp. 671,846,920, (2000).

Bellosta, Stefano, et al.: Stable Expression and Secretion of Apolipoproteins E3 and E4 in Mouse Neuroblastoma Cells Produces Differential Effects on Neurite Outgrowth:, Journal of Biological Chemistry, vol. 270, No. 45, 1995 pp. 27063-27071.

Mahley, Robert, et al.: Apolipoprotein E: Impact of Cytoskeletal Stability in Neurons and the Relationship to Alzheimer's Disease, Current Option in Lipidology, vol. 6, No. 2, 1995, pp. 86-91.

Nathan, Britto P, et al.: "The Inhibitory effect of apolipoprotein E4 on Neurite Outgrowth is Associated with Microtubule Depolymerization", Journal of Biological Chemistry, vol. 270, No. 34, 1995, pp. 19791-19799.

Holtzman, David M et al.; "Low Density Lipoprotein Receptor-Related Protein Mediates Apolipoprotein E-dependent Neurite Outgrowth in a Central Nervous System-Derived Neuronal Cell Line", Proceedings of the National Academy of Sciences of the United States, vol. 92, No. 21, 1995, pp. 9480-9484.

Nathan B P, et al.: "The Inhibition of Neurite Outgrowth by Apolipoprotein E4 is Mediated Through the Low Density Lipoprotein Receptor-Related Protein", Society for Neuroscience Abstracts, Society for Neuroscience, U.S. vol. 21, No. 1-3, 1995, p. 1009.

Dong Li-Ming et al.: "Human Apolipoprotein E4 Domain Interaction. Arginine 61 and the Glutamic Acid 255 Interact to Direct the Preference for very low density Lipoproteins", Journal of Biological Chemistry, vol. 271, No. 32, 1996, pp. 19053-19057.

Dong, L. et al. Circulation (Oct. 15, 1995), vol. 92, No. 8, Supp. S. pp. 2040.

"Sigma Catalog", 2000, Sigma Chemical Company, XP02278833. p. 145, col. 1.

Hardman et al. "Goodman & Gilman's The Pharmacological Basis of Therapeutics" ($9^{th}$ ed, 1996) p. 51 and 57-58.

CAS STN Registry: examples of disulfonate compounds, p. 1-4, (Sep. 8, 2005).

Pravabati et al. Journal of Environmental Biology (1988), 9(1), 21-5.

Murakami et al. Archives of Histology and Cytology (1997), 60(3), 265-274.

Hayashi et al. Histochemistry (1986), 85(2), 111-15.

\* cited by examiner

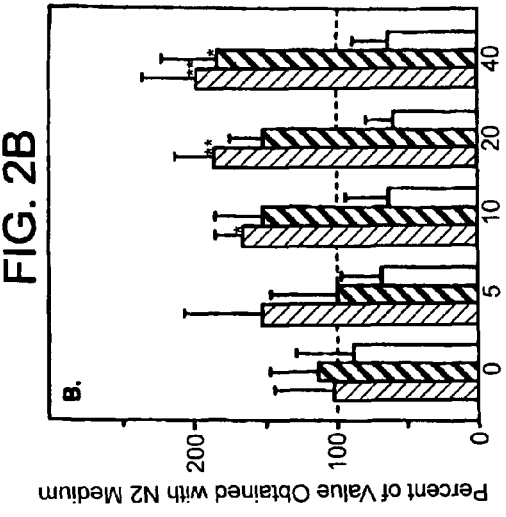
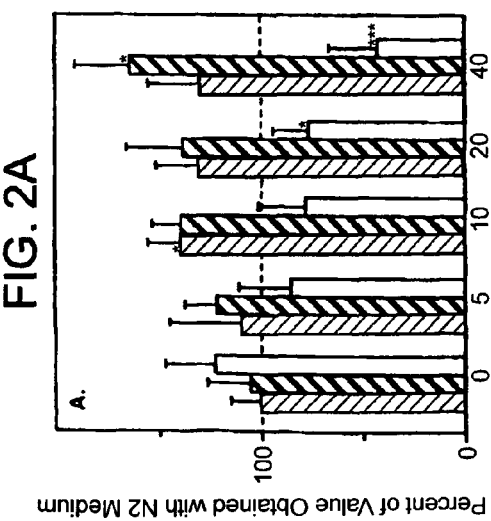
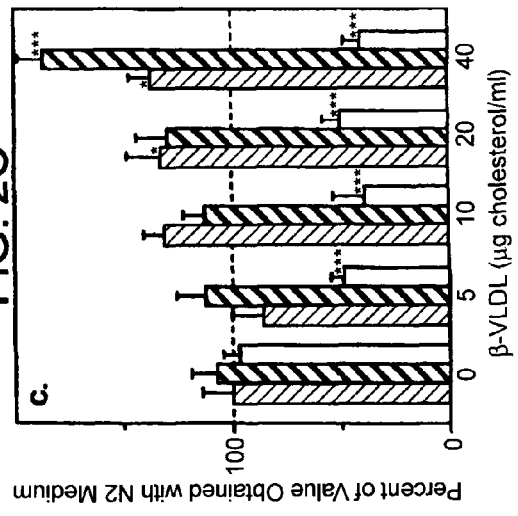

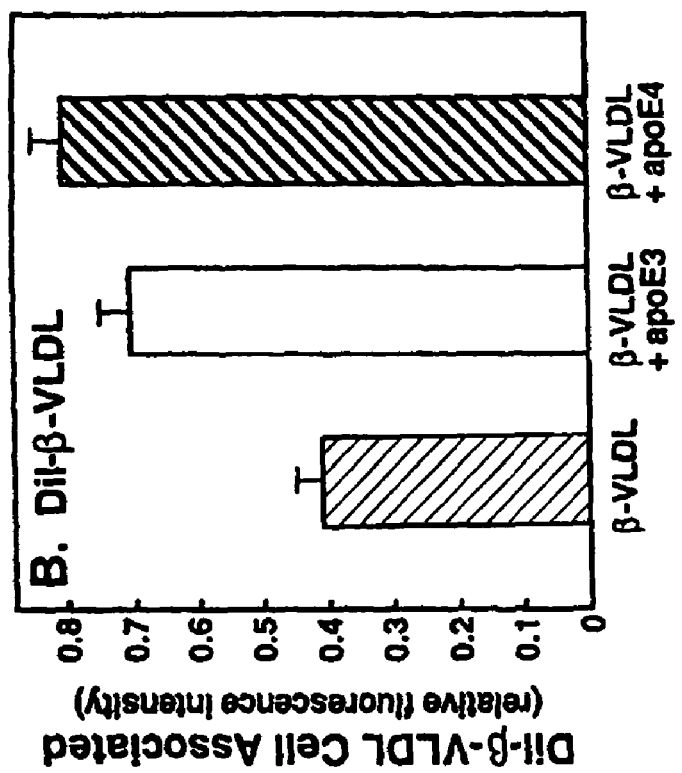
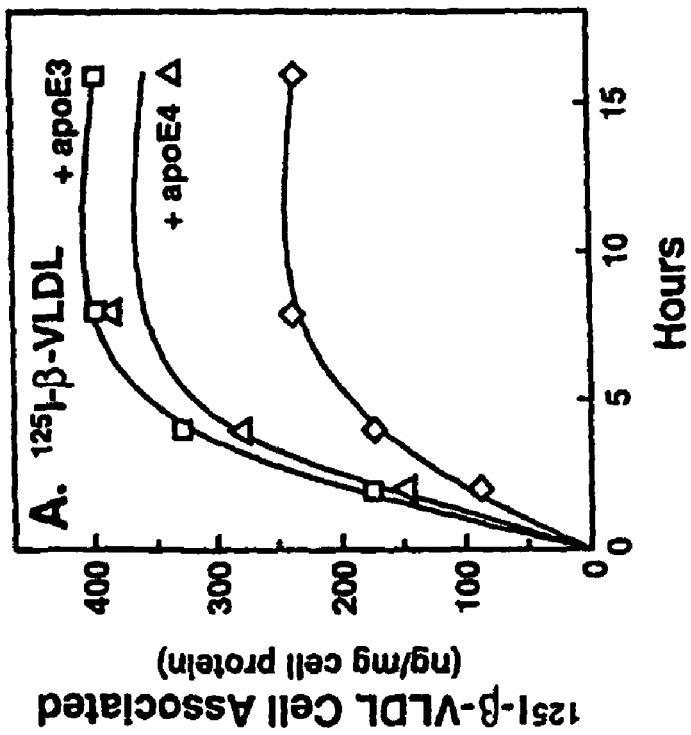

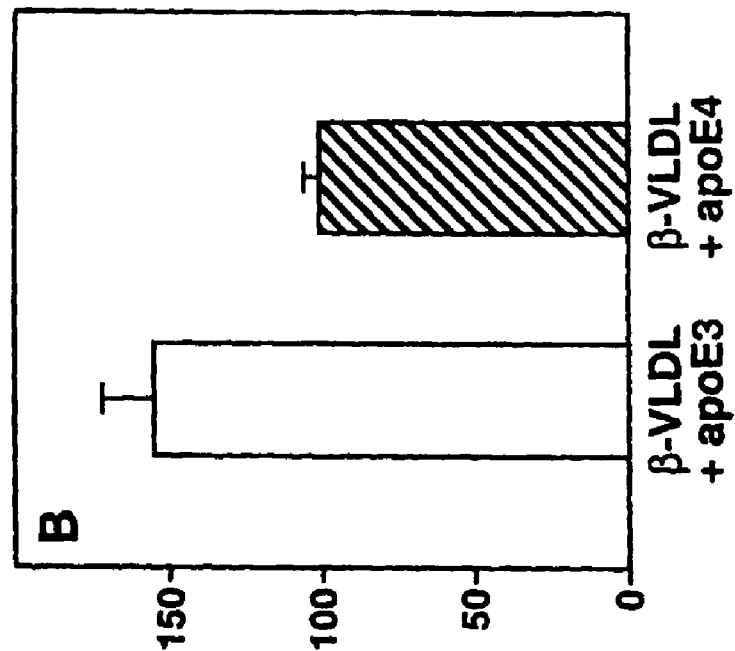
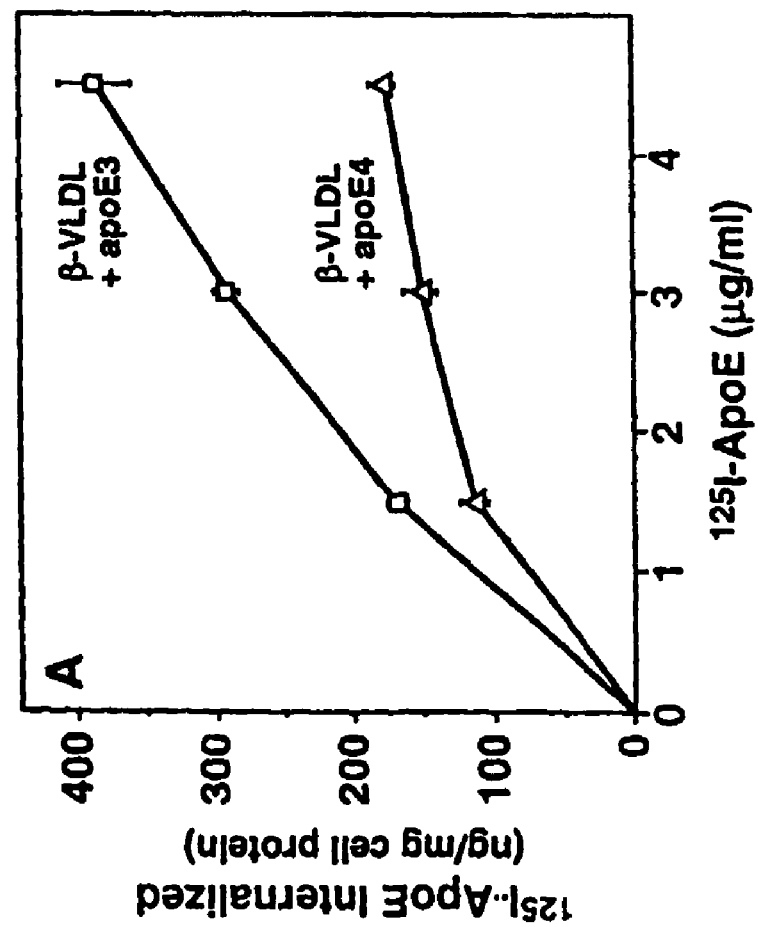
FIG. 13
FIG. 14

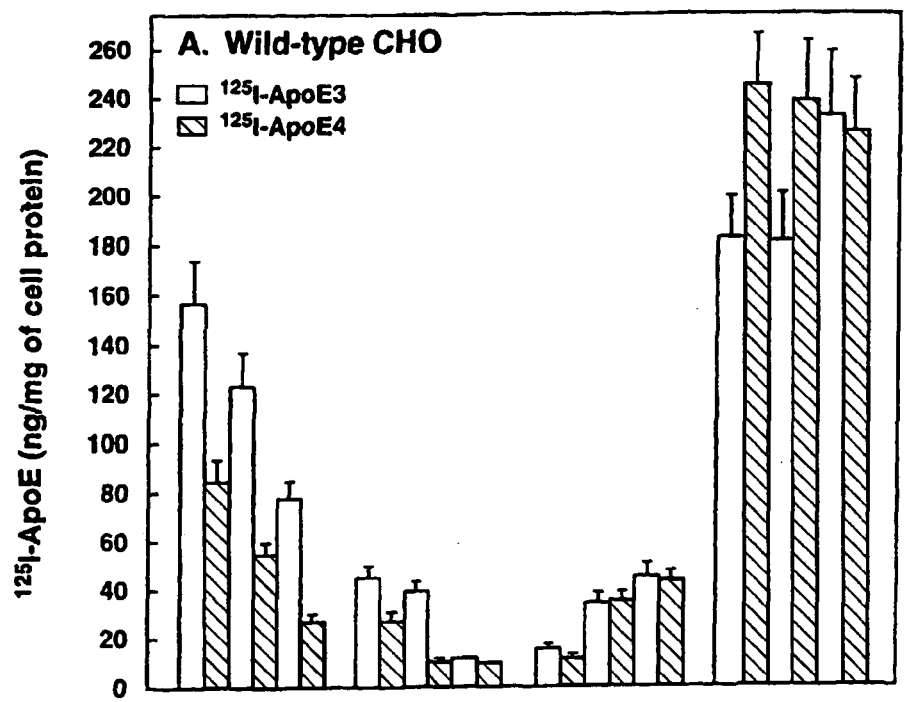
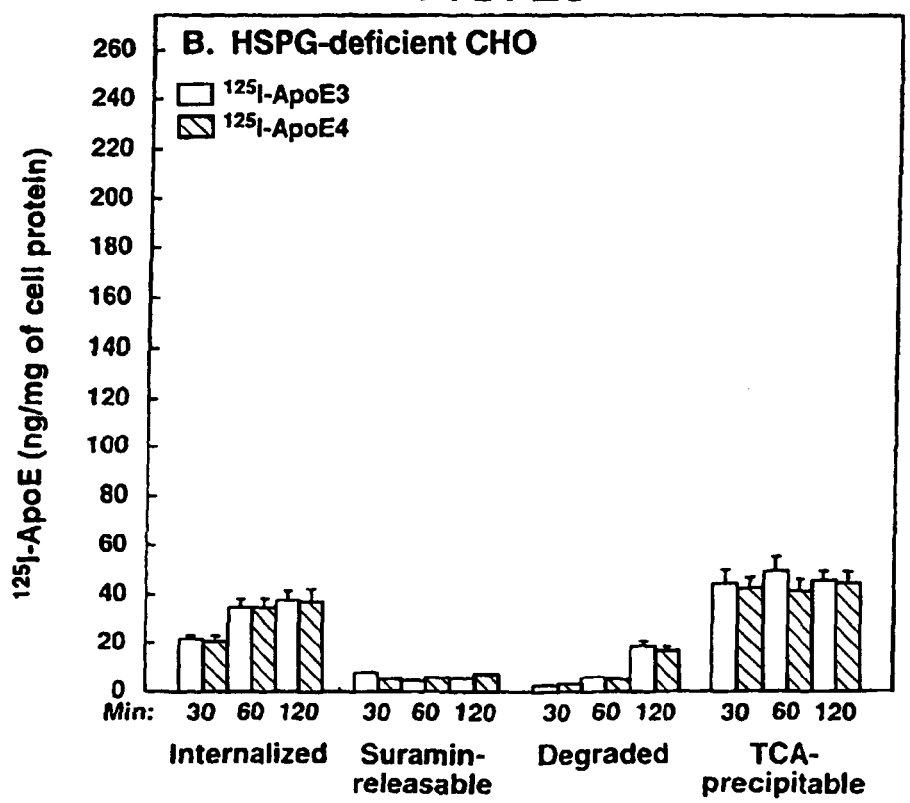

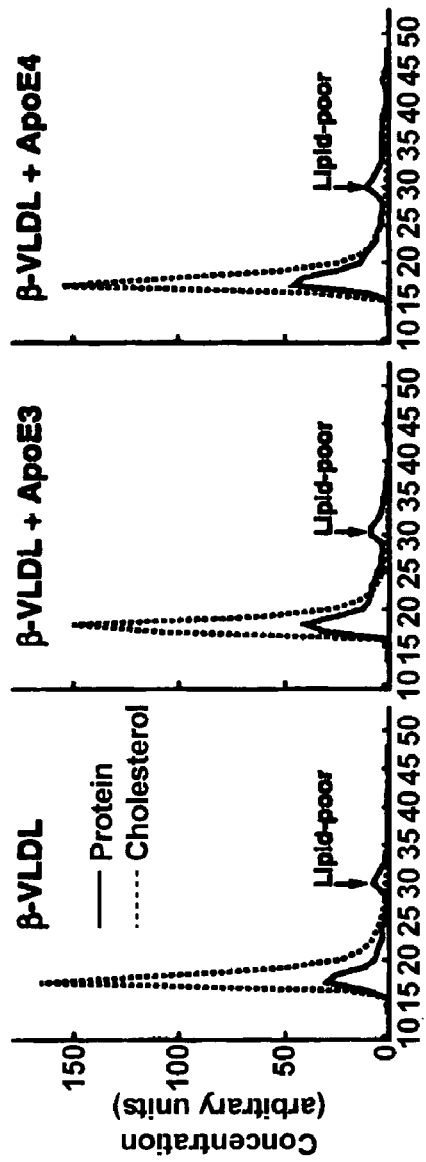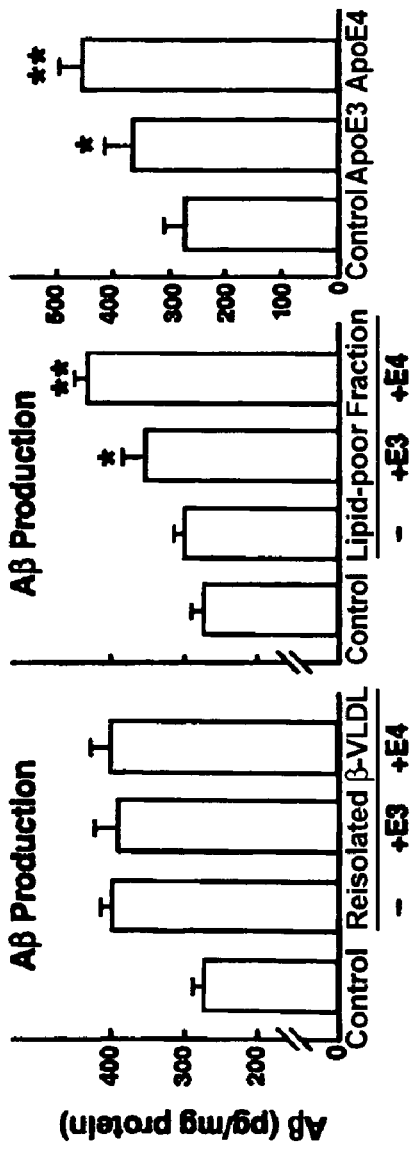
FIG. 21A FIG. 21B FIG. 21C FIG. 21D

FIG. 28
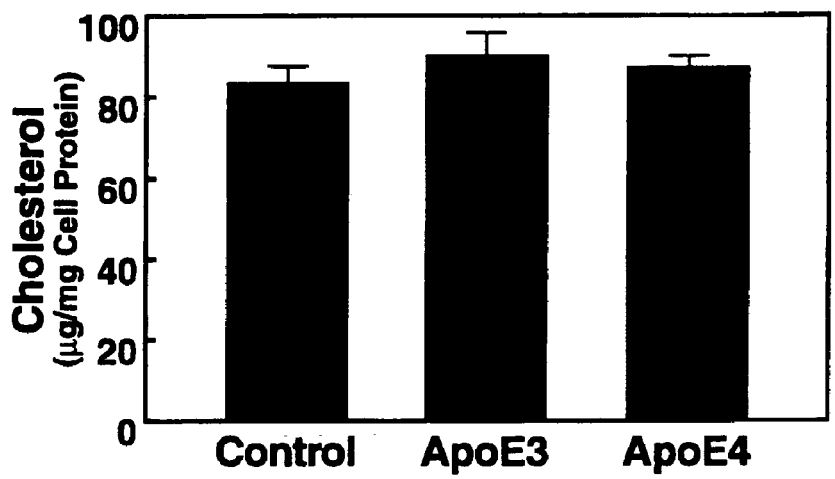
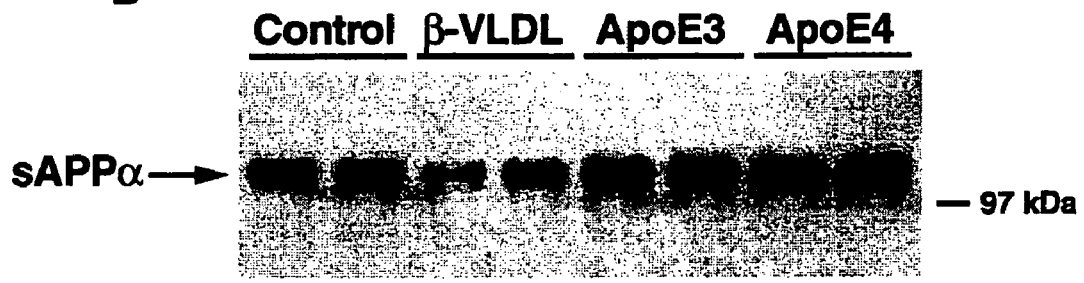
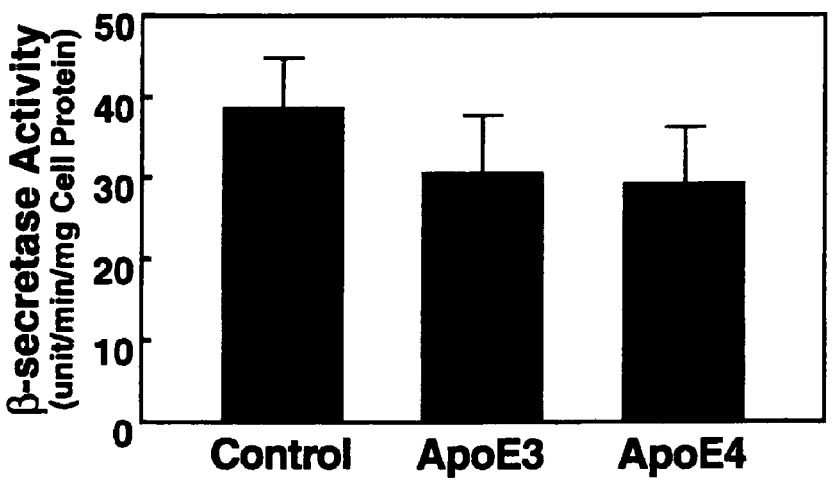

N—| YFP | ApoE3 | CFP |—C    N—| YFP | ApoE4 | CFP |—C

FIG. 29

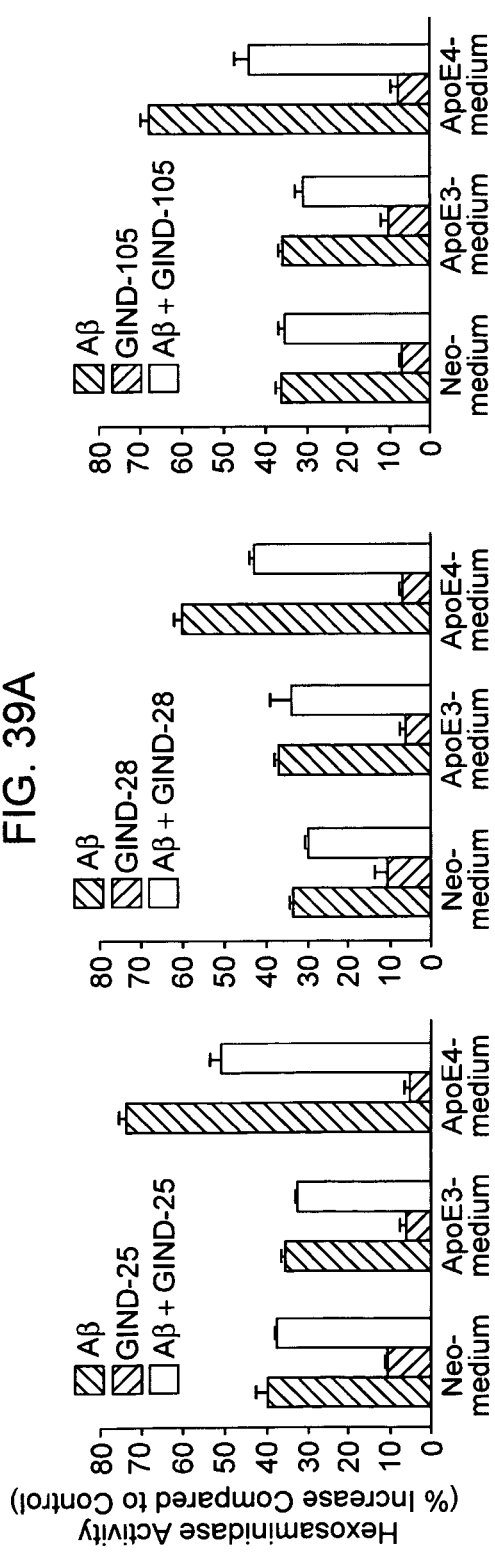
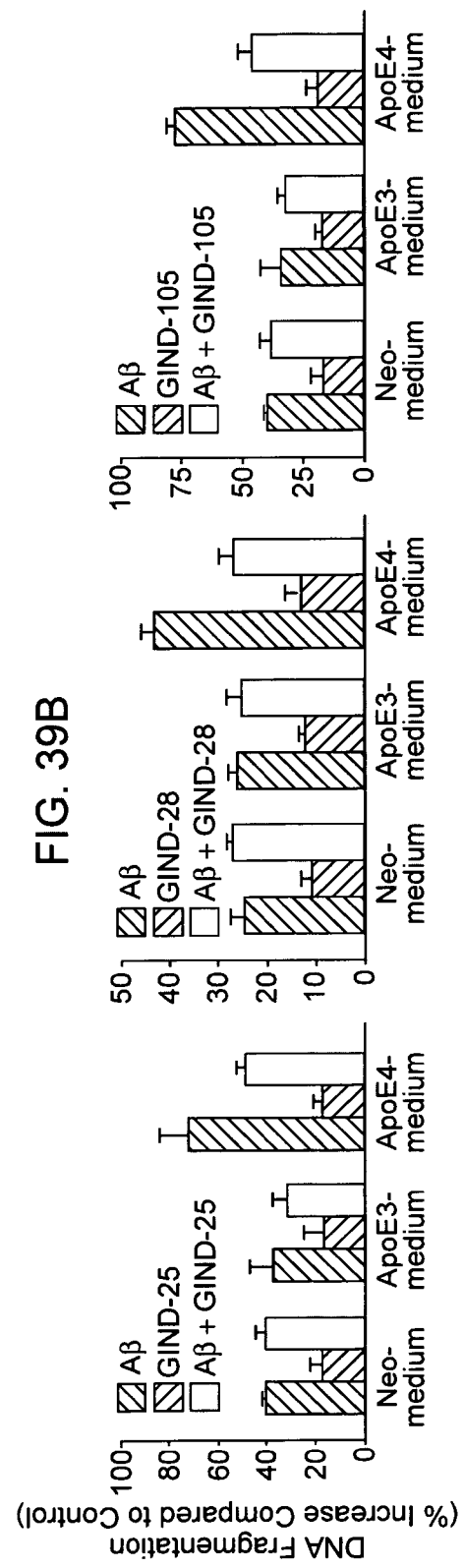
FIG. 39A
FIG. 39B

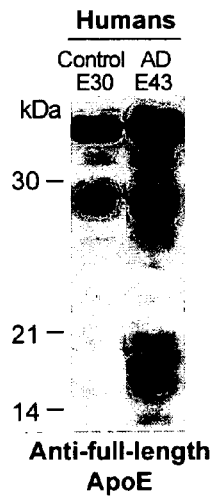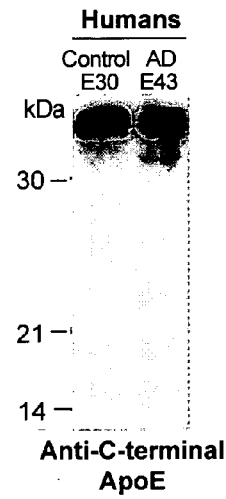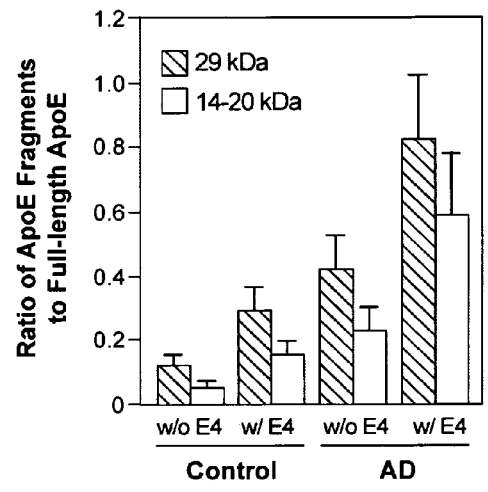
FIG. 40A  FIG. 40B  FIG. 40C
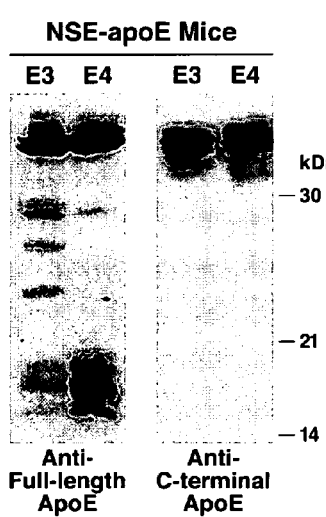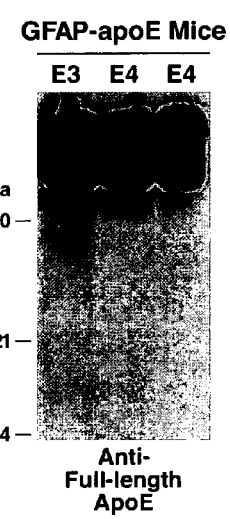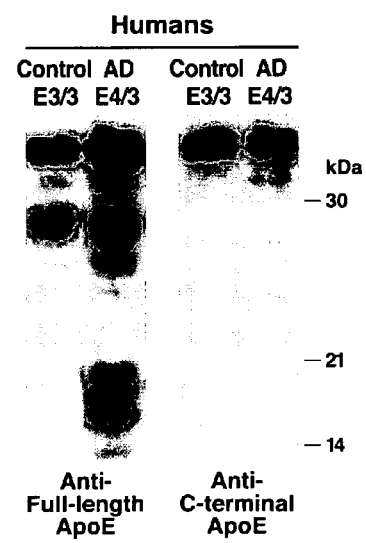
FIG. 41A  FIG. 41B  FIG. 41C

SEQUENCE LISTING

<160> NUMBER OF SEQ ID NOS: 5

<210> SEQ ID NO 1
<211> LENGTH: 9
<212> TYPE: PRT
<213> ORGANISM: Artificial Sequence
<220> FEATURE:
<223> OTHER INFORMATION: Secretase substrate

<400> SEQUENCE: 1

Glu Val Lys Met Asp Ala Glu Phe Lys
 1               5

<210> SEQ ID NO 2
<211> LENGTH: 21
<212> TYPE: RNA
<213> ORGANISM: Artificial Sequence
<220> FEATURE:
<223> OTHER INFORMATION: siRNA

<400> SEQUENCE: 2
uggcaucuca guagacuauu u                                              21

<210> SEQ ID NO 3
<211> LENGTH: 21
<212> TYPE: RNA
<213> ORGANISM: Artificial Sequence
<220> FEATURE:
<223> OTHER INFORMATION: siRNA

<400> SEQUENCE: 3
auagucuacu gagaugccau u                                              21

<210> SEQ ID NO 4
<211> LENGTH: 21
<212> TYPE: RNA
<213> ORGANISM: Artificial Sequence
<220> FEATURE:
<223> OTHER INFORMATION: siRNA

<400> SEQUENCE: 4
uguguacugg accgauucau u                                              21

<210> SEQ ID NO 5
<211> LENGTH: 21
<212> TYPE: RNA
<213> ORGANISM: Artificial Sequence
<220> FEATURE:
<223> OTHER INFORMATION: siRNA

<400> SEQUENCE: 5
ugaaucgguc caguacacau u                                              21

APOE4 DOMAIN INTERACTION INHIBITORS AND METHODS OF USE THEREOF

CROSS-REFERENCE

This application is a continuation-in-part of U.S. patent application Ser. No. 09/782,757, filed Feb. 12, 2001, which is a continuation-in-part of U.S. patent application Ser. No. 09/070,675, filed Apr. 30, 1998, now abandoned, which is a continuation-in-part of U.S. patent application Ser. No. 08/659,785, filed Jan. 19, 1996, now abandoned, which is a continuation-in-part of provisional application Ser. No. 60/005,550, filed Oct. 17, 1995, each of which applications is hereby incorporated in their entirety herein by reference.

STATEMENT REGARDING FEDERALLY SPONSORED RESEARCH

This invention was funded in part with funds from National Institutes of Health Program Project Grant HL41633. The U.S. Government has certain rights to this invention.

FIELD OF THE INVENTION

The present invention relates to compounds that reduce apoE4 domain interaction, and methods of treating disorders related to apoE4.

BACKGROUND OF THE INVENTION

ApoE, a 34,000 molecular weight protein is the product of a single gene on chromosome 19 and exists in three major isoforms designated apoE2, apoE3 and apoE4 for review, see Mahley in: *Molecular and Genetic Bases of Neurological Disease* 2nd ed.; and Mahley (1988) *Science* 240:622-630. The different isoforms result from amino acid substitutions at amino acid residue positions 112 and 158. The common isoform, apoE3, has a cysteine residue at position 112 and an arginine residue at position 158. The apoE4 isoform differs from apoE3 only at position 112, which is an arginine residue. The apoE2 isoform, associated with type III hyperlipoproteinemia (Mahley (1988)), differs from apoE3 only at position 158, which is a cysteine residue. ApoE3 and apoE4 bind normally to the low density lipoprotein (LDL) receptor, whereas apoE2 does not.

ApoE contains two structural domains: an amino-terminal and a carboxy-terminal domain. Weisgraber (1994) *Adv. Protein Chem.* 45:249-302. Each domain is associated with a specific function. The amino terminal domain contains the lipoprotein receptor binding region and the carboxy-terminal domain contains the major lipid-binding elements. The two domains appear to interact with each other in an isoform-specific manner such that amino acid substitutions in one domain influence the function of the other domain, a phenomenon referred to as domain interaction. Domain interaction is responsible for the preference of apoE4 for very low density lipoproteins (VLDL) contrasted with the preference of apoE3 for high density lipoproteins (HDL). The specific amino acid residues in apoE4 that are involved in this interaction have been identified: arginine-61 in the amino-terminal domain and glutamic acid-255 in the carboxy-terminal domain. Dong et al. (1994) *J. Biol. Chem.* 269:22358-22365; and Dong and Weisgraber (1996) *J. Biol. Chem.* 271:19053-19057.

By redistributing lipids among the cells of different organs, apoE plays a critical role in lipid metabolism. While apoE exerts this global transport mechanism in chylomicron and VLDL metabolism, it also functions in the local transport of lipids among cells within a tissue. Cells with excess cholesterol and other lipids may release these substances to apoE-lipid complexes or to HDL containing apoE, which can transport the lipids to cells requiring them for proliferation or repair. The apoE on these lipoprotein particles mediates their interaction and uptake via the LDL receptor or the LRP.

ApoE plays a neurobiological role. ApoE mRNA is abundant in the brain, where it is synthesized and secreted primarily by astrocytes. Elshourbagy et al. (1985) *Proc. Natl. Acad. Sci. USA* 82:203-207; Boyles et al. (1985) *J. Clin. Invest.* 76:1501-1513; and Pitas et al. (1987) *Biochem. Biophys. Acta* 917:148-161. The brain is second only to the liver in the level of apoE mRNA expression. ApoE-containing lipoproteins are found in the cerebrospinal fluid and appear to play a major role in lipid transport in the central nervous system (CNS). Pitas et al. (1987) *J. Biol. Chem.* 262:14352-14360. In fact, the major cerebrospinal fluid lipoprotein is an apoE-containing HDL. ApoE plus a source of lipid promotes marked neurite extension in dorsal root ganglion cells in culture. Handelmann et al. (1992) *J. Lipid Res.* 33:1677-1688. ApoE levels dramatically increase (about 250-fold) after peripheral nerve injury. Müller et al. (1985) *Science* 228:499-501; and Ignatius et al. (1986) *Proc. Natl. Acad. Sci. USA* 83:1125-1129. ApoE appears to participate both in the scavenging of lipids generated after axon degeneration and in the redistribution of these lipids to sprouting neurites for axon regeneration and later to Schwann cells for remyelination of the new axons. Boyles et al. (1989) *J. Clin. Invest.* 83:1015-1031; and Ignatius et al. (1987) *Science* 236:959-962.

Most recently, apoE has been implicated in Alzheimer's disease and cognitive performance. Saunders et al. (1993) *Neurol.* 43:1467-1472; Corder et al. (1993) *Science* 261:921-923; and Reed et al. (1994) *Arch. Neurol.* 51:1189-1192. ApoE4 is associated with the two characteristic neuropathologic lesions of Alzheimer's disease; extracellular neuritic plaques representing deposits of amyloid beta (Aβ) peptide and intracellular neurofibrillary tangles representing filaments of hyperphosphorylated tau, a microtubule-associated protein. For review, see, McKhann et al. (1984) *Neurol.* 34:939-944; Selkoe (1991) *Neuron* 6:487-498; Crowther (1993) *Curr. Opin. Struct. Biol.* 3:202-206; Roses (1994) *Curr. Neurol.* 14:111-141; Weisgraber et al. (1994) *Curr. Opin. Lipidol.* 5:110-116; and Weisgraber et al. (1994) *Curr. Opin. Struct. Biol.* 4:507-515.

Alzheimer's disease is generally divided into three categories: early-onset familial disease (occurring before 60 years of age and linked to genes on chromosomes 21 and 14); late-onset familial disease; and sporadic late-onset disease. Both types of late-onset disease have recently been linked to chromosome 19 at the apoE locus. Other results suggest that apoE4 is directly linked to the severity of the disease in late-onset families. Roses (1994). Recently, cholesterol lowering drugs, the statins, have been suggested for use in treating Alzheimer's disease by lowering apoE4 levels. WO 95/06470.

The neurofibrillary tangles, which are paired helical filaments of hyperphosphorylated tau, accumulate in the cytoplasm of neurons. Tau is a microtubule-associated phosphoprotein which normally participates in microtubule assembly and stabilization; however, hyperphosphorylation impairs its ability to interact with microtubules. Increased binding of tau by apoE has been suggested as a treatment for Alzheimer's disease. WO 95/06456.

In vitro tau interacts with apoE3, but not with apoE4. Strittmatter et al. (1994) *Exp. Neurol.* 125:163-171. The interaction of apoE3 with tau may prevent its hyperphosphorylation, thus allowing it to function normally in stabilizing microtubular structure and function. In the presence of apoE4, tau could become hyperphosphorylated and thus inactive, which could promote the formation of neurofibrillary tangles.

ApoE4 has recently been associated with decreased learning ability and impaired memory. Helkala et al. (1995) *Neurosci. Letts*. 191:141-144. ApoE4 has been found to be a strong predictor of the outcome of patients designated as having memory impairment. Note that, apoE4 has been described as a risk factor, rather than a diagnostic. Peterson et al. (1995) *JAMA* 273:1274-1278; and Feskens et al. (1994) *BMJ* 309:1202-1206.

ApoE interacts with both the LDL receptor and the LRP and undoubtedly with other apoE-binding receptors on neurons. The LRP has been found to be increased after brain injury or glial cell conversion to necplasia. Lopes et al. (1994) *FEBS Lett*. 338:301-305. The LRP was previously identified as the macroglobulin receptor. Strickland et al. (1991) *J. Biol. Chem*. 266:13364-13369; and Borth (1992) *FASEB J*. 6:3345-3353. ApoE does not directly bind to the LRP but must first associate with cell surface heparin sulfate proteoglycans (HSPG). Mahley et al. (1991) *Curr. Opin. Lipidol*. 2:170-176; and Ji et al. (1994) *J. Biol. Chem*. 269:2764-2772. The LRP also binds a number of other ligands, including t-PA, $I_2$-macroglobulin-protease complex, thrombospondin-1, *Pseudomonas* exotoxin A, the receptor associated protein (RAP) and lactoferrin. The LRP ligand binding sites have been at least partially described. Orth et al. (1994) *J. Biol. Chem*. 269:21117-21122; Godyna et al. (1995) *J. Cell. Biol*. 129:1403-1410; Kounnas et al. (1992) *J. Biol. Chem*. 267:12420-12423; Willnow et al. (1994) *J. Cell Sci*. 107:719-726; Meilinger et al. (1995) *FEBS Lett*. 360:70-74; Warshawsky et al. (1993) *J. Biol. Chem*. 268:22046-22054; and Willnow et al. (1994) *J. Biol. Chem*. 269:15827-15832.

It has previously been shown that incubation of dorsal root ganglion neurons in culture with β-VLDL alters the neurite growth of these cells compared to that of cells grown in media alone. Handelmann et al. (1992). In the presence of a source of lipid (β-VLDL or free cholesterol), neurite outgrowth is greatly enhanced, specifically due to extensive branching (with little or no increased neurite extension). When the β-VLDL was enriched with exogenous rabbit apoE (equivalent to human apoE3 with respect to the occurrence of a cysteine residue at position 112) enhanced neurite extension was seen. A lipid source appears to enhance membrane biosynthesis, whereas the addition of excess rabbit apoE with a lipid source results in long neuritic extensions and a trimming back of the branches. It has also been found that the inhibitory effect of apoE4 on neurite outgrowth is associated with microtubule polymerization, whereas apoE3 supports microtubule formation. Nathan et al. (1995) *J. Biol. Chem*. 270:19791-19799.

Neural plasticity, maintenance of existing or formation of new synaptic connections, is critical for normal brain function, including memory. This process can be compromised by various forms of stress, including, but not limited to, age, deposition of plaques and neurofibrillary tangles in Alzheimer's disease and oxygen deprivation. Interference with neuron remodeling can lead to impaired brain function or neurodegeneration of which dementia and Alzheimer's disease are extreme examples. In the case of Alzheimer's disease alone, approximately 4 million individuals are affected in the United States. With the aging of the population, this number is projected to triple in the next twenty years. The present health care cost of Alzheimer's disease is estimated at $90 billion per year in the United States alone. Delaying the average onset of this disease for even ten years would drastically reduce the financial burdens on society and the financial and emotional burdens of the families of these patients.

There are currently no effective therapies for arresting (and, more importantly, reversing) the impairment of central and peripheral nervous system function once an irreversible degenerative cascade begins. Likewise, there is no current therapy for restoration of normal, central and peripheral nervous system function when the induced stress has a less catastrophic or partially reversible effect compared to the dementias.

There is a need in the art for effective therapies for treating disorders associated with apoE4. The present invention addresses this need.

SUMMARY OF THE INVENTION

The present invention provides compounds that inhibit apoE4 domain interaction; and compositions, including pharmaceutical compositions, comprising the compounds. The present invention provides methods of treating apoE4-related disorders. The methods generally involve administering to an individual in need thereof a therapeutically effective amount of an apoE4 domain interaction inhibitor.

Compositions and therapies for the treatment of neurological disorders are disclosed which compositions are identified by an assay which determines the ability of a test compound to affect neuronal remodeling. Specifically, the assay involves cell cultures which are engineered to affect the expression of different isoforms of apolipoprotein such as apoE3 and/or apoE4 in a manner which results in effects on neuronal remodeling, and neurite outgrowth. Apolipoprotein E3-enriched lipoproteins stimulate outgrowth and microtubule stability whereas apoE4-enriched lipoproteins inhibit outgrowth and disrupt microtubules. Because the inhibition of neuronal remodeling and neurite outgrowth are closely associated with certain diseases of the central nervous system, the assay is useful in screening compounds for potential efficacy in treating such diseases. Compounds which stimulate neural outgrowth and microtubule stability are disclosed as are methods of treating diseases of the central nervous system with such compounds. Differential accumulation of apoE3 and apoE4 is mediated primarily by cell-surface heparin sulfate proteoglycans (HSPG). The retention of both apoE3 and apoE4 is reduced and the differential accumulation of apoE3 and apoE4 is eliminated in (1) cells not expressing any proteoglycan and cells specifically not expressing HSPG and in (2) HSPG-expressing cells treated with heparinase.

Results provided here clearly show that apoliproteins and the differential uptake and/or expressions of different isoforms of these proteins affect nerve cell growth and as such play a significant role in neurological diseases. Further, results shown here demonstrate that proteoglycans in general and specifically heparin sulfate proteoglycans effect differential accumulation of apoE3 and apoE4. Thus, those results allow the production of assays which include cell lines specifically engineered to mimic either hindered or enhanced nerve cell growth thereby making it possible to assay compounds for either their potential as therapeutics or their potential harmful effects on nerve cell growth.

The assay systems and transfected cell lines of the invention can be used not only to screen for potential therapeutic compounds for treating neurological disorders but for determining which compounds would be expected to have an adverse affect on nerve cells and as such should be avoided.

The invention further provides compounds that bind to apoE4 and reduce domain interaction without affecting apoE3. Such compounds ("apoE4 domain interaction inhibitors") render apoE4 more "apoE3-like," and are therefore useful for treating disorders associated with apoE4, including neurological disorders, neurodegenerative disorders, and disorders caused by hyperlipidemia, e.g., cardiovascular disorders. The present invention provides compositions, including pharmaceutical compositions, comprising the apoE4 domain interaction inhibitors.

The invention further provides methods of treating disorders related to apoE4. In some embodiments, the methods comprise administering a compound that reduces apoE4 domain interaction. Disorders related to apoE4 include neurological disorders and cardiovascular disorders.

An object of the invention is to provide compounds, compositions and methods of using such in the treatment of neurological disease.

Another object of the invention is to provide an assay for testing compounds for their ability to effect neurite outgrowth.

Another object of the invention is to provide an assay for compounds as well as compounds and compositions which affect the differential cellular accumulation of apoE3 and apoE4.

Another object is to provide an assay for compounds as well as compounds and compositions which affect cell-surface HSPG.

Another object is to provide an assay for compounds as well as compounds and compositions which affect the internalization and accumulation of apoE in cells.

A specific object is to provide a cell culture wherein the cells have been genetically engineered with regard to their expression of an apoE protein and to use the cell culture in a screening assay.

An advantage of the invention is that the cell cultures provide a clear indication of the effect of a compound on neurite outgrowth.

Another advantage of the invention is that it can be used to determine which compounds are potentially harmful due to their inhibition of neurite outgrowth and which compounds are potentially therapeutic due to their enhancement of neurite outgrowth.

A feature of the invention is that genes expressing the different isoforms of apoE protein can be individually affected.

The invention also includes methods of identifying compounds that are effective in interfering with the apoE4 domain interaction. These methods are exemplified by the plasma distribution assay comprising the steps of adding a tracer dose of $^{125}$I-labeled apoE to plasma, separating the various plasma lipoprotein fractions by gel filtration and determining the distribution of $^{125}$I-label among lipoprotein classes. See, e.g. Dong et al. (1994) *J. Biol. Chem.* 269:22358-22365.

These and other objects, advantages, and features of the invention will become apparent to those skilled in the art upon reading this disclosure along with the attached figures.

BRIEF DESCRIPTION OF THE DRAWINGS

FIG. 2 includes 2A, 2B and 2C which are a series of bar graphs depicting the effect of β-VLDL on the number of neurites per cell (A), neurite branching (B), and neurite extension (C) from control Neuro-2a cells and from cells stably transfected to express apoE3 or apoE4. In each case, the solid black bars represent the control, the striped bars represent apoE3 expressing cells and the solid white bars represent apoE4 expressing cells. In all cases the X-axis represents β-VLDL (Tg cholesterol/ml).

FIG. 5 is a graph of the amount of $^{125}$I-β-VLDL associated with the particular cells of the invention as graphed over time in hours.

FIG. 6 is a bar graph of the relative fluorescence intensity of the DiI-β-VLDL associated with cells for three different types of cells as labeled.

FIG. 13 is a graph of the amount of $^{125}$I-ApoE internalized by two different types of cells relative to the concentration of $^{125}$I-ApoE added to the cell culture.

FIG. 14 is a bar graph of the total amount of $^{125}$I-ApoE internalized by the two different types of cells tested.

FIG. 19 is a bar graph of the amount of $^{125}$I-ApoE in ng/mg of cell protein for the different types of CHO cells as labeled.

FIG. 20 is a bar graph of the amount of $^{125}$I-ApoE in Ng/mg of cell protein for the different types of HSPG-deficient CHO cells as labeled.

FIGS. 21A-D depict the effect of β-VLDL; β-VLDL in combination with apoE4 or apoE3; apoE3; and apoE4 on production of Aβ by B103/APP cells.

FIGS. 28A-C depict the effect of apoE3 and apoE4 on cellular cholesterol content, sAPPα level, and β-secretase activity.

FIG. 29 is a schematic representation of the constructs YFP-apoE3-CFP and YFP-apoE4-CFP.

FIGS. 39A and 39B depict the effect of small molecule inhibitors of apoE4 domain interaction on apoE4 potentiation of Aβ-induced apoptosis.

FIGS. 40A-C depict isoform-specific fragmentation of apoE in human brains.

FIGS. 41A-C depict apoE fragmentation in brains of NSE-apoE or GFAP-apoE mice and in brains of humans.

DEFINITIONS

Figure 1:
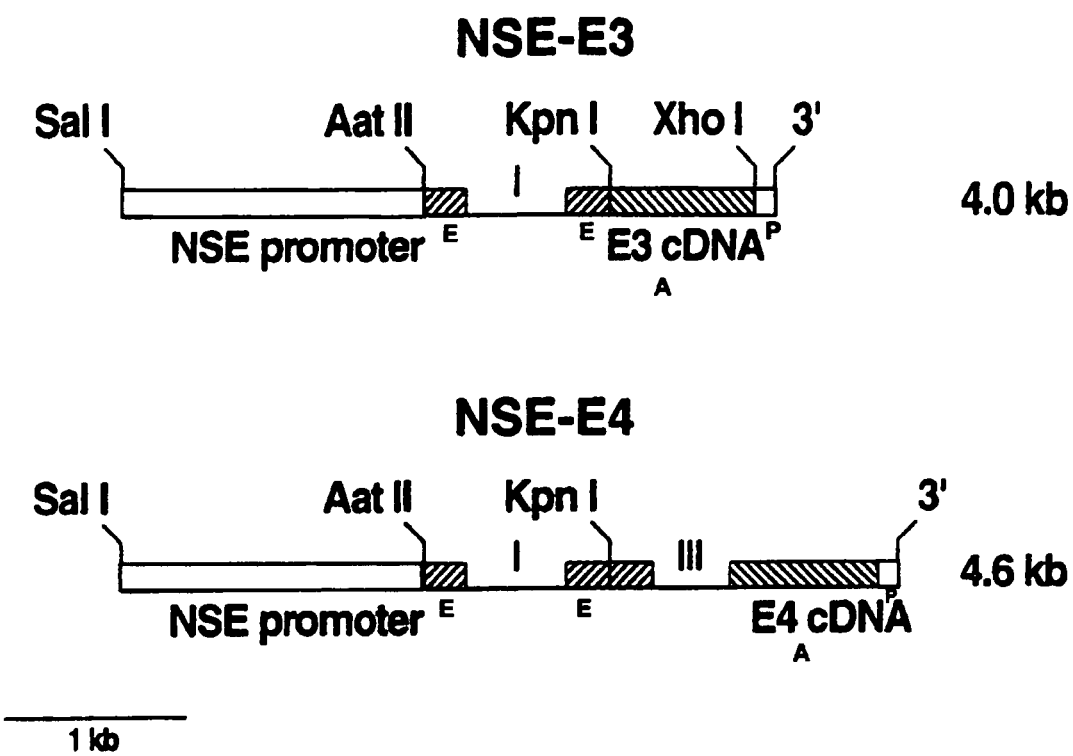
FIG. 1 is a schematic representation of the human apoE cDNA constructs used to transfect the Neuro-2a cells. NSE promoter (N), exons of apoE have "E" underneath, the polylinker region has "P" underneath and apoE cDNA has "A" underneath.

The following abbreviations are used in this application: apoE3, apolipoprotein 3; apoE4, apolipoprotein 4; CHO, Chinese hamster ovary; DiI, 1,1'-dioctadecyl-3,3,3',3'-tetramethylindocarbocyanine; DMEM, Dulbecco's modified Eagle's medium; FBS, fetal bovine serum; FGF, fibroblast growth factor; GPI, glycerophophatidylinositol; HSPG, heparin sulfate proteoglycans; LDL, low density lipoproteins; LRP, LDL receptor-related protein; PBS, phosphate-buffered saline; SDS-PAGE, sodium dodecyl sulfate-polyacrylamide gel electrophoresis; TCA, trichloroacetic acid; and VLDL, very low density lipoproteins.

As used herein, an "apoE4-associated disorder" is any disorder that is caused by the presence of apoE4 in a cell, in the serum, in the interstitial fluid, in the cerebrospinal fluid, or in any other bodily fluid of an individual; any physiological process or metabolic event that is influenced by apoE4 domain interaction; any disorder that is characterized by the presence of apoE4; a symptom of a disorder that is caused by the presence of apoE4 in a cell or in a bodily fluid; a phenomenon associated with a disorder caused by the presence in a cell or in a bodily fluid of apoE4; and the sequelae of any disorder that is caused by the presence of apoE4. ApoE4-associated disorders include apoE4-associated neurological disorders and disorders related to high serum lipid levels. ApoE4-associated neurological disorders include, but are not limited to, sporadic Alzheimer's disease; familial Alzheimer's disease; poor outcome following a stroke; poor outcome following traumatic head injury; and cerebral ischemia. Phenomena associated with apoE4-associated neurological disorders include, but are not limited to, neurofibrillary tangles; amyloid deposits; memory loss; and a reduction in cognitive function. ApoE4-related disorders associated with high serum lipid levels include, but are not limited to, atherosclerosis, and coronary artery disease. Phenomena associated with such apoE4-associated disorders include high serum cholesterol levels.

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse affect attributable to the disease. "Treatment", as used herein, covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease.

The terms "individual," "subject," and "patient," used interchangeably herein, refer to a mammal, including, but not limited to, murines, simians, humans, mammalian farm animals, mammalian sport animals, and mammalian pets.

The term "isolated compound" means a compound which has been substantially separated from, or enriched relative to, other compounds with which it occurs in nature. Isolated compounds are typically at least about 80%, at least about 90% pure, at least about 98% pure, at least about 99%, or greater than 99%, pure, by weight. The present invention relating to active compounds is meant to comprehend diastereomers as well as their racemic and resolved, enantiomerically pure forms and pharmaceutically acceptable salts thereof.

A "therapeutically effective amount" or "efficacious amount" means the amount of a compound that, when administered to a mammal or other subject for treating a disease, is sufficient to effect such treatment for the disease. The "therapeutically effective amount" will vary depending on the compound, the disease and its severity and the age, weight, etc., of the subject to be treated.

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the active agents of the present invention depend on the particular compound (e.g., compound of any one of Formulas I-X) employed and the effect to be achieved, and the pharmacodynamics associated with each compound in the host.

A "pharmaceutically acceptable excipient," "pharmaceutically acceptable diluent," "pharmaceutically acceptable carrier," and "pharmaceutically acceptable adjuvant" means an excipient, diluent, carrier, and adjuvant that are useful in preparing a pharmaceutical composition that are generally safe, non-toxic and neither biologically nor otherwise-undesirable, and include an excipient, diluent, carrier, and adjuvant that are acceptable for veterinary use as well as human pharmaceutical use. "A pharmaceutically acceptable excipient, diluent, carrier and adjuvant" as used in the specification and claims includes both one and more than one such excipient, diluent, carrier, and adjuvant.

As used herein, a "pharmaceutical composition" is meant to encompass a composition suitable for administration to a subject, such as a mammal, especially a human. In general a "pharmaceutical composition" is sterile, and generally free of contaminants that are capable of eliciting an undesirable response within the subject (e.g., the compound(s) in the pharmaceutical composition is pharmaceutical grade). Pharmaceutical compositions can be designed for administration to subjects or patients in need thereof via a number of different routes of administration including oral, buccal, rectal, parenteral, intraperitoneal, intradermal, intracheal and the like. In some embodiments the composition is suitable for administration by an oral route of administration. In some embodiments the composition is suitable for administration by an inhalation route of administration. In some embodiments the composition is suitable for administration by a transdermal route, e.g., using a penetration enhancer. In other embodiments, the pharmaceutical compositions are suitable for administration by a route other than transdermal administration.

As used herein, "pharmaceutically acceptable derivatives" of a compound of the invention include salts, esters, enol ethers, enol esters, acetals, ketals, orthoesters, hemiacetals, hemiketals, acids, bases, solvates, hydrates or prodrugs thereof. Such derivatives may be readily prepared by those of skill in this art using known methods for such derivatization. The compounds produced may be administered to animals or humans without substantial toxic effects and either are pharmaceutically active or are prodrugs.

A "pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

A "pharmaceutically acceptable ester" of a compound of the invention means an ester that is pharmaceutically acceptable and that possesses the desired pharmacological activity of the parent compound, and includes, but is not limited to, alkyl, alkenyl, alkynyl, aryl, heteroaryl, aralkyl, heteroaralkyl, cycloalkyl and heterocyclyl esters of acidic groups, including, but not limited to, carboxylic acids, phosphoric acids, phosphinic acids, sulfonic acids, sulfinic acids and boronic acids.

A "pharmaceutically acceptable enol ether" of a compound of the invention means an enol ether that is pharmaceutically acceptable and that possesses the desired pharmacological activity of the parent compound, and includes, but is not limited to, derivatives of formula $C=C(OR)$ where R is hydrogen, alkyl, alkenyl, alkynyl, aryl, heteroaryl, aralkyl, heteroaralkyl, cycloalkyl or heterocyclyl.

A "pharmaceutically acceptable enol ester" of a compound of the invention means an enol ester that is pharmaceutically acceptable and that possesses the desired pharmacological activity of the parent compound, and includes, but is not limited to, derivatives of formula $C=C(OC(O)R)$ where R is hydrogen, alkyl, alkenyl, alkynyl, aryl, heteroaryl, aralkyl, heteroaralkyl, cycloalkyl or heterocyclyl.

A "pharmaceutically acceptable solvate or hydrate" of a compound of the invention means a solvate or hydrate complex that is pharmaceutically acceptable and that possesses the desired pharmacological activity of the parent compound, and includes, but is not limited to, complexes of a compound of the invention with one or more solvent or water molecules, or 1 to about 100, or 1 to about 10, or one to about 2, 3 or 4, solvent or water molecules.

"Pro-drugs" means any compound that releases an active parent drug according to formulas (I-X) in vivo when such prodrug is administered to a mammalian subject. Prodrugs of a compound of formula (I-X) are prepared by modifying functional groups present in the compound of formula (I-X) in such a way that the modifications may be cleaved in vivo to release the parent compound. Prodrugs include compounds of formulas (I-X) wherein a hydroxy, amino, orsulfhydryl group in any of compounds (I-X) is bonded to any group that may be cleaved in vivo to regenerate the free hydroxyl, amino, or sulfhydryl group, respectively. Examples of prodrugs include, but are not limited to esters (e.g., acetate, formate, and benzoate derivatives), carbamates (e.g., N,N-dimethylaminocarbonyl) of hydroxy functional groups in compounds of any of formulas (I-X), and the like.

The term "organic group" and "organic radical" as used herein means any carbon-containing group, including hydrocarbon groups that are classified as an aliphatic group, cyclic group, aromatic group, functionalized derivatives thereof and/or various combinations thereof. The term "aliphatic group" means a saturated or unsaturated linear or branched hydrocarbon group and encompasses alkyl, alkenyl, and alkynyl groups, for example. The term "alkyl group" means a substituted or unsubstituted, saturated linear or branched hydrocarbon group or chain (e.g., $C_1$ to $C_8$) including, for example, methyl, ethyl, isopropyl, tert-butyl, heptyl, iso-propyl, n-octyl, dodecyl, octadecyl, amyl, 2-ethylhexyl, and the like. Suitable substituents include carboxy, protected carboxy, amino, protected amino, halo, hydroxy, protected hydroxy, nitro, cyano, monosubstituted amino, protected monosubstituted amino, disubstituted amino, $C_1$ to $C_7$ alkoxy, $C_1$ to $C_7$ acyl, $C_1$ to $C_7$ acyloxy, and the like. The term "substituted alkyl" means the above defined alkyl group substituted from one to three times by a hydroxy, protected hydroxy, amino, protected amino, cyano, halo, triflorom-ethyl, mono-substituted amino, di-substituted amino, lower alkoxy, lower alkylthio, carboxy, protected carboxy, or a carboxy, amino, and/or hydroxy salt. As used in conjunction with the substituents for the heteroaryl rings, the terms "substituted (cycloalkyl)alkyl" and "substituted cycloalkyl" are as defined below substituted with the same groups as listed for a "substituted alkyl" group. The term "alkenyl group" means an unsaturated, linear or branched hydrocarbon group with one or more carbon-carbon double bonds, such as a vinyl group. The term "alkynyl group" means an unsaturated, linear or branched hydrocarbon group with one or more carbon-carbon triple bonds. The term "cyclic group" means a closed ring hydrocarbon group that is classified as an alicyclic group, aromatic group, or heterocyclic group. The term "alicyclic group" means a cyclic hydrocarbon group having properties resembling those of aliphatic groups. The term "aromatic group" or "aryl group" means a mono- or polycyclic aromatic hydrocarbon group, and may include one or more heteroatoms, and which are further defined below. The term "heterocyclic group" means a closed ring hydrocarbon in which one or more of the atoms in the ring are an element other than carbon (e.g., nitrogen, oxygen, sulfur, etc.), and are further defined below.

"Organic groups" may be functionalized or otherwise comprise additional functionalities associated with the organic group, such as carboxyl, amino, hydroxyl, and the like, which may be protected or unprotected. For example, the phrase "alkyl group" is intended to include not only pure open chain saturated hydrocarbon alkyl substituents, such as methyl, ethyl, propyl, t-butyl, and the like, but also alkyl substituents bearing further substituents known in the art, such as hydroxy, alkoxy, alkylsulfonyl, halogen atoms, cyano, nitro, amino, carboxyl, etc. Thus, "alkyl group" includes ethers, esters, haloalkyls, nitroalkyls, carboxyalkyls, hydroxyalkyls, sulfoalkyls, etc.

The terms "halo" and "halogen" refer to the fluoro, chloro, bromo or iodo groups. There can be one or more halogen, which are the same or different. Halogens of particular interest include chloro and bromo groups.

The term "haloalkyl" refers to an alkyl group as defined above that is substituted by one or more halogen atoms. The halogen atoms may be the same or different. The term "dihaloalkyl" refers to an alkyl group as described above that is substituted by two halo groups, which may be the same or different. The term "trihaloalkyl" refers to an alkyl group as describe above that is substituted by three halo groups, which may be the same or different. The term "perhaloalkyl" refers to a haloalkyl group as defined above wherein each hydrogen atom in the alkyl group has been replaced by a halogen atom. The term "perfluoroalkyl" refers to a haloalkyl group as defined above wherein each hydrogen atom in the alkyl group has been replaced by a fluoro group.

The term "cycloalkyl" means a mono-, bi-, or tricyclic saturated ring that is fully saturated or partially unsaturated. Examples of such a group included cyclopropyl, cyclobutyl, cyclopentyl, cyclohexyl, cycloheptyl, adamantyl, cyclooctyl, cis- or trans decalin, bicyclo[2.2.1]hept-2-ene, cyclohex-1-enyl, cyclopent-1-enyl, 1,4-cyclooctadienyl, and the like.

The term "(cycloalkyl)alkyl" means the above-defined alkyl group substituted for one of the above cycloalkyl rings. Examples of such a group include (cyclohexyl)methyl, 3-(cyclopropyl)-n-propyl, 5-(cyclopentyl)hexyl, 6-(adamantyl) hexyl, and the like.

The term "substituted phenyl" specifies a phenyl group substituted with one or more moieties, and in some instances one, two, or three moieties, chosen from the groups consisting of halogen, hydroxy, protected hydroxy, cyano, nitro, trifluoromethyl, $C_1$ to $C_7$ alkyl, $C_1$ to $C_7$ alkoxy, $C_1$ to $C_7$ acyl, $C_1$ to $C_7$ acyloxy, carboxy, oxycarboxy, protected carboxy, carboxymethyl, protected carboxymethyl, hydroxymethyl, protected hydroxymethyl, amino, protected amino, (monosubstituted)amino, protected (monosubstituted)amino, (disubstituted)amino, carboxamide, protected carboxamide, N-($C_1$ to $C_6$ alkyl)carboxamide, protected N-($C_1$ to $C_6$ alkyl) carboxamide, N,N-di($C_1$ to $C_6$ alkyl)carboxamide, trifluoromethyl, N-(($C_1$ to $C_6$ alkyl)sulfonyl)amino, N-(phenylsulfonyl)amino or phenyl, substituted or unsubstituted, such that, for example, a biphenyl or naphthyl group results.

Examples of the term "substituted phenyl" includes a mono- or di(halo)phenyl group such as 2, 3 or 4-chlorophenyl, 2,6-dichlorophenyl, 2,5-dichlorophenyl, 3,4-dichlorophenyl, 2, 3 or 4-bromophenyl, 3,4-dibromophenyl, 3-chloro-4-fluorophenyl, 2, 3 or 4-fluorophenyl and the like; a mono or di(hydroxy)phenyl group such as 2, 3, or 4-hydroxyphenyl, 2,4-dihydroxyphenyl, the protected-hydroxy derivatives thereof and the like; a nitrophenyl group such as 2, 3, or 4-nitrophenyl; a cyanophenyl group, for example, 2, 3 or 4-cyanophenyl; a mono- or di(alkyl)phenyl group such as 2, 3, or 4-methylphenyl, 2,4-dimethylphenyl, 2, 3 or 4-(isopropyl)phenyl, 2, 3, or 4-ethylphenyl, 2, 3 or 4-(n-propyl) phenyl and the like; a mono or di(alkoxy)phenyl group, for example, 2,6-dimethoxyphenyl, 2, 3 or 4-(isopropoxy)phenyl, 2, 3 or 4-(t-butoxy)phenyl, 3-ethoxy-4-methoxyphenyl and the like; 2, 3 or 4-trifluoromethylphenyl; a mono- or dicarboxyphenyl or (protected carboxy)phenyl group such as 2, 3 or 4-carboxyphenyl or 2,4-di(protected carboxy)phenyl; a mono- or di(hydroxymethyl)phenyl or (protected hydroxymethyl)phenyl such as 2, 3 or 4-(protected hydroxymethyl)phenyl or 3,4-di(hydroxymethyl)phenyl; a mono- or di(aminomethyl)phenyl or (protected aminomethyl)phenyl such as 2, 3 or 4-(aminomethyl)phenyl or 2,4-(protected aminomethyl)phenyl; or a mono- or di(N-(methylsulfonylamino))phenyl such as 2, 3 or 4-(N-(methylsulfonylamino))phenyl. Also, the term "substituted phenyl" represents disubstituted phenyl groups wherein the substituents are different, for example, 3-methyl-4-hydroxyphenyl, 3-chloro-4-hydroxyphenyl, 2-methoxy-4-bromophenyl, 4-ethyl-2-hydroxyphenyl, 3-hydroxy-4-nitrophenyl, 2-hydroxy-4-chlorophenyl and the like.

The term "(substituted phenyl)alkyl" means one of the above substituted phenyl groups attached to one of the above-described alkyl groups. Examples of include such groups as 2-phenyl-1-chloroethyl, 2-(4'-methoxyphenyl)ethyl, 4-(2',6'-dihydroxy phenyl)n-hexyl, 2-(5'-cyano-3'-methoxyphenyl) n-pentyl, 3-(2',6'-dimethylphenyl)n-propyl, 4-chloro-3-aminobenzyl, 6-(4'-methoxyphenyl)-3-carboxy(n-hexyl), 5-(4'-aminomethylphenyl)-3-(aminomethyl)n-pentyl, 5-phenyl-3-oxo-n-pent-1-yl, (4-hydroxynapth-2-yl)methyl and the like.

As noted above, the term "aromatic" or "aryl" refers to six membered carbocyclic rings. Also as noted above, the term "heteroaryl" denotes optionally substituted five-membered or six-membered rings that have 1 to 4 heteroatoms, such as oxygen, sulfur and/or nitrogen atoms, in particular nitrogen, either alone or in conjunction with sulfur or oxygen ring atoms.

Furthermore, the above optionally substituted five-membered or six-membered rings can optionally be fused to an aromatic 5-membered or 6-membered ring system. For example, the rings can be optionally fused to an aromatic 5-membered or 6-membered ring system such as a pyridine or a triazole system, e.g., to a benzene ring.

The following ring systems are examples of the heterocyclic (whether substituted or unsubstituted) radicals denoted by the term "heteroaryl": thienyl, furyl, pyrrolyl, pyrrolidinyl, imidazolyl, isoxazolyl, triazolyl, thiadiazolyl, oxadiazolyl, tetrazolyl, thiatriazolyl, oxatriazolyl, pyridyl, pyrimidyl, pyrazinyl, pyridazinyl, oxazinyl, triazinyl, thiadiazinyl tetrazolo, 1,5-[b]pyridazinyl and purinyl, as well as benzo-fused derivatives, for example, benzoxazolyl, benzthiazolyl, benzimidazolyl and indolyl.

Substituents for the above optionally substituted heteroaryl rings are from one to three halo, trihalomethyl, amino, protected amino, amino salts, mono-substituted amino, di-substituted amino, carboxy, protected carboxy, carboxylate salts, hydroxy, protected hydroxy, salts of a hydroxy group, lower alkoxy, lower alkylthio, alkyl, substituted alkyl, cycloalkyl, substituted cycloalkyl, (cycloalkyl)alkyl, substituted (cycloalkyl)alkyl, phenyl, substituted phenyl, phenylalkyl, and (substituted phenyl)alkyl. Substituents for the heteroaryl group are as heretofore defined, or in the case of trihalomethyl, can be trifluoromethyl, trichloromethyl, tribromomethyl, or triiodomethyl. As used in conjunction with the above substituents for heteroaryl rings, "lower alkoxy" means a $C_1$ to $C_4$ alkoxy group, similarly, "lower alkylthio" means a $C_1$ to $C_4$ alkylthio group.

The term "(monosubstituted)amino" refers to an amino group with one substituent chosen from the group consisting of phenyl, substituted phenyl, alkyl, substituted alkyl, $C_1$ to $C_4$ acyl, $C_2$ to $C_7$ alkenyl, $C_2$ to $C_7$ substituted alkenyl, $C_2$ to $C_7$ alkynyl, $C_7$ to $C_{16}$ alkylaryl, $C_7$ to $C_{16}$ substituted alkylaryl and heteroaryl group. The (monosubstituted) amino can additionally have an amino-protecting group as encompassed by the term "protected (monosubstituted)amino." The term "(disubstituted)amino" refers to amino groups with two substituents chosen from the group consisting of phenyl, substituted phenyl, alkyl, substituted alkyl, $C_1$ to $C_7$ acyl, $C_2$ to $C_7$ alkenyl, $C_2$ to $C_7$ alkynyl, $C_7$ to $C_{16}$ alkylaryl, $C_7$ to $C_{16}$ substituted alkylaryl and heteroaryl. The two substituents can be the same or different.

The term "heteroaryl(alkyl)" denotes an alkyl group as defined above, substituted at any position by a heteroaryl group, as above defined.

"Optional" or "optionally" means that the subsequently described event, circumstance, feature, or element may, but need not, occur, and that the description includes instances where the event or circumstance occurs and instances in which it does not. For example, "heterocyclo group optionally mono- or di-substituted with an alkyl group" means that the alkyl may, but need not, be present, and the description includes situations where the heterocyclo group is mono- or disubstituted with an alkyl group and situations where the heterocyclo group is not substituted with the alkyl group.

Compounds that have the same molecular formula but differ in the nature or sequence of bonding of their atoms or the arrangement of their atoms in space are termed "isomers." Isomers that differ in the arrangement of their atoms in space are termed "stereoisomers." Stereoisomers that are not mirror images of one another are termed "diastereomers" and those that are non-superimposable mirror images of each other are termed "enantiomers." When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture."

The compounds of this invention may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see, e.g., the discussion in Chapter 4 of "Advanced Organic Chemistry", 4th edition J. March, John Wiley and Sons, New York, 1992).

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "and," and "the" include plural referents unless the context clearly dictates otherwise. Thus, for example, reference to "a compound that reduces apoE4 domain interaction" includes a plurality of such compounds and reference to "the analog" includes reference to one or more analogs and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION OF THE INVENTION

Agents that Reduce apoE4 Domain Interaction

The invention provides agents affecting apoE4 domain interaction, and compositions comprising such agents. By reducing apoE4 domain interaction, apoE4 is rendered more "apoE3-like," and the undesirable effects of apoE4 are reduced. Agents that reduce apoE4 domain interactions are useful in treating apoE4-associated neurological disorders. Agents that reduce apoE4 domain interaction are also useful in treating apoE4-associated disorders related to high serum lipid levels, e.g., cardiovascular disorders.

Agents that reduce apoE4 domain interaction include agents that inhibit formation of a salt bridge between arg-61 and glu-255. Agents of interest are those that reduce apoE4 domain interaction by at least about 10%, at least about 20%, at least about 25%, at least about 30%, at least about 40%, at least about 50%, at least about 60%, at least about 70%, at least about 80%, at least about 90%, or at least about 95% or more, up to 100%, compared to apoE4 domain interaction in the absence of the agent.

Agents of interest are those that affect apoE4 domain interaction without substantially affecting apoE3 structure, i.e., the effect on apoE4 domain interaction is specific to apoE4. Whether an agent specifically reduces apoE4 domain interaction can be determined using an assay such as the emulsion binding assay described in Example 7. Alternatively, whether a compound reduces apoE4 domain interaction is readily determined using a FRET-based assay as described in Example 10.

In some embodiments, an agent that reduces apoE4 domain interaction renders the apoE4 molecule more "apoE3-like," e.g., the apoE4 molecule has apoE3 activity. Thus, in some embodiments, the invention provides methods for converting apoE4 activity to apoE3 activity, comprising contacting an apoE4 molecule with an agent that reduces apoE4 domain interaction. Characteristics of "apoE4 activity" and "apoE3 activity" include, but are not limited to, binding preference of the apolipoprotein for a particular class of lipoprotein; binding to tau protein in vitro and/or in vivo; and binding to Aβ protein. In some embodiments, an agent that reduces apoE4 domain interaction converts apoE4 activity to apoE3 activity such that the apoE4, when contacted with the agent that reduces apoE4 domain interaction, reduces a characteristic of apoE4 by at least about 10%, at least about 20%, at least about 30%, at least about 40%, at least about 50%, at least about 60%, at least about 70%, at least about 80%, at least about 90%, or more, when compared with the characteristic of apoE4 in the absence of the agent.

ApoE4 has a binding preference for VLDL, while apoE3 has a binding preference for HDL. Typically, when plasma lipoproteins are allowed to bind to labeled apoE4 and apoE3, the bound proteins fractionated, and the amount of apoE4 and apoE3 in each fraction measured, the amount of apoE4 in the VLDL, IDL/LDL, and HDL fractions is about 35%, about 23%, about 42%, respectively, while the amount of apoE3 in each of these fractions is about 20%, about 20%, about 60%, respectively. Thus, in some embodiments, an agent that reduces apoE4 domain interaction causes apoE4 to have a binding preference for HDL. Whether apoE4, when contacted with an agent that reduces apoE4 domain interaction, has a binding preference for HDL over VLDL can be determined using any known assay. As one non-limiting example, an assay as described in Dong et al. (1994) *J. Biol. Chem.* 269:22358-22365. For example, samples comprising detectably labeled apoE4 and apoE3 (e.g., labeled with $^{125}$I), are mixed with plasma at about 37° C. for about 2 hours, after which time the samples are fractionated into various lipoprotein classes (e.g., by chromatography), and the amount of label in each fraction is determined.

ApoE3 interacts with tau in vitro, while apoE4 does not. In some embodiments, an agent that reduces apoE4 domain interaction causes apoE4 to bind tau in vitro and/or in vivo. Whether a protein binds tau in vitro, e.g., in the presence of an agent that reduces apoE4 domain interaction, can be determined using standard assays for measuring or detecting protein-protein interaction. A non-limiting example of an assay is provided in Strittmatter et al. (1994) *Exp. Neurol.* 125:163-171.

In many embodiments, agents that reduce apoE4 domain interaction are small organic molecules, generally in the size range of from about 50 daltons to about 2500 daltons, from about 100 daltons to about 2000 daltons, from about 200 daltons to about 1500 daltons, from about 300 daltons to about 1250 daltons, or from about 500 daltons to about 1000 daltons.

The terms "agent," "substance," and "compound" are used interchangeably herein. Candidate agents encompass numerous chemical classes, typically synthetic, semi-synthetic, or naturally-occurring inorganic or organic molecules. Candidate agents may be small organic compounds having a molecular weight of more than about 50 daltons and less than about 2,500 daltons. Candidate agents may comprise functional groups necessary for structural interaction with proteins, e.g., van der Waals interactions, hydrogen bonding, and the like, and may include at an amine, a sulfoalkyl, a carbonyl, a hydroxyl, or a carboxyl group, and may contain at least two of the aforementioned functional chemical groups. The candidate agents may comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries.

Pharmacological agents may be subjected to directed or random and/or directed chemical modifications, such as acylation, alkylation, esterification, amidification, etc. to produce structural analogs. Such structural analogs include those that increase bioavailability, and/or reduced cytotoxicity. Those skilled in the art can readily envision and generate a wide variety of structural analogs, and test them for desired properties such as increased bioavailability and/or reduced cytotoxicity and/or ability to cross the blood-brain barriers.

In many embodiments, agents that reduce apoE4 domain interaction reduce apoE4-mediated inhibition of neurite outgrowth. Whether a compound reduces apoE4-mediated inhibition of neurite outgrowth can be determined using a neurite outgrowth assay as described herein. In general, an agent that reduces apoE4 domain interaction reduces apoE4-mediated inhibition of neurite outgrowth by at least about 10%, at least about 20%, at least about 30%, at least about 40%, at least about 50%, or more, when compared to the inhibition of neurite outgrowth in the presence of apoE4 and the absence of the agent.

Many methods are available to identify agents that reduce apoE4 domain interaction. As one non-limiting example, one can use computer modeling to identify compounds that bind to the N-terminal domain of apoE4. Computer modeling programs are known in the art and include, but are not limited to, the DOCK program, as described in Example 7.

Compounds that bind to the N-terminal domain of apoE4 based on computer modeling may be further evaluated, e.g., by functional assays. Functional assays, include, but are not limited to, an emulsion binding assay (as described in Example 7), assays measuring binding to an LDL receptor, assays measuring binding to LRP, assays measuring binding to HSPG, and neurite outgrowth assays.

In some embodiments, a subject agent that reduces apoE4 domain interaction reduces formation of neurofibrillary tangles in an individual. In these embodiments, a subject agent that reduce apoE4 domain interaction and that reduces formation of neurofibrillary tangles reduces formation of neurofibrillary tangles by at least about 10%, at least about 20%, at least about 30%, at least about 40%, at least about 50%, at least about 60%, at least about 70%, at least about 80%, or at least about 90%, when compared to formation of neurofibrillary tangles in the absence of the agent. Whether neurofibrillary tangle formation is reduced can be determined using, e.g., an experimental animal model of Alzheimer's disease, wherein the animal synthesizes human apoE4 and, as a result, produces neurofibrillary tangles. See, e.g. U.S. Pat. No. 6,046,381.

In some embodiments, a subject agent that reduces apoE4 domain interaction reduces production of Aβ peptide by a cell (e.g., a neuronal cell). For example, in some embodiments, a subject agent that reduces apoE4 domain interaction reduces production of Aβ by at least about 10%, at least about 20%, at least about 30%, at least about 40%, at least about 50%, at least about 60%, at least about 70%, at least about 80%, or at least about 90%, when compared to production of Aβ by a cell in the absence of the agent.

In some embodiments, a subject agent that reduces apoE4 domain interaction reduces production of neurotoxic apoE4 proteolytic fragments. For example, in some embodiments, a subject apoE4 domain interaction inhibiting agent reduces production of neurotoxic apoE4 proteolytic fragments by least about 10%, at least about 20%, at least about 30%, at least about 40%, at least about 50%, at least about 60%, at least about 70%, at least about 80%, or at least about 90%, when compared to the level of neurotoxic apoE4 proteolytic fragments produced in the absence of the agent.

In some embodiments, a subject agent that reduces apoE4 domain interaction reduces Aβ-induced lysosomal leakage. For example, in some embodiments, a subject agent that reduces apoE4 domain interaction reduces Aβ-induced lysosomal leakage by least about 10%, at least about 20%, at least about 30%, at least about 40%, at least about 50%, at least about 60%, at least about 70%, at least about 80%, or at least about 90%, when compared to the level of Aβ-induced lysosomal leakage in the absence of the agent.

In some embodiments, a subject inhibitor of apoE4 domain interaction is one that has an $IC_{50}$ of less than about 100 μM, less than about 75 μM, less than about 50 μM, less than about 25 μM, less than about 10 μM, less than about 1 μM, less than about 100 nM, less than about 80 μM, less than about 60 nM, less than about 50 nM, less than about 25 nM, less than about 10 nM, or less than about 1 nM, or less.

Agents that reduce apoE4 domain interaction to the desired extent may also be assessed for cellular availability, cytotoxicity, biocompatibility, ability to cross the blood-brain barrier, etc., using standard assays.

In some embodiments, a subject inhibitor of apoE4 domain interaction is a compound of Formula I:

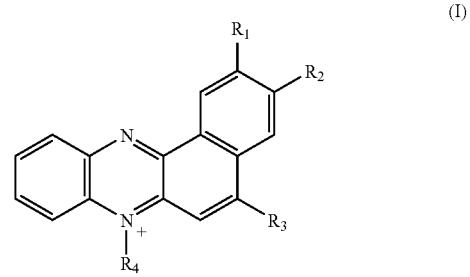

where each of $R_1$, $R_2$, $R_3$, and $R_4$ is independently selected from H; a halo (e.g., bromo, fluoro, chloro); a substituted or unsubstituted, saturated linear or branched hydrocarbon group or chain (e.g., $C_1$ to $C_8$) including, e.g., methyl, ethyl, isopropyl, tert-butyl, heptyl, n-octyl, dodecyl, octadecyl, amyl, 2-ethylhexyl; an ether group, such as a methoxyl group or an ethoxyl group; a substituted or unsubstituted sulfate group; a substituted or unsubstituted phenyl group; and a substituted or unsubstituted heteroaromatic group; and pro-drugs, pharmaceutically acceptable salts, pharmaceutically acceptable derivatives, and pharmaceutically acceptable esters thereof.

In some embodiments, a subject apoE4 domain interaction inhibitor compound is of Formula I, where:

$R_1$ and $R_2$ are each independently —H, —$(CH_2)_n$—$SO_3$, or —$(CH_2)_n$—O—$SO_3$, where n=0, 1, or 2; with the proviso that only one of $R_1$ and $R_2$ is —H;

$R_3$ is —$(CH_2)_m$—$SO_3$, —$(CH_2)_m$—O—$SO_3$, —NH—$(CH_2)_n$—$SO_3$, —NH—$(CH_2)_n$—O—$SO_3$, $(CH_2)_p$—$C_6H_4$—$SO_3$, —$(CH_2)_p$—$C_6H_4$—O—$SO_3$, —NH—$(CH_2)_p$—$C_6H_4$—$SO_3$, or —NH—$(CH_2)_p$—$C_6H_4$—O—$SO_3$; where m=0 or an integer from 1 to 10; where n=1, 2, or 3; and where p=0 or 1; and $R_4$ is lower alkyl ($C_1$-$C_4$) or —$(CH_2)_n$—$C_6H_5$ where n=0 or 1; and pro-drugs, pharmaceutically acceptable salts, pharmaceutically acceptable derivatives, and pharmaceutically acceptable esters thereof.

In some embodiments, a subject apoE4 domain interaction inhibitor has the structure depicted in Formula Ia (also referred to as GIND-25):

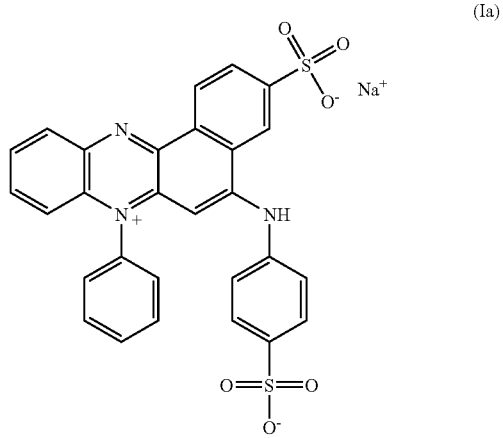

In some embodiments, a subject apoE4 domain interaction inhibitor is a compound of Formula II:

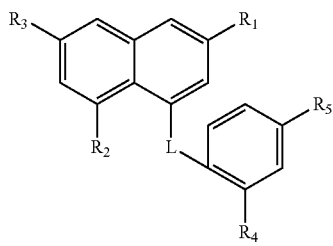
(II)

wherein each of $R_1$, $R_2$, $R_3$, $R_4$, $R_5$ and L is independently selected from H; a halo (e.g., bromo, fluoro, chloro); a substituted or unsubstituted, saturated linear or branched hydrocarbon group or chain (e.g., $C_1$ to $C_8$) including, e.g., methyl, ethyl, isopropyl, tert-butyl, heptyl, n-octyl, dodecyl, octadecyl, amyl, 2-ethylhexyl; an ether group, such as a methoxyl group or an ethoxyl group; a substituted or unsubstituted sulfate group; a substituted or unsubstituted phenyl group; and a substituted or unsubstituted heteroaromatic group; and pro-drugs, pharmaceutically acceptable salts, pharmaceutically acceptable derivatives, and pharmaceutically acceptable esters thereof.

In some embodiments, a subject apoE4 domain interaction inhibitor compound is of Formula II, where:

$R_1$ and $R_3$ are each independently —H, —$(CH_2)_n$—$SO_3$, or —$(CH_2)_n$—O—$SO_3$, where n=0, 1, or 2; with the proviso that at least one of $R_1$ and $R_2$ is other than —H;

$R_2$ and $R_4$ are each independently —H, —O, —OH, or —$NH_2$;

$R_5$ is —OR, —NHR, or $NR_2$ where R=—$CH_3$, or —$CH_2CH_3$; and

L is —N=N—; —CH=CH—, —N=CH—, —CH=N—, —$CH_2$—$CH_2$—, —NH—$CH_2$—, —$CH_2$—NH—, —O—$CH_2$—, or —$CH_2$—O—, and pro-drugs, pharmaceutically acceptable salts, pharmaceutically acceptable derivatives, and pharmaceutically acceptable esters thereof.

In some embodiments, a subject apoE4 domain interaction inhibitor has the structure depicted in Formula IIa (also referred to as GIND-28):

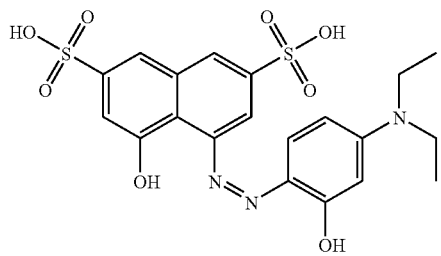
(IIa)

In some embodiments, a subject apoE4 domain interaction inhibitor is a compound of Formula III:

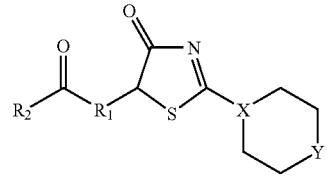
(III)

wherein each of $R_1$ and $R_2$ is independently selected from H; a halo (e.g., bromo, fluoro, chloro); a substituted or unsubstituted, saturated linear or branched hydrocarbon group or chain (e.g., $C_1$ to $C_8$) including, e.g., methyl, ethyl, isopropyl, tert-butyl, heptyl, n-octyl, dodecyl, octadecyl, amyl, 2-ethylhexyl; an ether group, such as a methoxyl group or an ethoxyl group; a substituted or unsubstituted phenyl group; and a substituted or unsubstituted heteroaromatic group; wherein X and Y are each independently C, O, or N; and pro-drugs, pharmaceutically acceptable salts, pharmaceutically acceptable derivatives, and pharmaceutically acceptable esters thereof.

In some embodiments, a subject apoE4 domain interaction inhibitor compound is of Formula III, where:

$R_1$ is —$(CH_2)_m$—$(CR=CH)_n$—CR= where m and n are each independently 0 or 1, and R is —$C_6H_5$, —$(CH_2)$—$(C_6H_5)$, —(NH)—$C_6H_5$, or —(O)—$C_6H_5$;

$R_2$ is is —$C_6H_5$, —$(CH_2)$—$C_6H_5$, —(NH)—$C_6H_5$, or —(O)—$C_6H_5$; and X and Y are each independently O or N; and pro-drugs, pharmaceutically acceptable salts, pharmaceutically acceptable derivatives, and pharmaceutically acceptable esters thereof.

In some embodiments, a subject apoE4 domain interaction inhibitor has the structure depicted in Formula IIIa (also referred to as GIND-81):

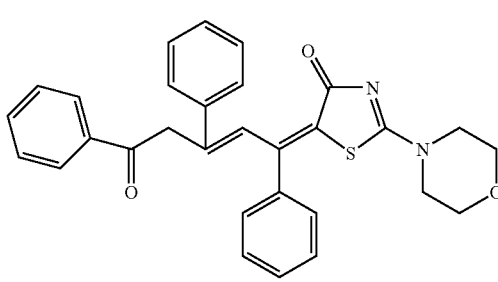
(IIIa)

In some embodiments, a subject apoE4 domain interaction inhibitor is a compound of Formula IV:

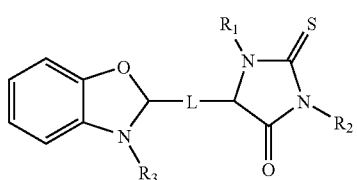
(IV)

wherein each of $R_1$, $R_2$, $R_3$, and L is independently selected from H; a halo (e.g., bromo, fluoro, chloro); a substituted or unsubstituted, saturated linear or branched hydrocarbon group or chain (e.g., $C_1$ to $C_8$) including, e.g., methyl, ethyl, isopropyl, tert-butyl, heptyl, n-octyl, dodecyl, octadecyl, amyl, 2-ethylhexyl; an ether group, such as a methoxyl group or an ethoxyl group; a substituted or unsubstituted phenyl group; and a substituted or unsubstituted heteroaromatic group; and pro-drugs, pharmaceutically acceptable salts, pharmaceutically acceptable derivatives, and pharmaceutically acceptable esters thereof.

In some embodiments, a subject apoE4 domain interaction inhibitor compound is of Formula IV, where:

$R_1$ and $R_2$ are each independently —H or lower alkyl (e.g., $C_1$-$C_4$); with the proviso that at least one of $R_1$ and $R_2$ is alkylated;

$R_3$ is —$(CH_2)_n$—$SO_3$, or —$(CH_2)_n$—O—$SO_3$ where n=1-4; and

L is —$(CH_2)_m$, =CH—$(CH_2)_n$—CH=, —CH=CH—$(CH_2)$—, or —$(CH_2)$—CH=CH—, where m=0, or an integer from 1-3; and where n=0 or 1; and pro-drugs, pharmaceutically acceptable salts, pharmaceutically acceptable derivatives, and pharmaceutically acceptable esters thereof.

In some embodiments, a subject apoE4 domain interaction inhibitor has the structure depicted in Formula IVa (also referred to as GIND-105):

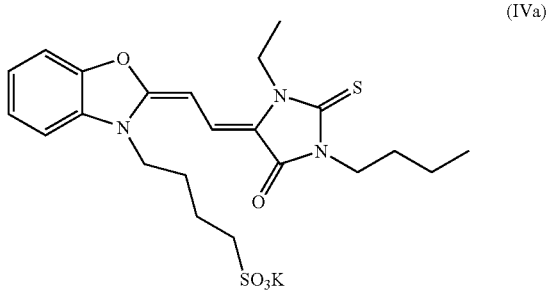

(IVa)

In some embodiments, a subject apoE4 domain interaction inhibitor is a compound of Formula V:

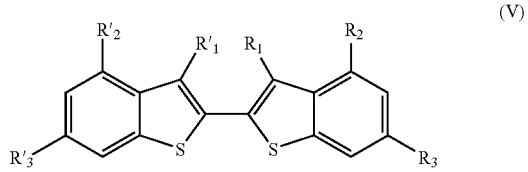

(V)

wherein each of $R_1$, $R_2$, $R_3$, and each of $R_1'$, $R_2'$, and $R_3'$ is independently selected from H; a halo (e.g., bromo, fluoro, chloro); a substituted or unsubstituted, saturated linear or branched hydrocarbon group or chain (e.g., $C_1$ to $C_8$) including, e.g., methyl, ethyl, isopropyl, tert-butyl, heptyl, n-octyl, dodecyl, octadecyl, amyl, 2-ethylhexyl; an ether group, such as a methoxyl group or an ethoxyl group; a substituted or unsubstituted sulfate group; a substituted or unsubstituted phenyl group; and a substituted or unsubstituted heteroaromatic group; and pro-drugs, pharmaceutically acceptable salts, pharmaceutically acceptable derivatives, and pharmaceutically acceptable esters thereof.

In some embodiments, a subject apoE4 domain interaction inhibitor compound is of Formula V, where:

$R_1$ and $R_1'$ are each independently —H or —O—$SO_3$, with the proviso that at least one of $R_1$ and $R_1'$ is $SO_3$;

$R_2$ and $R_2'$ are each independently —H, —$CH_3$, or —$CH_2CH_3$ with the proviso that at least one of $R_2$ and $R_2'$ is alkylated; and $R_3$ and $R_3'$ are each independently —H, —Cl, or —Br, with the proviso that at least one of $R_3$ and $R_3'$ is halogenated; and pro-drugs, pharmaceutically acceptable salts, pharmaceutically acceptable derivatives, and pharmaceutically acceptable esters thereof.

In some embodiments, a subject apoE4 domain interaction inhibitor has the structure depicted in Formula Va (also referred to as GIND-111):

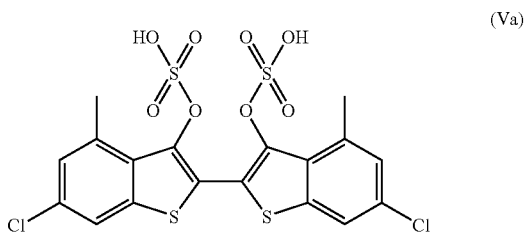

(Va)

In some embodiments, a subject apoE4 domain interaction inhibitor has the structure depicted in Formula VI:

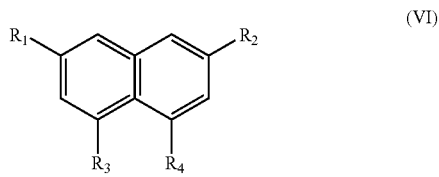

(VI)

wherein each of $R_1$, $R_2$, $R_3$, and $R_4$ is independently selected from H; a halo (e.g., bromo, fluoro, chloro); a substituted or unsubstituted, saturated linear or branched hydrocarbon group or chain (e.g., $C_1$ to $C_8$) including, e.g., methyl, ethyl, isopropyl, tert-butyl, heptyl, n-octyl, dodecyl, octadecyl, amyl, 2-ethylhexyl; an ether group, such as a methoxyl group or an ethoxyl group; a substituted or unsubstituted sulfate group; a substituted or unsubstituted phenyl group; and a substituted or unsubstituted heteroaromatic group; and pro-drugs, pharmaceutically acceptable salts, pharmaceutically acceptable derivatives, and pharmaceutically acceptable esters thereof.

In some embodiments, a subject apoE4 domain interaction inhibitor compound is of Formula VI, where:

where $R_1$ and $R_2$ are each independently —H, —$(CH_2)_n$—$SO_3$, or —$(CH_2)_n$—)—$SO_3$, where n=0, 1, or 2; with the proviso that at least one of $R_1$ and $R_2$ is other than —H;

$R_3$ is O, H, OH, a halo (e.g., bromo, fluoro, chloro), or a substituted or unsubstituted, saturated linear or branched hydrocarbon group or chain (e.g., $C_1$ to $C_8$); and $R_4$ is —N=N—$R_5$; —CH=CH—$R_5$, —N=CH—$R_5$, —CH=N—$R_5$, —$CH_2$—$CH_2$—$R_5$, —NH—$CH_2$—$R_5$, —$CH_2$—NH—$R_5$, —O—$CH_2$—$R_5$, —$CH_2$—O—$R_5$, a substituted or unsubstituted phenyl group; a substituted or unsubstituted heteroaromatic group, or a substituted or unsubstituted, saturated linear or branched hydrocarbon group or chain (e.g., $C_1$ to $C_8$); where $R_5$ is H, a substituted or unsubstituted phenyl group; a substituted or unsubstituted heteroaromatic group, or a substituted or unsubstituted, saturated linear or branched hydrocarbon group or chain (e.g., $C_1$ to $C_8$); and pro-drugs, pharmaceutically acceptable salts, pharmaceutically acceptable derivatives, and pharmaceutically acceptable esters thereof.

In some embodiments, a subject apoE4 domain interaction inhibitor compound is of Formula VII:

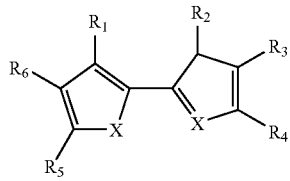

(VII)

wherein each of $R_1$, $R_2$, $R_3$, $R_4$, $R_5$, and $R_6$ is independently selected from H; a halo (e.g., bromo, fluoro, chloro); a substituted or unsubstituted, saturated linear or branched hydrocarbon group or chain (e.g., $C_1$ to $C_8$) including, e.g., methyl, ethyl, isopropyl, tert-butyl, heptyl, n-octyl, dodecyl, octadecyl, amyl, 2-ethylhexyl; an ether group, such as a methoxyl group or an ethoxyl group; a substituted or unsubstituted sulfate group; a substituted or unsubstituted phenyl group; and a substituted or unsubstituted heteroaromatic group; and pro-drugs, pharmaceutically acceptable salts, pharmaceutically acceptable derivatives, and pharmaceutically acceptable esters thereof.

In some embodiments, a subject apoE4 domain interaction inhibitor compound is of Formula VII, where:

$R_1$ and $R_2$ are each independently —H or —O—$SO_3$, —$(CH_2)_n$—$SO_3$, or —$(CH_2)_n$—O—$SO_3$, where n=0, 1, or 2; with the proviso that at least one of $R_1$ and $R_2$ is other than —H;

X is C, S, or N;

each of $R_3$, $R_4$, $R_5$, and $R_6$ is independently selected from H, a halo (e.g., bromo, fluoro, chloro); a substituted or unsubstituted, saturated linear or branched hydrocarbon group or chain (e.g., $C_1$ to $C_8$), a substituted or unsubstituted phenyl group; and a substituted or unsubstituted heteroaromatic group; and pro-drugs, pharmaceutically acceptable salts, pharmaceutically acceptable derivatives, and pharmaceutically acceptable esters thereof.

In some embodiments, a subject apoE4 domain interaction inhibitor compound is of Formula VIII:

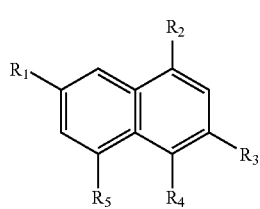

(VIII)

wherein each of $R_1$, $R_2$, $R_3$, $R_4$, and $R_5$ is independently selected from H; a halo (e.g., bromo, fluoro, chloro); a substituted or unsubstituted, saturated linear or branched hydrocarbon group or chain (e.g., $C_1$ to $C_8$) including, e.g., methyl, ethyl, isopropyl, tert-butyl, heptyl, n-octyl, dodecyl, octadecyl, amyl, 2-ethylhexyl; an ether group, such as a methoxyl group or an ethoxyl group; a substituted or unsubstituted sulfate group; a substituted or unsubstituted phenyl group; and a substituted or unsubstituted heteroaromatic group; and pro-drugs, pharmaceutically acceptable salts, pharmaceutically acceptable derivatives, and pharmaceutically acceptable esters thereof.

In some embodiments, a subject apoE4 domain interaction inhibitor compound is of Formula VIII, where:

$R_1$ is —O—$SO_3$, —$(CH_2)_n$—$SO_3$, or —$(CH_2)_n$—O—$SO_3$, where n=0, 1, or 2;

wherein each of $R_2$, $R_3$, $R_4$, and $R_5$ is independently selected from H; a halo (e.g., bromo, fluoro, chloro); a substituted or unsubstituted, saturated linear or branched hydrocarbon group or chain (e.g., $C_1$ to $C_8$); a substituted or unsubstituted phenyl group; and a substituted or unsubstituted heteroaromatic group; or —$(CH_2)_m$—$SO_3$, —$(CH_2)_m$—O—$SO_3$, —NH—$(CH_2)_n$—$SO_3$, —NH—$(CH_2)_n$—O—$SO_3$, $(CH_2)_p$—$C_6H_4$—$SO_3$, —$(CH_2)_p$—$C_6H_4$—O—$SO_3$, —NH—$(CH_2)_p$—$C_6H_4$—$SO_3$, or —NH—$(CH_2)_p$—$C_6H_4$—O—$SO_3$; where m=0 or an integer from 1 to 10; where n=1, 2, or 3; and where p=0 or 1;

and pro-drugs, pharmaceutically acceptable salts, pharmaceutically acceptable derivatives, and pharmaceutically acceptable esters thereof.

In some embodiments, a subject apoE4 domain interaction inhibitor compound is of Formula VIII, where:

$R_1$ is —O—$SO_3$, —$(CH_2)_n$—$SO_3$, or —$(CH_2)_n$—O—$SO_3$, where n=0, 1, or 2;

$R_2$ is —$(CH_2)_m$—$SO_3$, —$(CH_2)_m$—O—$SO_3$, —NH—$CH_2)_n$—$SO_3$, —NH—$(CH_2)_n$—O—$SO_3$, $(CH_2)_p$—$C_6H_4$—$SO_3$, —$(CH_2)_p$—$C_6H_4$—O—$SO_3$, —NH—$(CH_2)_p$—$C_6H_4$—$SO_3$, or —NH—$(CH_2)_p$—$C_6H_4$—O—$SO_3$; where m=0 or an integer from 1 to 10; where n=1, 2, or 3; and where p=0 or 1; and each of $R_3$, $R_4$, and $R_5$ is independently selected from H; a halo (e.g., bromo, fluoro, chloro); a substituted or unsubstituted, saturated linear or branched hydrocarbon group or chain (e.g., $C_1$ to $C_8$); a substituted or unsubstituted phenyl group; and a substituted or unsubstituted heteroaromatic group;

and pro-drugs, pharmaceutically acceptable salts, pharmaceutically acceptable derivatives, and pharmaceutically acceptable esters thereof.

In some embodiments, a subject apoE4 domain interaction inhibitor compound is of Formula IX:

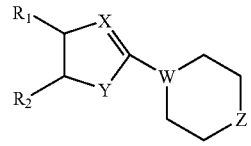

(IX)

where W, X, Y, and X are each independently C, N, S, or O;

where each of $R_1$ and $R_2$ is independently selected from H; a halo (e.g., bromo, fluoro, chloro); a substituted or unsubstituted, saturated linear or branched hydrocarbon group or chain (e.g., $C_1$ to $C_8$) including, e.g., methyl, ethyl, isopropyl, tert-butyl, heptyl, n-octyl, dodecyl, octadecyl, amyl, 2-ethylhexyl; an ether group, such as a methoxyl group or an ethoxyl group; a substituted or unsubstituted sulfate group; a substituted or unsubstituted phenyl group; and a substituted or unsubstituted heteroaromatic group;

and pro-drugs, pharmaceutically acceptable salts, pharmaceutically acceptable derivatives, and pharmaceutically acceptable esters thereof.

In some embodiments, a subject apoE4 domain interaction inhibitor compound is of Formula IX:

where W, X, Y, and X are each independently C, N, S, or O;

where $R_1$ is selected from H, =O, a halo (e.g., bromo, fluoro, chloro), —O—SO$_3$, —(CH$_2$)$_n$—SO$_3$, or —(CH$_2$)$_n$—O—SO$_3$, where n=0, 1, or 2; and where $R_2$ is selected from H, a halo (e.g., bromo, fluoro, chloro); —O—SO$_3$, —(CH$_2$)$_n$—SO$_3$, or —(CH$_2$)$_n$—O—SO$_3$, where n=0, 1, or 2; —(CH$_2$)$_m$—(CR=CH)$_n$—CR= where m and n are each independently 0 or 1, and R is —C$_6$H$_5$, —(CH$_2$)—C$_6$H$_5$, —(NH)—C$_6$H$_5$, or —(O)—C$_6$H$_5$; and —C$_6$H$_5$, —(CH$_2$)—C$_6$H$_5$, —(NH)—C$_6$H$_5$, or —(O)—C$_6$H$_5$;

and pro-drugs, pharmaceutically acceptable salts, pharmaceutically acceptable derivatives, and pharmaceutically acceptable esters thereof.

In some embodiments, a subject apoE4 domain interaction inhibitor compound is of Formula X:

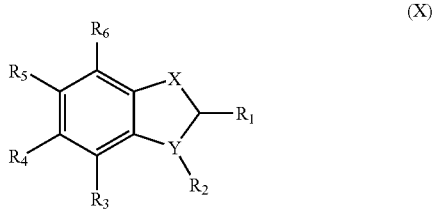

(X)

where X and Y are each independently C, N, S, or O;

where $R_1$, $R_2$, $R_3$, $R_4$, $R_5$, and $R_6$ are each independently H; a halo (e.g., bromo, fluoro, chloro); a substituted or unsubstituted, saturated linear or branched hydrocarbon group or chain (e.g., $C_1$ to $C_8$) including, e.g., methyl, ethyl, isopropyl, tert-butyl, heptyl, n-octyl, dodecyl, octadecyl, amyl, 2-ethylhexyl; an ether group, such as a methoxyl group or an ethoxyl group; a substituted or unsubstituted sulfate group; a substituted or unsubstituted phenyl group; and a substituted or unsubstituted heteroaromatic group;

and pro-drugs, pharmaceutically acceptable salts, pharmaceutically acceptable derivatives, and pharmaceutically acceptable esters thereof.

In some embodiments, a subject apoE4 domain interaction inhibitor compound is of Formula X:

where X and Y are each independently C, N, S, or O;

where $R_2$ is selected from H; a halo; —(CH$_2$)$_n$—SO$_3$, or —(CH$_2$)$_n$—O—SO$_3$ where n=1-4; a substituted or unsubstituted, saturated linear or branched hydrocarbon group or chain (e.g., $C_1$ to $C_8$); a substituted or unsubstituted phenyl group; and a substituted or unsubstituted heteroaromatic group;

$R_1$ is selected from H; a halo; substituted or unsubstituted, saturated linear or branched hydrocarbon group or chain (e.g., $C_1$ to $C_8$); a substituted or unsubstituted phenyl group; a substituted or unsubstituted heteroaromatic group; and L-$R_7$, where L is —(CH$_2$)$_m$, =CH—(CH$_2$)$_n$—CH=, —CH=CH—(CH$_2$)—, or —CH$_2$—CH=CH—, where m=0, or an integer from 1-3, where n=0 or 1, and where $R_7$ is a substituted or unsubstituted, saturated linear or branched hydrocarbon group or chain (e.g., $C_1$ to $C_8$); a substituted or unsubstituted phenyl group; and a substituted or unsubstituted heteroaromatic group;

where $R_3$, $R_4$, $R_5$, and $R_6$ are each independently H; a halo (e.g., bromo, fluoro, chloro); a substituted or unsubstituted, saturated linear or branched hydrocarbon group or chain (e.g., $C_1$ to $C_8$) including, e.g., methyl, ethyl, isopropyl, tert-butyl, heptyl, n-octyl, dodecyl, octadecyl, amyl, 2-ethylhexyl; an ether group, such as a methoxyl group or an ethoxyl group; a substituted or unsubstituted sulfate group; a substituted or unsubstituted phenyl group; and a substituted or unsubstituted heteroaromatic group;

and pro-drugs, pharmaceutically acceptable salts, pharmaceutically acceptable derivatives, and pharmaceutically acceptable esters thereof.

In some embodiments, one or more of the compounds depicted in Formulas Ia, IIa, IIIa, IVa, and Va is specifically excluded.

Compositions

The invention further provides compositions comprising an agent that reduces apoE4 domain interaction. These compositions may include a buffer, which is selected according to the desired use of the agent, and may also include other substances appropriate to the intended use. Those skilled in the art can readily select an appropriate buffer, a wide variety of which are known in the art, suitable for an intended use. In some instances, the composition can comprise a pharmaceutically acceptable excipient, a variety of which are known in the art and need not be discussed in detail herein. Pharmaceutically acceptable excipients have been amply described in a variety of publications, including, for example, A. Gennaro (1995) "Remington: The Science and Practice of Pharmacy", 19th edition, Lippincott, Williams, & Wilkins.

Formulations, Dosages, and Routes of Administration

The invention provides formulations, including pharmaceutical formulations, comprising an agent that reduces apoE4 domain interaction. In general, a formulation comprises an effective amount of an agent that reduces apoE4 domain interaction. An "effective amount" means a dosage sufficient to produce a desired result, e.g., reduction in apoE4 domain interaction, an increase in neurite outgrowth, a reduction in serum lipid levels, a reduced risk of heart disease, etc. Generally, the desired result is at least a reduction in apoE4 domain interaction as compared to a control. An agent that reduces apoE4 domain interaction may delivered in such a manner as to avoid the blood-brain barrier, as described in more detail below. An agent that reduces apoE4 domain interaction may be formulated and/or modified to enable the agent to cross the blood-brain barrier, as described in more detail below.

Formulations

In the subject methods, the active agent(s) may be administered to the host using any convenient means capable of resulting in the desired reduction in apoE4 domain interaction. Thus, the agent can be incorporated into a variety of formulations for therapeutic administration. More particularly, the agents of the present invention can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols.

In pharmaceutical dosage forms, the agents may be administered in the form of their pharmaceutically acceptable salts, or they may also be used alone or in appropriate association, as well as in combination, with other pharmaceutically active compounds. The following methods and excipients are merely exemplary and are in no way limiting.

For oral preparations, the agents can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The agents can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The agents can be utilized in aerosol formulation to be administered via inhalation. The compounds of the present invention can be formulated into pressurized acceptable propellants such as dichlorodifluoromethane, propane, nitrogen and the like.

Furthermore, the agents can be made into suppositories by mixing with a variety of bases such as emulsifying bases or water-soluble bases. The compounds of the present invention can be administered rectally via a suppository. The suppository can include vehicles such as cocoa-butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or intravenous administration may comprise the inhibitor(s) in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular compound employed and the effect to be achieved, and the pharmacodynamics associated with each compound in the host.

Other modes of administration will also find use with the subject invention. For instance, an agent of the invention can be formulated in suppositories and, in some cases, aerosol and intranasal compositions. For suppositories, the vehicle composition will include traditional binders and carriers such as, polyalkylene glycols, or triglycerides. Such suppositories may be formed from mixtures containing the active ingredient in the range of about 0.5% to about 10% (w/w), e.g., about 1% to about 2%.

Intranasal formulations will usually include vehicles that neither cause irritation to the nasal mucosa nor significantly disturb ciliary function. Diluents such as water, aqueous saline or other known substances can be employed with the subject invention. The nasal formulations may also contain preservatives such as, but not limited to, chlorobutanol and benzalkonium chloride. A surfactant may be present to enhance absorption of the subject proteins by the nasal mucosa.

An agent of the invention can be administered as injectables. Typically, injectable compositions are prepared as liquid solutions or suspensions; solid forms suitable for solution in, or suspension in, liquid vehicles prior to injection may also be prepared. The preparation may also be emulsified or the active ingredient encapsulated in liposome vehicles.

Suitable excipient vehicles are, for example, water, saline, dextrose, glycerol, ethanol, or the like, and combinations thereof. In addition, if desired, the vehicle may contain minor amounts of auxiliary substances such as wetting or emulsifying agents or pH buffering agents. Actual methods of preparing such dosage forms are known, or will be apparent, to those skilled in the art. See, e.g., Remington's Pharmaceutical Sciences, Mack Publishing Company, Easton, Pa., 17th edition, 1985. The composition or formulation to be administered will, in any event, contain a quantity of the agent adequate to achieve the desired state in the subject being treated.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Oral Formulations

In some embodiments, a subject active agent that inhibits apoE4 domain interaction is formulated for oral delivery to an individual in need of such an agent.

For oral delivery, a subject formulation comprising a subject active agent will in some embodiments include an enteric-soluble coating material. Suitable enteric-soluble coating material include hydroxypropyl methylcellulose acetate succinate (HPMCAS), hydroxypropyl methyl cellulose phthalate (HPMCP), cellulose acetate phthalate (CAP), polyvinyl phthalic acetate (PVPA), Eudragit™, and shellac.

As one non-limiting example of a suitable oral formulation, a subject active agent that inhibits apoE4 domain interaction is formulated with one or more pharmaceutical excipients and coated with an enteric coating, as described in U.S. Pat. No. 6,346,269. For example, a solution comprising a subject active agent that inhibits apoE4 domain interaction and a stabilizer is coated onto a core comprising pharmaceutically acceptable excipients, to form an active agent-coated core; a sub-coating layer is applied to the active agent-coated core, which is then coated with an enteric coating layer. The core generally includes pharmaceutically inactive components such as lactose, a starch, mannitol, sodium carboxymethyl cellulose, sodium starch glycolate, sodium chloride, potassium chloride, pigments, salts of alginic acid, talc, titanium dioxide, stearic acid, stearate, micro-crystalline cellulose, glycerin, polyethylene glycol, triethyl citrate, tributyl citrate, propanyl triacetate, dibasic calcium phosphate, tribasic sodium phosphate, calcium sulfate, cyclodextrin, and castor oil. Suitable solvents for the active agent (a subject agent that inhibits apoE4 domain interaction) include aqueous solvents. Suitable stabilizers include alkali-metals and alkaline earth metals, bases of phosphates and organic acid salts and organic amines. The sub-coating layer comprises one or more of an adhesive, a plasticizer, and an anti-tackiness agent. Suitable anti-tackiness agents include talc, stearic acid, stearate, sodium stearyl fumarate, glyceryl behenate, kaolin and aerosil. Suitable adhesives include polyvinyl pyrrolidone (PVP), gelatin, hydroxyethyl cellulose (HEC), hydroxypropyl cellulose (HPC), hydroxypropyl methyl cellulose (HPMC), vinyl acetate (VA), polyvinyl alcohol (PVA), methyl cellulose (MC), ethyl cellulose (EC), hydroxypropyl methyl cellulose phthalate (HPMCP), cellulose acetate phthalates (CAP), xanthan gum, alginic acid, salts of alginic acid, Eudragit™, copolymer of methyl acrylic acid/methyl methacrylate with polyvinyl acetate phthalate (PVAP). Suitable plasticizers include glycerin, polyethylene glycol, triethyl citrate, tributyl citrate, propanyl triacetate and castor oil.

Suitable enteric-soluble coating material include hydroxypropyl methylcellulose acetate succinate (HPMCAS), hydroxypropyl methyl cellulose phthalate (HPMCP), cellulose acetate phthalate (CAP), polyvinyl phthalic acetate (PVPA), Eudragit™ and shellac.

Suitable oral formulations also include a subject active agent that inhibits apoE4 domain interaction, formulated with any of the following: microgranules (see, e.g., U.S. Pat. No. 6,458,398); biodegradable macromers (see, e.g., U.S. Pat. No. 6,703,037); biodegradable hydrogels (see, e.g., Graham and McNeill (1989) *Biomaterials* 5:27-36); biodegradable particulate vectors (see, e.g., U.S. Pat. No. 5,736,371); bioabsorbable lactone polymers (see, e.g., U.S. Pat. No. 5,631,015); slow release protein polymers (see, e.g., U.S. Pat. No. 6,699,504; Pelias Technologies, Inc.); a poly(lactide-co-glycolide/polyethylene glycol block copolymer (see, e.g., U.S. Pat. No. 6,630,155; Atrix Laboratories, Inc.); a composition comprising a biocompatible polymer and particles of metal cation-stabilized agent dispersed within the polymer (see, e.g., U.S. Pat. No. 6,379,701; Alkermes Controlled Therapeutics, Inc.); and microspheres (see, e.g., U.S. Pat. No. 6,303,148; Octoplus, B. V.).

Suitable oral formulations also include a subject active agent that inhibits apoE4 domain interaction formulated with any of the following: a carrier such as Emisphere® (Emisphere Technologies, Inc.); TIMERx, a hydrophilic matrix combining xanthan and locust bean gums which, in the presence of dextrose, form a strong binder gel in water (Penwest); Geminex™ (Penwest); Procise™ (GlaxoSmithKline); SAVIT™ (Mistral Pharma Inc.); RingCap™ (Alza Corp.); Smartrix® (Smartrix Technologies, Inc.); SQZgel™ (MacroMed, Inc.); Geomatrix™ (Skye Pharma, Inc.); Oros® Trilayer (Alza Corporation); and the like.

Also suitable for use are formulations such as those described in U.S. Pat. No. 6,296,842 (Alkermes Controlled Therapeutics, Inc.); U.S. Pat. No. 6,187,330 (Scios, Inc.); and the like.

Also suitable for use herein are formulations comprising an intestinal absorption enhancing agent. Suitable intestinal absorption enhancers include, but are not limited to, calcium chelators (e.g., citrate, ethylenediamine tetracetic acid); surfactants (e.g., sodium dodecyl sulfate, bile salts, palmitoylcarhitine, and sodium salts of fatty acids); toxins (e.g., zonula occludens toxin); and the like.

Controlled Release Formulations

In some embodiments, a subject active agent that inhibits apoE4 domain interaction is formulated in a controlled release formulation.

Controlled release within the scope of this invention can be taken to mean any one of a number of extended release dosage forms. The following terms may be considered to be substantially equivalent to controlled release, for the purposes of the present invention: continuous release, controlled release, delayed release, depot, gradual release, long-term release, programmed release, prolonged release, proportionate release, protracted release, repository, retard, slow release, spaced release, sustained release, time coat, timed release, delayed action, extended action, layered-time action, long acting, prolonged action, repeated action, slowing acting, sustained action, sustained-action medications, and extended release. Further discussions of these terms may be found in Lesczek Krowczynski, *Extended-Release Dosage Forms*, 1987 (CRC Press, Inc.).

The various controlled release technologies cover a very broad spectrum of drug dosage forms. Controlled release technologies include, but are not limited to physical systems and chemical systems.

Physical systems include, but are not limited to, reservoir systems with rate-controlling membranes, such as microencapsulation, macroencapsulation, and membrane systems; reservoir systems without rate-controlling membranes, such as hollow fibers, ultra microporous cellulose triacetate, and porous polymeric substrates and foams; monolithic systems, including those systems physically dissolved in non-porous, polymeric, or elastomeric matrices (e.g., nonerodible, erodible, environmental agent ingression, and degradable), and materials physically dispersed in non-porous, polymeric, or elastomeric matrices (e.g., nonerodible, erodible, environmental agent ingression, and degradable); laminated structures, including reservoir layers chemically similar or dissimilar to outer control layers; and other physical methods, such as osmotic pumps, or adsorption onto ion-exchange resins.

Chemical systems include, but are not limited to, chemical erosion of polymer matrices (e.g., heterogeneous, or homogeneous erosion), or biological erosion of a polymer matrix (e.g., heterogeneous, or homogeneous). Additional discussion of categories of systems for controlled release may be found in Agis F. Kydonieus, *Controlled Release Technolozies: Methods Theory and Applications*, 1980 (CRC Press, Inc.).

There are a number of controlled release drug formulations that are developed for oral administration. These include, but are not limited to, osmotic pressure-controlled gastrointestinal delivery systems; hydrodynamic pressure-controlled gastrointestinal delivery systems; membrane permeation-controlled gastrointestinal delivery systems, which include microporous membrane permeation-controlled gastrointestinal delivery devices; gastric fluid-resistant intestine targeted controlled-release gastrointestinal delivery devices; gel diffusion-controlled gastrointestinal delivery systems; and ion-exchange-controlled gastrointestinal delivery systems, which include cationic and anionic drugs. Additional information regarding controlled release drug delivery systems may be found in Yie W. Chien, *Novel Drug Delivery Systems*, 1992 (Marcel Dekker, Inc.). Some of these formulations will now be discussed in more detail.

Enteric coatings are applied to tablets to prevent the release of drugs in the stomach either to reduce the risk of unpleasant side effects or to maintain the stability of the drug which might otherwise be subject to degradation of expose to the gastric environment. Most polymers that are used for this purpose are polyacids that function by virtue or the fact that their solubility in aqueous medium is pH-dependent, and they require conditions with a pH higher than normally encountered in the stomach.

One exemplary type of oral controlled release structure is enteric coating of a solid or liquid dosage form. The enteric coatings are designed to disintegrate in intestinal fluid for ready absorption. Delay of absorption of the active agent that is incorporated into a formulation with an enteric coating is dependent on the rate of transfer through the gastrointestinal tract, and so the rate of gastric emptying is an important factor. Some investigators have reported that a multiple-unit type dosage form, such as granules, may be superior to a single-unit type. Therefore, in one exemplary embodiment, a subject active agent that inhibits apoE4 domain interaction ("apoE4 domain interaction inhibitor") may be contained in an enterically coated multiple-unit dosage form. In an exemplary embodiment, the apoE4 domain interaction inhibitor dosage form is prepared by spray-coating granules of an apoE4 domain interaction inhibitor-enteric coating agent solid dispersion on an inert core material. These granules can result in prolonged absorption of the drug with good bioavailability.

Typical enteric coating agents include, but are not limited to, hydroxypropylmethylcellulose phthalate, methacryclic acid-methacrylic acid ester copolymer, polyvinyl acetate-phthalate and cellulose acetate phthalate. Akihiko Hasegawa, *Application of solid dispersions of Nifedipine with enteric coating agent to prepare a sustained-release dosage form*, Chem. Pharm. Bull. 33: 1615-1619 (1985). Various enteric coating materials may be selected on the basis of testing to achieve an enteric coated dosage form designed ab initio to have an optimal combination of dissolution time, coating thicknesses and diametral crushing strength. S. C. Porter et al., *The Properties of Enteric Tablet Coatings Made From Polyvinyl Acetate-phthalate and Cellulose acetate Phthalate*, J. Pharm. Pharmacol. 22:42 p (1970).

Another type of useful oral controlled release structure is a solid dispersion. A solid dispersion may be defined as a dispersion of one or more active ingredients in an inert carrier or matrix in the solid state prepared by the melting (fusion), solvent, or melting-solvent method. Akihiko Hasegawa, *Super Saturation Mechanism of Drugs from Solid Dispersions with Enteric Coating Agents*, Chem. Pharm. Bull. 36: 4941-4950 (1998). The solid dispersions may be also called solid-state dispersions. The term "coprecipitates" may also be used to refer to those preparations obtained by the solvent methods.

The selection of the carrier may have an influence on the dissolution characteristics of the dispersed drug (e.g., apoE4 domain interaction inhibitor) because the dissolution rate of a component from a surface may be affected by other components in a multiple component mixture. For example, a water-soluble carrier may result in a fast release of the drug from the matrix, or a poorly soluble or insoluble carrier may lead to a slower release of the drug from the matrix. The solubility of the apoE4 domain interaction inhibitor may also be increased owing to some interaction with the carriers.

Examples of carriers useful in solid dispersions include, but are not limited to, water-soluble polymers such as polyethylene glycol, polyvinylpyraolidone, and hydroxypropylmethyl—cellulose. Alternative carriers include phosphatidylcholine. Phosphatidylcholine is an amphoteric but water-insoluble lipid, which may improve the solubility of otherwise insoluble apoE4 domain interaction inhibitors in an amorphous state in phosphatidylcholine solid dispersions.

Other carriers include polyoxyethylene hydrogenated castor oil. Poorly water-soluble apoE4 domain interaction inhibitors may be included in a solid dispersion system with an enteric polymer such as hydroxypropylmethylcellulose phthalate and carboxymethylethylcellulose, and a non-enteric polymer, hydroxypropylmethylcellulose. Another solid dispersion dosage form includes incorporation of the drug of interest (e.g., a subject apoE4 domain interaction inhibitor) with ethyl cellulose and stearic acid in different ratios.

There are various methods commonly known for preparing solid dispersions. These include, but are not limited to, the melting method, the solvent method and the melting-solvent method.

Another controlled release dosage form is a complex between an ion exchange resin and the subject apoE4 domain interaction inhibitor. Ion exchange resin-drug complexes have been used to formulate sustained-release products of acidic and basic drugs. In one exemplary embodiment, a polymeric film coating is provided to the ion exchange resin-drug complex particles, making drug release from these particles diffusion controlled. See Y. Raghunathan et al., *Sustained-released drug delivery system I: Coded ion-exchange resin systems for phenylpropanolamine and other drugs*, J. Pharm. Sciences 70: 379-384 (1981).

Injectable microspheres are another controlled release dosage form. Injectable micro spheres may be prepared by non-aqueous phase separation techniques, and spray-drying techniques. Microspheres may be prepared using polylactic acid or copoly(lactic/glycolic acid). Shigeyuki Takada, *Utilization of an Amorphous Form of a Water-Soluble GPIIb/IIIa Antagonist for Controlled Release From Biodegradable Micro spheres*, Pharm. Res. 14:1146-1150 (1997), and ethyl cellulose, Yoshiyuki Koida, *Studies on Dissolution Mechanism of Drugs from Ethyl Cellulose Microcapsules*, Chem. Pharm. Bull. 35:1538-1545 (1987).

Other controlled release technologies that may be used include, but are not limited to, SODAS (Spheroidal Oral Drug Absorption System), INDAS (Insoluble Drug Absorption System), IPDAS (Intestinal Protective Drug Absorption System), MODAS (Multiporous Oral Drug Absorption System), EFVAS (Effervescent Drug Absorption System), PRODAS (Programmable Oral Drug Absorption System), and DUREDAS (Dual Release Drug Absorption System) available from Elan Pharmaceutical Technologies. SODAS are multi particulate dosage forms utilizing controlled release beads. INDAS are a family of drug delivery technologies designed to increase the solubility of poorly soluble drugs. IPDAS are multi particulate tablet formation utilizing a combination of high density controlled release beads and an immediate release granulate. MODAS are controlled release single unit dosage forms. Each tablet consists of an inner core surrounded by a semipermeable multiparous membrane that controls the rate of drug release. EFVAS is an effervescent drug absorption system. PRODAS is a family of multi particulate formulations utilizing combinations of immediate release and controlled release mini-tablets. DUREDAS is a bilayer tablet formulation providing dual release rates within the one dosage form. Although these dosage forms are known to one of skill, certain of these dosage forms will now be discussed in more detail.

INDAS was developed specifically to improve the solubility and absorption characteristics of poorly water soluble drugs. Solubility and, in particular, dissolution within the fluids of the gastrointestinal tract is a key factor in determining the overall oral bioavailability of poorly water soluble drug. By enhancing solubility, one can increase the overall bioavailability of a drug with resulting reductions in dosage. INDAS takes the form of a high energy matrix tablet, production of which is comprised of two distinct steps: the adensosine analog in question is converted to an amorphous form through a combination of energy, excipients, and unique processing procedures.

Once converted to the desirable physical form, the resultant high energy complex may be stabilized by an absorption process that utilizes a novel polymer cross-linked technology to prevent recrystallization. The combination of the change in the physical state of the subject apoE4 domain interaction inhibitor coupled with the solubilizing characteristics of the excipients employed enhances the solubility of the subject apoE4 domain interaction inhibitor. The resulting absorbed amorphous drug complex granulate may be formulated with a gel-forming erodible tablet system to promote substantially smooth and continuous absorption.

IPDAS is a multi-particulate tablet technology that may enhance the gastrointestinal tolerability of potential irritant and ulcerogenic drugs. Intestinal protection is facilitated by the multi-particulate nature of the IPDAS formulation which promotes dispersion of an irritant lipoate throughout the gastrointestinal tract. Controlled release characteristics of the individual beads may avoid high concentration of drug being both released locally and absorbed systemically. The combination of both approaches serves to minimize the potential harm of the subject apoE4 domain interaction inhibitor with resultant benefits to patients.

IPDAS is composed of numerous-high density controlled release beads. Each bead may be manufactured by a two step process that involves the initial production of a micromatrix with embedded apoE4 domain interaction inhibitor and the subsequent coating of this micromatrix with polymer solutions that form a rate-limiting semipermeable membrane in vivo. Once an IPDAS tablet is ingested, it may disintegrate and liberate the beads in the stomach. These beads may subsequently pass into the duodenum and along the gastrointestinal tract, e.g., in a controlled and gradual manner, independent of the feeding state. Release of the apoE4 domain interaction inhibitor occurs by diffusion process through the micromatrix and subsequently through the pores in the rate controlling semipermeable membrane. The release rate from the IPDAS tablet may be customized to deliver a drug-specific absorption profile associated with optimized clinical benefit. Should a fast onset of activity be necessary, immediate release granulate may be included in the tablet. The tablet may be broken prior to administration, without substantially compromising drug release, if a reduced dose is required for individual titration.

MODAS is a drug delivery system that may be used to control the absorption of water soluble agents. Physically MODAS is a non-disintegrating table formulation that manipulates drug release by a process of rate limiting diffusion by a semipermeable membrane formed in vivo. The diffusion process essentially dictates the rate of presentation of drug to the gastrointestinal fluids, such that the uptake into the body is controlled. Because of the minimal use of excipients, MODAS can readily accommodate small dosage size forms. Each MODAS tablet begins as a core containing active drug plus excipients. This core is coated with a solution of insoluble polymers and soluble excipients. Once the tablet is ingested, the fluid of the gastrointestinal tract may dissolve the soluble excipients in the outer coating leaving substantially the insoluble polymer. What results is a network of tiny, narrow channels connecting fluid from the gastrointestinal tract to the inner drug core of water soluble drug. This fluid passes through these channels, into the core, dissolving the drug, and the resultant solution of drug may diffuse out in a controlled manner. This may permit both controlled dissolution and absorption. An advantage of this system is that the drug releasing pores of the tablet are distributed over substantially the entire surface of the tablet. This facilitates uniform drug absorption reduces aggressive unidirectional drug delivery. MODAS represents a very flexible dosage form in that both the inner core and the outer semipermeable membrane may be altered to suit the individual delivery requirements of a drug. In particular, the addition of excipients to the inner core may help to produce a microenvironment within the tablet that facilitates more predictable release and absorption rates. The addition of an immediate release outer coating may allow for development of combination products.

Additionally, PRODAS may be used to deliver a subject apoE4 domain interaction inhibitor. PRODAS is a multi particulate drug delivery technology based on the production of controlled release mini tablets in the size range of 1.5 to 4 mm in diameter. The PRODAS technology is a hybrid of multi particulate and hydrophilic matrix tablet approaches, and may incorporate, in one dosage form, the benefits of both these drug delivery systems.

In its most basic form, PRODAS involves the direct compression of an immediate release granulate to produce individual mini tablets that contain a subject apoE4 domain interaction inhibitor. These mini tablets are subsequently incorporated into hard gels and capsules that represent the final dosage form. A more beneficial use of this technology is in the production of controlled release formulations. In this case, the incorporation of various polymer combinations within the granulate may delay the release rate of drugs from each of the individual mini tablets. These mini tablets may subsequently be coated with controlled release polymer solutions to provide additional delayed release properties. The additional coating may be necessary in the case of highly water soluble drugs or drugs that are perhaps gastroirritants where release can be delayed until the formulation reaches more distal regions of the gastrointestinal tract. One value of PRODAS technology lies in the inherent flexibility to formulation whereby combinations of mini tablets, each with different release rates, are incorporated into one dosage form. As well as potentially permitting controlled absorption over a specific period, this also may permit targeted delivery of drug to specific sites of absorption throughout the gastrointestinal tract. Combination products also may be possible using mini tablets formulated with different active ingredients.

DUREDAS is a bilayer tableting technology that may be used to formulate a subject apoE4 domain interaction inhibitor. DUREDAS was developed to provide for two different release rates, or dual release of a drug from one dosage form. The term bilayer refers to two separate direct compression events that take place during the tableting process. In an exemplary embodiment, an immediate release granulate is first compressed, being followed by the addition of a controlled release element which is then compressed onto this initial tablet. This may give rise to the characteristic bilayer seen in the final dosage form.

The controlled release properties may be provided by a combination of hydrophilic polymers. In certain cases, a rapid release of the subject apoE4 domain interaction inhibitor may be desirable in order to facilitate a fast onset of therapeutic affect. Hence one layer of the tablet may be formulated as an immediate release granulate. By contrast, the second layer of the tablet may release the drug in a controlled manner, e.g., through the use of hydrophilic polymers. This controlled release may result from a combination of diffusion and erosion through the hydrophilic polymer matrix.

A further extension of DUREDAS technology is the production of controlled release combination dosage forms. In this instance, two different subject apoE4 domain interaction inhibitor compounds may be incorporated into the bilayer tablet and the release of drug from each layer controlled to maximize therapeutic affect of the combination.

A subject apoE4 domain interaction inhibitor can be incorporated into any one of the aforementioned controlled released dosage forms, or other conventional dosage forms. The amount of subject apoE4 domain interaction inhibitor contained in each dose can be adjusted, to meet the needs of the individual patient, and the indication. One of skill in the art and reading this disclosure will readily recognize how to adjust the level of subject apoE4 domain interaction inhibitor and the release rates in a controlled release formulation, in order to optimize delivery of subject apoE4 domain interaction inhibitor and its bioavailability.

Inhalational Formulations

A subject apoE4 domain interaction inhibitor will in some embodiments be administered to a patient by means of a pharmaceutical delivery system for the inhalation route. The subject apoE4 domain interaction inhibitor may be formulated in a form suitable for administration by inhalation. The inhalational route of administration provides the advantage that the inhaled drug can bypass the blood-brain barrier. The pharmaceutical delivery system is one that is suitable for respiratory therapy by delivery of a subject apoE4 domain interaction inhibitor to mucosal linings of the bronchi. This invention can utilize a system that depends on the power of a compressed gas to expel the subject apoE4 domain interaction inhibitor from a container. An aerosol or pressurized package can be employed for this purpose.

As used herein, the term "aerosol" is used in its conventional sense as referring to very fine liquid or solid particles carries by a propellant gas under pressure to a site of therapeutic application. When a pharmaceutical aerosol is employed in this invention, the aerosol contains the therapeutically active compound (e.g., a subject apoE4 domain interaction inhibitor), which can be dissolved, suspended, or emulsified in a mixture of a fluid carrier and a propellant. The aerosol can be in the form of a solution, suspension, emulsion, powder, or semi-solid preparation. Aerosols employed in the present invention are intended for administration as fine, solid particles or as liquid mists via the respiratory tract of a patient. Various types of propellants known to one of skill in the art can be utilized. Suitable propellants include, but are not limited to, hydrocarbons or other suitable gas. In the case of the pressurized aerosol, the dosage unit may be determined by providing a value to deliver a metered amount.

A subject apoE4 domain interaction inhibitor can also be formulated for delivery with a nebulizer, which is an instrument that generates very fine liquid particles of substantially uniform size in a gas. For example, a liquid containing the subject apoE4 domain interaction inhibitor is dispersed as droplets. The small droplets can be carried by a current of air through an outlet tube of the nebulizer. The resulting mist penetrates into the respiratory tract of the patient.

A powder composition containing a subject apoE4 domain interaction inhibitor, with or without a lubricant, carrier, or propellant, can be administered to a mammal in need of therapy: This embodiment of the invention can be carried out with a conventional device for administering a powder pharmaceutical composition by inhalation. For example, a powder mixture of the compound and a suitable powder base such as lactose or starch may be presented in unit dosage form in for example capsular or cartridges, e.g. gelatin, or blister packs, from which the powder may be administered with the aid of an inhaler.

There are several different types of inhalation methodologies which can be employed in connection with the present invention. A subject apoE4 domain interaction inhibitor can be formulated in basically three different types of formulations for inhalation. First, a subject apoE4 domain interaction inhibitor can be formulated with low boiling point propellants. Such formulations are generally administered by conventional meter dose inhalers (MDI's). However, conventional MDI's can be modified so as to increase the ability to obtain repeatable dosing by utilizing technology which measures the inspiratory volume and flow rate of the patient as discussed within U.S. Pat. Nos. 5,404,871 and 5,542,410.

Alternatively, a subject apoE4 domain interaction inhibitor can be formulated in aqueous or ethanolic solutions and delivered by conventional nebulizers. In some embodiments, such solution formulations are aerosolized using devices and systems such as disclosed within U.S. Pat. Nos. 5,497,763; 5,544,646; 5,718,222; and 5,660,166.

Lastly, a subject apoE4 domain interaction inhibitor can be formulated into dry powder formulations. Such formulations can be administered by simply inhaling the dry powder formulation after creating an aerosol mist of the powder. Technology for carrying such out is described within U.S. Pat. No. 5,775,320 issued Jul. 7, 1998 and U.S. Pat. No. 5,740,794 issued Apr. 21, 1998.

With respect to each of the patents recited above, applicants point out that these patents cite other publications in intrapulmonary drug delivery and such publications can be referred to for specific methodology, devices and formulations which could be used in connection with the delivery of a subject apoE4 domain interaction inhibitor. Further, each of the patents are incorporated herein by reference in their entirety for purposes of disclosing formulations, devices, packaging and methodology for the delivery of subject apoE4 domain interaction inhibitor formulations.

The present invention further provides a package for use in treating an apoE4-associated disorder. A subject package comprises a container having therein a flowable formulation suitable for delivery by inhalation, the formulation comprising a pharmaceutically active apoE4 domain interaction inhibitor in an amount sufficient to treat the apoE4-associated disorder. In some embodiments, the package is a metered dose inhaler, and the apoE4 domain interaction inhibitor is formulated with a propellant. Where the package produces an aerosol formulation, particles having a diameter of about 0.5 to 12 microns are generated when the formulation is aerosolized. In some embodiments, the package is a dry powder inhaler, and the apoE4 domain interaction inhibitor is formulated in a dry powder formulation. In other embodiments, the package is a nebulizer, and the apoE4 domain interaction inhibitor is in an aqueous or ethanolic solution.

Dosages

Although the dosage used will vary depending on the clinical goals to be achieved, a suitable dosage range is one which provides up to about 1 µg to about 1,000 µg or about 10,000 µg of an agent that reduces apoE4 domain interaction and can be administered in a single dose. Alternatively, a target dosage of an agent that reduces apoE4 domain interaction can be considered to be about in the range of about 0.1-1000 µM, about 0.5-500 µM, about 1-100 µM, or about 5-50 µM in a sample of host blood drawn within the first 24-48 hours after administration of the agent.

Those of skill will readily appreciate that dose levels can vary as a function of the specific compound, the severity of the symptoms and the susceptibility of the subject to side effects. Preferred dosages for a given compound are readily determinable by those of skill in the art by a variety of means.

Routes of Administration

An agent that reduces apoE4 domain interaction is administered to an individual using any available method and route suitable for drug delivery, including in vivo and ex vivo methods, as well as systemic and localized routes of administration.

Conventional and pharmaceutically acceptable routes of administration include intranasal, intramuscular, intratracheal, intratumoral, subcutaneous, intradermal, topical application, intravenous, rectal, nasal, oral and other enteral and parenteral routes of administration. Routes of administration may be combined, if desired, or adjusted depending upon the agent and/or the desired effect. The composition can be administered in a single dose or in multiple doses. In some embodiments, the composition is administered orally. In other specific embodiments, the composition is administered via an inhalational route. In some embodiments, the composition is administered intranasally.

The agent can be administered to a host using any available conventional methods and routes suitable for delivery of conventional drugs, including systemic or localized routes. In general, routes of administration contemplated by the invention include, but are not necessarily limited to, enteral, parenteral, or inhalational routes.

Parenteral routes of administration other than inhalation administration include, but are not necessarily limited to, topical, transdermal, subcutaneous, intramuscular, intraorbital, intracapsular, intraspinal, intrastemal, and intravenous routes, i e., any route of administration other than through the alimentary canal. Parenteral administration can be carried to effect systemic or local delivery of the agent. Where systemic delivery is desired, administration typically involves invasive or systemically absorbed topical or mucosal administration of pharmaceutical preparations.

The agent can also be delivered to the subject by enteral administration. Enteral routes of administration include, but are not necessarily limited to, oral and rectal (e.g., using a suppository) delivery.

Methods of administration of the agent through the skin or mucosa include, but are not necessarily limited to, topical application of a suitable pharmaceutical preparation, transdermal transmission, injection and epidermal administration. For transdermal transmission, absorption promoters or iontophoresis are suitable methods. Iontophoretic transmission may be accomplished using commercially available "patches" which deliver their product continuously via electric pulses through unbroken skin for periods of several days or more.

By treatment is meant at least an amelioration of the symptoms associated with the pathological condition afflicting the host, where amelioration is used in a broad sense to refer to at least a reduction in the magnitude of a parameter, e.g. symptom, associated with the pathological condition being treated, such as an apoE4-associated neurological disorder and pain associated therewith. As such, treatment also includes situations where the pathological condition, or at least symptoms associated therewith, are completely inhibited, e.g. prevented from happening, or stopped, e.g. terminated, such that the host no longer suffers from the pathological condition, or at least the symptoms that characterize the pathological condition.

A variety of hosts (wherein the term "host" is used interchangeably herein with the terms "subject" and "patient") are treatable according to the subject methods. Generally such hosts are "mammals" or "mammalian," where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In many embodiments, the hosts will be humans.

Kits with unit doses of the active agent, e.g. in oral or injectable doses, are provided. In such kits, in addition to the containers containing the unit doses will be an informational package insert describing the use and attendant benefits of the drugs in treating pathological condition of interest. Preferred compounds and unit doses are those described herein above.

Methods of Treating apoE4-Associated Neurological Disorders

The invention further provides methods of treating apoE4 neurological disorders. In some embodiments, the invention provides methods for reducing apoE4 domain interaction in a host cell that synthesizes apoE4, comprising administering an effective amount of an agent that reduces apoE4 domain interaction to an individual in need thereof. In other embodiments, the invention provides methods for reducing apoE4 domain interaction in apoE4 that is extracellular, e.g., in the serum, cerebrospinal fluid, or in the interstitial fluid. In some embodiments, an agent that reduces apoE4 domain interaction is one that is effective in increasing neurite outgrowth. In other embodiments, an agent that reduces apoE4 domain interaction is one that results in improved outcome following stroke. In some embodiments, an agent that reduces apoE4 domain interaction is one that is effective in increasing neurite outgrowth. In other embodiments, an agent that reduces apoE4 domain interaction is one that results in improved outcome following traumatic head injury. In other embodiments, an agent that reduces apoE4 domain interaction is one that reduces the risk of developing Alzheimer's disease. In other embodiments, an agent that reduces apoE4 domain interaction is one that reduces a symptom or phenomenon associated with Alzheimer's disease. In some of these embodiments, an agent that reduces apoE4 domain interaction is one that reduces formation of neurofibrillary tangles. In other embodiments, an agent that reduces apoE4 domain interaction is one that, when administered to an individual, results in reduced amyloid deposits in the brain of the individual.

In some embodiments, an agent that reduces apoE4 domain interaction reduces a symptom associated with AD, such as formation of neurofibrillary tangles or Aβ deposits, by at least about 10%, at least about 20%, at least about 30%, at least about 50%, at least about 60%, at least about 70%, at least about 80%, at least about 90% or more. In other embodiments, an agent that reduces apoE4 domain interaction improves a parameter that is in decline in individuals with AD, such as memory or cognitive function, by at least about 10%, at least about 20%, at least about 30%, at least about 50%, at least about 60%, at least about 70%, at least about 80%, at least about 90% or more, such that the decline in one of these parameters is at least slowed.

Neuronal cells may produce apoE4 themselves. Alternatively, or in addition, neuronal cells may take up apoE4 from their environment, e.g., apoE4 produced by supporting cells such as astrocytes and glial cells and secreted into the interstitial fluid.

In some embodiments, the methods of the invention are effective in reducing apoE4 domain interaction in neuronal cells that produce apoE4 and/or that take up apoE4 from their environment, i.e., neuronal cells in which detectable amounts of apoE4 are found. Neuronal cells amenable to treatment using the methods of the invention include those that produce or take up from about 1 ng to about 1000 ng (or more), from about 5 ng to about 500 ng, from about 10 ng to about 100 ng, apoE4 per mg total cell protein in a 48-hour period.

In other embodiments, the invention provides methods for inhibiting formation of neurofibrillary tangles in an individual, comprising administering an effective amount of an agent that reduces apoE4 domain interaction to the individual. Whether formation of neurofibrillary tangles is inhibited can be determined, e.g., in experimental animal models of Alzheimer's disease (AD). Experimental animal models of AD have been described in the art; any known animal model of AD can be used to determine whether an agent of the invention inhibits formation of neurofibrillary tangles. See, e.g., U.S. Pat. No. 6,046,381. Such animal models can also be used to determine whether other phenomena, such as amyloid deposition, and cognitive abilities, are affected by an agent that reduces apoE4 domain interaction. Whether an agent that reduces apoE4 domain interaction reduces formation of neurofibrillary tangles and/or Aβ deposits can also be determined in humans using any known method, including, but not limited to, immunohistochemical staining of brain biopsy samples.

In other embodiments, the invention provides methods for treating AD, comprising administering to an individual an effective amount of an agent that reduces apoE4 domain interaction. Individuals known to be at risk of developing AD are amenable to treatment using the methods of the invention. Thus, an agent that reduces apoE4 domain interaction is suitable for use prophylactically in patients who are heterozygous or homozygous for apoE4 but do not show overt symptoms of Alzheimer's disease or other neurodegenerative disorders. The methods are also useful to treat an individual who already displays symptoms of AD, where the method treats AD by reducing advancement of the disease, or reduces severity of a symptom associated with AD. Whether advancement of AD is reduced or severity of an AD-related symptom is reduced can be determined by assessing any symptom or parameter associated with AD, including, but not limited to, cognitive function, and memory. Such determinations are well within the ability of those skilled in the art using standard methods known in the art.

In some embodiments, an agent that reduces apoE4 domain interaction is one that, when administered to an individual in need thereof, such as a stroke patient or an individual who has undergone traumatic head injury, improves the clinical outcome for that individual. Whether an agent that reduces apoE4 domain interaction results in improved outcome following stroke or traumatic head injury when the agent is administered to an individual who has suffered a stroke or traumatic head injury can be determined using any available animal model of stroke and traumatic head injury. Rodent models of neuronal damage, for example neuronal damage caused by cerebral ischemia, may be examined to determine the effect on an agent that reduces apoE4 domain interaction on the extent of neuronal damage caused by traumatic events as well as their role in neuronal remodeling, repair and recovery from such insults. Rodent models of cerebral ischemia, both global ischemia and focal ischemia, are useful for studying mechanisms controlling the occurrence of cerebral ischemia and potential therapeutic strategies for treatment of injury caused by ischemic events. Animal models of global ischemia, which is usually transient, have widely affected brain areas but typically give rise to neuronal alterations in selectively vulnerable brain regions. Examples of such models include, but are not limited to, the two vessel occlusion model of forebrain ischemia, the four vessel occlusion model of forebrain ischemia, and ischemia models involving elevated cerebrospinal fluid pressure. See, e.g., Ginsberg and Busto, *Stroke*, 20:1627-1642 (1989).

Methods for Treating apoE4-Related Disorders Associated with Hyperlipidemia

The invention further provides methods for treating apoE4-related disorders that are associated with elevated serum lipid levels. The methods generally comprise administering to an individual an effective amount of an agent that reduces apoE4 domain interaction.

In some embodiments, the invention provides methods for reducing serum cholesterol levels, comprising administering an agent that reduces apoE4 domain interaction. In these embodiments, an agent that reduces apoE4 domain interaction reduces serum cholesterol levels in an individual when administered to the individual by at least about 10%, at least about 20%, at least about 30%, at least about 40%, or at least about 50%, compared to a serum cholesterol in an individual not administered with the agent. In general, an effective amount of an agent that reduces apoE4 domain interaction is effective at least in reducing a serum cholesterol level such that it is in a normal range. A normal range of serum cholesterol will vary, depending upon the sex and age of the individual, as well as other factors. For adult humans, a normal range of serum cholesterol is from about 200 to about 240 mg/dL. An "elevated serum cholesterol level" is similarly dependent upon age and sex of the individual. Thus, e.g., an adult human having a serum cholesterol level of over 240 mg/dL is considered to have an elevated serum cholesterol level. In some embodiments, an effective amount of an agent that reduces apoE4 domain interaction is one that is effective in reducing serum cholesterol levels to below 240 mg/dL.

In other embodiments, the invention provides methods of reducing the risk that an individual will develop coronary artery disease (CAD) or atherosclerosis, comprising administering to the individual an effective amount of an agent that reduces apoE4 domain interaction. In these embodiments, an agent that reduces apoE4 domain interaction reduces the risk of developing CAD or atherosclerosis by at least about 10%, at least about 20%, at least about 30%, at least about 40%, or at least about 50% or more, when compared with the risk associated with an individual not treated with the agent.

Individuals who are amenable to treatment with the methods of the invention include those who are known to be at risk for developing CAD because these individuals express apoE4; individuals who express apoE4 and have elevated serum cholesterol levels; and individuals who express apoE4 and have had one or more cardiac events.

Assays to Detect Compounds Affecting Neuronal Cell Growth

Differential expression of different isoforms of apolipoprotein E affects neuronal cell growth. In some embodiments, assays of the invention utilize differential expression of different isoforms of apolipoprotein E in order to determine compounds which affect neuronal cell growth. In other embodiments, assays described herein identify compounds that reduce apoE4 domain interaction. Compounds identified via an assay of the invention are formulated into compositions which are useful in the treatment of neurological diseases—particularly such diseases' where abnormal differential expression of isoforms of apolipoproteins is present. Details regarding theories behind the invention as well as specific examples of the invention are provided below. However, the invention is not limited by such theories or examples.

In neurons, the cytoskeleton functions in neurite extension and retraction. Therefore, the studies described herein and by others (Handelmann (1992); and Nathan et al. (1994) *Science* 264:850-852), have focused on the isoform-specific effects of apoE3 and apoE4 on neurite extension and branching. Different isoforms of apoE modulate the intracellular cytoskeletal apparatus and alter neurite extension and branching. Understanding how the various apoE isoforms alter the cytoskeleton provides information on (1) the process of neurofibrillary tangle formation and (2) control of apoE-induced remodeling of synaptic connections later in life. Compounds which stimulate neurite extension in vivo are likely to promote nerve regeneration or the formation of synaptic connections during neuronal remodeling in both the central and peripheral nervous system.

Specific assays have been developed for screening compounds for their effect on neuronal growth. Further, the assay makes it possible to screen for compounds which affect cell-surface HSPG and thereby effect differential cellular accumulation of apoE3 and apoE4. A comparison of the effects of human apoE3 versus human apoE4 showed pronounced differential isoform-specific effects on neurite outgrowth. Compared to a control, human apoE3 plus β-VLDL resulted in an increase in neurite extension, while apoE4 plus β-VLDL resulted in a marked decrease in both neurite branching and extension. Results presented by Nathan et al. (1995) show that dorsal root ganglion neurons incubated with apoE4 plus β-VLDL displayed very short, stunted neurites. This was not a toxic effect of apoE4 since replacement of the apoE4-containing media with fresh apoE4-lacking media restored the ability of the neurons to produce neuritic extensions. Furthermore, the apoE3- and apoE4-specific effects were blocked by (1) an antibody against the receptor binding domain of apoE or (2) reductive methylation of critical lysine residues, indicating that this effect of apoE is receptor-mediated, or HSPG-mediated.

Neuro-2a cells from the central nervous system were used to compare the effects of apoE on the peripheral nervous system neurons described above with the effect on cortical neurons. Cells of both types respond similarly to apoE. When combined with a source of lipid, apoE3 stimulated neurite extension, whereas apoE4 inhibited neurite extension. Nathan et al. (1994) *Soc. Neurosci.* 20 (Part 2):1033 (Abstr.); and Nathan et al. (1995). Addition of free apoE3 or apoE4 without β-VLDL had no effect on neurite outgrowth. These results indicate that the effect of apoE on neurons requires the lipoprotein receptor-mediated uptake of apoE or a combination of apoE and lipid. Free of lipid, apoE does not bind to either the LDL receptor or the LRP. In contrast, in another study, using a different neuronal cell line, Holtzman et al. demonstrated that apoE3 with β-VLDL stimulated nerve growth factor-induced neurite outgrowth, whereas apoE4 had no effect. Holtzman et al. (1995) *Soc. Neurosci.* 21 (abstr): 1009, 400.10.

To determine whether lower levels of endogenously produced apoE would have an effect on neurite outgrowth from Neuro-2a cells, in the examples provided below, the neuronal cells were transfected with human apoE cDNA constructs encoding apoE3 or apoE4. Clones of the transfected cells secreting equal amounts of apoE3 or apoE4 (~50-60 ng of apoE/mg of cell protein/48 hours) were selected for comparison. The apoE3- and apoE4-secreting cells grown in serum-free control medium displayed a similar degree of limited neurite extension. However, when a source of lipid (β-VLDL) was added to the medium, the cells had a markedly different growth pattern. The apoE3-secreting cells showed greater neurite extension than did the apoE4-secreting cells. Thus, even very low levels of endogenously produced apoE along with a source of lipid revealed the differential effects of apoE3 versus apoE4. Lipid emulsions of various compositions, as well as cerebrospinal fluid lipoproteins can be substituted for the β-VLDL and appear to serve as a source of lipid for the cells or as a vehicle for transporting the apoE into a specific intracellular pathway. The examples presented herein show that the apoE effect on neurite outgrowth is mediated through the LRP, or a similar apoE-binding receptor, and that blocking or effectively preventing this interaction inhibits the apoE4 induced inhibition of neurite outgrowth.

Thus, the invention relates to assaying compounds for their ability to reduce the apoE4-induced inhibition of neuron remodeling by inhibiting the interaction of apoE4 and an apoE-binding receptor, e.g., the LRP. Compounds found via the assay might alter the function of apoE4 by changing the domain interaction to interfere with the inhibition of apoE4 in neuron remodeling. Any agent that blocks the interaction of arginine-61 with glutamic acid-255 in apoE4 could be screened for in the assay. Blocking domain interaction in apoE4 converts apoE4 to an "apoE3-like" molecule, thereby blunting the undesirable effects of apoE4 on neurite extension. This may also have the effect of switching the apoE4 binding preference from VLDL to HDL.

Assays can screen for compounds with any effect on neurite growth, but the compounds screened for reduce apoE4 inhibition of neurite outgrowth by at least about 10%, at least about 50%, at least about 75%, or at least about 90%. The effect on neurite outgrowth can be measured, for instance, by the methods described herein.

Assays of the invention can be used to screen for compounds which prevent apoE4 from interacting effectively with neuronal LRP or other apoE-binding receptors. This prevention can be directed at either the HSPG and/or the LRP interactions or by modifying its function to be more apoE3-like and can directly or indirectly block binding or otherwise prevent the signal transduction induced by apoE4 binding. Thus, assays screen for compounds which prevent inhibition of neurite outgrowth by any of these routes. Thus, the invention comprises whole proteins, any functional portion thereof, analog or homologue which prevent effective interaction of apoE4 and HSPG or LRP, or other apoE-binding receptors. For instance, changes in the amino acid sequences of the RAP or lactoferrin and other known ligands of the LRP, or other apoE-binding receptors, that do not substantially affect their ability to effectively block the interaction of apoE4 and the LRP are compounds to be screened for.

The invention also encompasses methods for detecting therapeutic agents that reduce the interaction of apoE4 and the LRP and other members of the LDL receptor family. The methods include in vitro ligand blotting techniques. This can be performed following the separation of cell membrane proteins (which contain the LRP) or the LRP partially purified from membrane proteins for instance by nonreducing sodium dodecylsulfate-polyacrylamide gel electrophoresis and transfer to a nitrocellulose membrane. Methods of partial purification of the LRP are described, for instance, by Schneider et al. (1985) *Methods Enzymol.* 109:405-417. The membrane is then incubated with apoE and a lipoprotein (e.g. β-VLDL) which is labeled, for instance by biotinylation. Binding of the apoE-β-VLDL complex to the membrane is then visualized using reagents that detect the label. Agents to be tested for their ability to block the interaction are added to the nitrocellulose together with apoE and β-VLDL to determine if the interaction is blocked.

FRET-Based Assays

The present invention further provides an in vitro cell-based assay that identifies compounds that inhibit apoE4 domain interaction, where the apoE4 is extracellular and/or intracellular. The instant method provides for detection of disruption of apoE4 domain interaction intracellularly and extracellularly (in the culture medium) in a single sample.

FRET involves the transfer of energy from a donor fluorophore in an excited state to a nearby acceptor fluorophore. For this transfer to take place, the donor and acceptor molecules must in close proximity (e.g., less than 10 nanometers apart, usually between 10 and 100 Å apart), and the emission spectra of the donor fluorophore must overlap the excitation spectra of the acceptor fluorophore.

Figure 30:
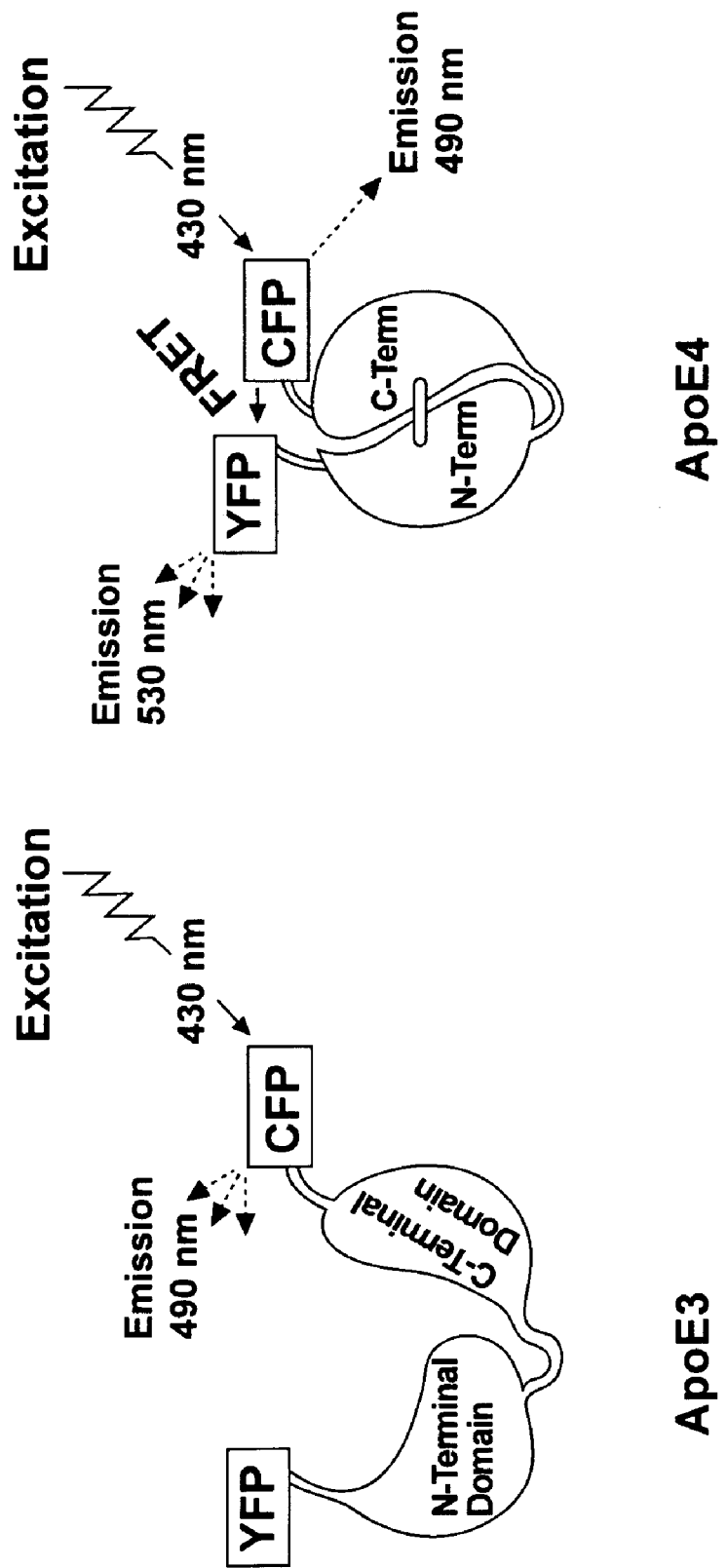
FIG. 30 is a schematic representation of the use of FRET to image apoE4 domain interaction in living Neuro-2a cells.

In the instant assay, as shown schematically in FIG. 30, a donor fluorophore is attached at or near the C-terminal domain of apoE4; and an acceptor fluorophore is attached at or near the N-terminal domain of apoE4. Alternatively, a donor fluorophore is attached at or near the N-terminal domain of apoE4; and an acceptor fluorophore is attached at or near the C-terminal domain of apoE4. In the absence of an apoE4 domain interaction inhibitor, FRET occurs, wherein emission resulting from excitation of the donor fluorophore excites the acceptor fluorophore, resulting in emission of fluorescence from the acceptor fluorophore. A test compound that is a candidate apoE4 domain interaction inhibitor of interest reduces emission from the acceptor fluorophore by at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, or more, compared to the level of emission from the acceptor fluorophore in the absence of the test compound. An inhibitor of interest is one that does not have a significant effect on viability of the test cells, e.g., an inhibitor of interest reduce viability of the test cells by less than about 15%, less than about 10%, less than about 5%, less than about 2%, or less than about 1%.

A subject method generally involves contacting a test cell in vitro with a test agent; and determining the effect, if any, of the test agent on apoE4 domain interaction, where the apoE4 polypeptide is intracellular and/or extracellular (in the culture medium). The test cell is one that produces an apoE4 polypeptide that comprises a fluorescence donor and a fluorescence acceptor, wherein the fluorescence donor and the fluorescence acceptor are attached to the apoE4 polypeptide in such a way that, in the absence of an inhibitor of apoE4 domain interaction, FRET occurs. In many embodiments, the test cell is one that has been genetically modified with an expression vector comprising a nucleotide sequence encoding apoE4 tagged with a fluorescence donor and a fluorescence acceptor. For example, in many embodiments, the test cell is one that has been genetically modified with an expression vector comprising a nucleotide sequence encoding, in order from N-terminus to C-terminus, a fluorescence acceptor polypeptide; apoE4; and a fluorescence donor polypeptide. Alternatively, the test cell is one that has been genetically modified with an expression vector comprising a nucleotide sequence encoding, in order from N-terminus to C-terminus, a fluorescence donor polypeptide; apoE4; and a fluorescence acceptor polypeptide. In other embodiments, a test cell is one into which an apoE4 polypeptide tagged with fluorescence acceptor and donor dyes has been introduced, such that the fluorescently tagged apoE4 polypeptide is present in the cytoplasm of the cell.

An inhibitor of interest is one that does not have a significant effect on FRET of a fluorescently tagged apoE3 polypeptide. For example, an inhibitor of interest reduces FRET by less than about less than about 20%, less than about 15%, less than about 10%, less than 5%, less than about 2%, or less, of a fluorescently tagged apoE3 polypeptide. Thus, e.g., an apoE3 polypeptide that comprises a fluorescence donor at or near the N-terminus and a fluorescence acceptor at or near the C terminus, serves as a control for specificity of the inhibitor for apoE4. Alternatively, the fluorescently tagged apoE3 control polypeptide comprises a fluorescence donor at or near the C-terminus and a fluorescence acceptor at or near the N-terminus. A control cell will thus in some embodiments produce a fluorescently tagged apoE3 polypeptide. The control cell will in many embodiments be the same cell type (e.g., the same cell line) as the test cell, but will be genetically modified with an expression vector that comprises a nucleotide sequence encoding a fluorescently tagged apoE3 polypeptide. For example, in many embodiments, a control cell is one that has been genetically modified with an expression vector comprising a nucleotide sequence encoding, in order from N-terminus to C-terminus, a fluorescence acceptor polypeptide; apoE3; and a fluorescence donor polypeptide. Alternatively, the control cell is one that has been genetically modified with an expression vector comprising a nucleotide sequence encoding, in order from N-terminus to C-terminus, a fluorescence donor polypeptide; apoE3; and a fluorescence acceptor polypeptide. In other embodiments, a test cell is one into which an apoE3 polypeptide tagged with fluorescence acceptor and donor dyes has been introduced, such that the fluorescently tagged apoE3 polypeptide is present in the cytoplasm of the cell.

Suitable acceptors and donors include fluorescent proteins or dyes, e.g., a fluorescent protein as described in Matz et al., Nature Biotechnology (October 1999) 17:969-973, a green fluorescent protein from *Aequoria Victoria* or fluorescent mutant thereof, e.g., as described in U.S. Pat. Nos. 6,066,476; 6,020,192; 5,985,577; 5,976,796; 5,968,750; 5,968,738; 5,958,713; 5,919,445; 5,874,304, the disclosures of which are herein incorporated by reference; a yellow fluorescent protein; other fluorescent dyes, e.g., coumarin and its derivatives, e.g. 7-amino-4-methylcoumarin, aminocoumarin, bodipy dyes, such as Bodipy FL, cascade blue, fluorescein and its derivatives, e.g. fluorescein isothiocyanate, Oregon green, rhodamine dyes, e.g. texas red, tetramethylrhodamine, eosins and erythrosins, cyanine dyes, e.g. Cy3 and Cy5, macrocyclic chelates of lanthanide ions, e.g. quantum dye, etc., chemilumescent dyes, e.g., luciferases, including those described in U.S. Pat. Nos. 5,843,746; 5,700,673; 5,674,713; 5,618,722; 5,418,155; 5,330,906; 5,229,285; 5,221,623; 5,182,202; the disclosures of which are herein incorporated by reference. Selection of an appropriate fluorescence donor and fluorescence acceptor is well within the skill level of those of ordinary skill in the art.

The instant assay is a cell-based assay. Any of a wide variety of cells are suitable for use in a subject assay. The cells are generally eukaryotic cells, e.g., cells that grow as unicellular entities in vitro under standard culture conditions. Non-limiting examples of suitable cells include Neuro-2a cells, CHO cells, COS cells, yeast cells (e.g., *Saccharomyces cerevisiae, Picchia*, etc.), and the like.

Test cells in the presence or absence of a test agent are analyzed for fluorescence emission, e.g., a FRET signal is detected. The FRET signal is calculated as the ration of fluorescence acceptor to fluorescence donor fluorescence intensity following excitation of the fluorescence donor. The FRET signal in the culture medium of the test cell, and the FRET signal in the test cell, can be measured in a single sample. An MTT assay can also be conducted in the same sample of test cells, to determine the effect, if any, of the test compound on viability of the test cells.

The present assay is suitable for high through-put format. For example, the test cells, in a suitable culture medium, are placed in wells of a multi-well plate (e.g., 96-well, a 192-well plate, a 384-well plate, and the like).

The terms "candidate agent," "test agent," "agent", "substance" and "compound" are used interchangeably herein. Candidate agents encompass numerous chemical classes, typically synthetic, semi-synthetic, or naturally-occurring inorganic or organic molecules. Candidate agents include those found in large libraries of synthetic or natural compounds. For example, synthetic compound libraries are commercially available from Maybridge Chemical Co. (Trevillet, Cornwall, UK), ComGenex (South San Francisco, Calif.), and MicroSource (New Milford, Conn.). A rare chemical library is available from Aldrich (Milwaukee, Wis.). Alternatively, libraries of natural compounds in the form of bacterial, fungal, plant and animal extracts are available from Pan Labs (Bothell, Wash.) or are readily producible.

Candidate agents may be small organic or inorganic compounds having a molecular weight of more than 50 and less than about 2,500 daltons. Candidate agents may comprise functional groups necessary for structural interaction with proteins, particularly hydrogen bonding, and may include at least an amine, carbonyl, hydroxyl or carboxyl group, and may contain at least two of the functional chemical groups.

The candidate agents may comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Assays of the invention include controls, where suitable controls include a sample (e.g., a sample comprising the test cell) in the absence of the test agent. Generally a plurality of assay mixtures is run in parallel with different agent concentrations to obtain a differential response to the various concentrations. Typically, one of these concentrations serves as a negative control, i.e. at zero concentration or below the level of detection.

Neurological Disorders

Compounds found via an assay described herein are formulated to provide therapeutics for patients suffering from a wide range of disorders. For instance, patients suffering from neurodegeneration or hypoxia may be treated. Neurodegeneration may result from a number of causes, including, but not limited to, Alzheimer's disease, trauma, viral infections, genetic enzyme deficiencies, age-related cognitive decline, and prion diseases. Viruses which may cause neurodegeneration include, but are not limited to, human immunodeficiency virus (HIV) and Epstein-Barr virus. Genetic enzyme deficiencies which may cause neurodegeneration include, but are not limited to, deficiency in P-N-acetylhexosaminidase which causes Tay-Sachs disease. Age-related cognitive decline is described, for instance, in *Diagnostic and Statistical Manual of Mental Disorders*, Fourth ed., Washington D.C. American Psychiatric Association (1994). Prion diseases include, but are not limited to, Kuru and Creutzfeldt-Jacob disease. Hypoxia is generally the result of stroke or is temporary and associated for instance with drowning, airway obstructions or carbon monoxide poisoning.

Neuron remodeling is also important in otherwise healthy patients. Therefore, compounds identified by the assay may be suitable for use prophylactically in patients who are heterozygous or homozygous for apoE4 but do not show overt symptoms of Alzheimer's disease or other neurodegenerative disorders.

The neurite outgrowth assay of the invention has been used to identify potential therapeutics including glycoprotein such as RAP, heparinases, and lactoferrin all of which reduce or abolish apoE4-induced inhibition of neurite outgrowth. Assays of the present invention can identify compounds that bind specifically to apoE4 and prevent its domain interaction, e.g., small molecules and antibodies. Agents that disrupt the domain interaction can be selected from a wide variety of molecules, including, but not limited to, small molecules, glycoproteins, peptides and antibodies which are designed to bind to arginine-61 or glutamic acid-255 of apoE4. Specific assays for screening for agents that disrupt this domain interaction is described in Example 3 and Example 7, below. Assays of the invention include those that determine whether apoE4 exhibits apoE3 activity.

Heparinases or other modifiers of HSPG are effective in vitro in ameliorating the effects of apoE4 on neuron remodeling. However, their pleiotropic effects render them unsuitable for human therapy. Assays of the invention can be used to identify potentially effective therapeutic agents such as HSPG analogs which bind to apoE4 to prevent its binding to neurons but do not exert substantial pleiotropic effects., The RAP is a glycoprotein with an apparent molecular mass of 39-kD in humans. The RAP specifically associates with gp330 and the LRP, both of which are members of the LDL receptor gene family. Various RAPs and homologs thereof have been described and their functional domains have been mapped. For review see, Orlando et al. (1994) *Proc. Natl. Acad. Sci. USA* 91:3161-3165; and Warshawsky et al. (1995) *Biochem.* 34:3404-3415. The RAP, and portions thereof, are known to block the binding of the LRP to its ligand t-PA and $I_2$-macroglobulin-protease complexes. Warshawsky et al. (1994) *Ann. N.Y. Acad. Sci.* pp. 514-517.

Lactoferrin

Lactoferrin has been shown to bind to the LRP, gp330, and HSPG. Willnow et al. (1994) *J. Biol. Chem.* 267:26172-26180;, Mahley et al. (1994) *Ann. N.Y. Acad. Sci. USA* 737: 39-52; and Ji et al. (1994a) *Arterioscler. Thromb.* 14:2025-2032. Lactoferrin appears to be cleared from the bloodstream by binding with LRP. Meilinger et al. (1995). Lactoferrin blocks binding of ligands to both the LRP and HSPG and blocks the HSPG-LRP pathway. This apparently occurs through the interaction of a region of concentrated positive charge on the lactoferrin with negatively-charged groups on the HSPG and negatively-charged amino acids in the ligand binding domain of the LRP.

Antibodies

Antibodies specific for apoE block the apoE4 induced inhibition of neuron remodeling. Assays of the invention can be used to screen antibodies to either apoE4 or the LRP to determine the potential utility therapeutically. The assay can screen antibodies to find those that inhibit the neuron remodeling inhibitory effect of apoE4 whether by inhibiting binding to the LRP or by altering the function of apoE4 to become more apoE3-like. Preferred antibodies are monoclonal and specific for the apoE4 isoform and not apoE3 or apoE2. The term "antibody" also includes functional portions and equivalents thereof. For instance, antibodies include any monospecific compound comprised of a sufficient portion of the light chain variable region to effect binding to the epitope to which the whole antibody has binding specificity. The fragments may include the variable region of at least one heavy or light chain immunoglobulin peptide, and include, but are not limited to, Fab fragments, Fab2 fragments, and Fv fragments. In addition, the monospecific domains of antibodies can be produced by recombinant engineering. Such recombinant molecules include, but are not limited to, fragments produced in bacteria, and murine antibodies in which the majority of the murine constant regions have been replaced with human antibody constant regions.

Delivery of Therapeutic Agents

After an assay of the invention has shown that a compound has certain characteristics as a potential therapeutic it is within the skill of one in the art to determine whether the compound has in vivo therapeutic utility. It is also within the skill of one in the art to formulate suitable dosage formats for delivery of the therapeutic agents. When the site of delivery is the brain, the therapeutic agent must be capable of being delivered to the brain.

The blood-brain barrier limits the uptake of many therapeutic agents into the brain and spinal cord from the general circulation. Molecules which cross the blood-brain barrier use two main mechanisms: free diffusion; and facilitated transport. Because of the presence of the blood-brain barrier, attaining beneficial concentrations of a given therapeutic agent in the CNS may require the use of drug delivery strategies. Delivery of therapeutic agents to the CNS can be achieved by several methods.

One method relies on neurosurgical techniques. In the case of gravely ill patients such as accident victims or those suffering from various forms of dementia, surgical intervention is warranted despite its attendant risks. For instance, therapeutic agents can be delivered by direct physical introduction into the CNS, such as intraventricular or intrathecal injection of drugs. Intraventricular injection may be facilitated by an intraventricular catheter, for example, attached to a reservoir, such as an Ommaya reservoir. Methods of introduction may also be provided by rechargeable or biodegradable devices. Another approach is the disruption of the blood-brain barrier by substances which increase the permeability of the blood-brain barrier. Examples include intra-arterial infusion of poorly diffusible agents such as mannitol, pharmaceuticals which increase cerebrovascular permeability such as etoposide, or vasoactive agents such as leukotrienes. Neuwelt and Rappoport (1984) *Fed. Proc.* 43:214-219; Baba et al. (1991) *J. Cereb. Blood Flow Metab.* 11:638-643; and Gennuso et al. (1993) *Cancer Invest.* 11:638-643.

Further, it may be desirable to administer the pharmaceutical agents locally to the area in need of treatment; this may be achieved by, for example, local infusion during surgery, by injection, by means of a catheter, or by means of an implant, said implant being of a porous, non-porous, or gelatinous material, including membranes, such as silastic membranes, or fibers.

Therapeutic compounds can also be delivered by using pharmacological techniques including chemical modification or screening for an analog which will cross the blood-brain barrier. The compound may be modified to increase the hydrophobicity of the molecule, decrease net charge or molecular weight of the molecule, or modify the molecule, so that it will resemble one normally transported across the blood-brain barrier. Levin (1980) *J. Med. Chem.* 23:682-684; Pardridge (1991) in: *Peptide Drug Delivery to the Brain*; and Kostis et al. (1994) *J. Clin. Pharmacol.* 34:989-996.

Encapsulation of the drug in a hydrophobic environment such as liposomes is also effective in delivering drugs to the CNS. For example WO 91/04014 describes a liposomal delivery system in which the drug is encapsulated within liposomes to which molecules have been added that are normally transported across the blood-brain barrier.

Another method of formulating the drug to pass through the blood-brain barrier is to encapsulate the drug in a cyclodextrin. Any suitable cyclodextrin which passes through the blood-brain barrier may be employed, including, but not limited to, J-cyclodextrin, K-cyclodextrin and derivatives thereof. See generally, U.S. Pat. Nos. 5,017,566, 5,002,935 and 4,983,586. Such compositions may also include a glycerol derivative as described by U.S. Pat. No. 5,153,179.

Delivery may also be obtained by conjugation of a therapeutic agent to a transportable agent to yield a new chimeric transportable therapeutic agent. For example, vasoactive intestinal peptide analog (VIPa) exerted its vasoactive effects only after conjugation to a monoclonal antibody (Mab) to the specific carrier molecule transferrin receptor, which facilitated the uptake of the VIPa-Mab conjugate through the blood-brain barrier. Pardridge (1991); and Bickel et al. (1993) *Proc. Natl. Acad Sci. USA* 90:2618-2622. Several other specific transport systems have been identified, these include, but are not limited to, those for transferring insulin, or insulin-like growth factors I and II. Other suitable, non-specific carriers include, but are not limited to, pyridinium, fatty acids, inositol, cholesterol, and glucose derivatives. Certain prodrugs have been described whereby, upon entering the central nervous system, the drug is cleaved from the carrier to release the active drug. U.S. Pat. No. 5,017,566.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

Example 1

Interaction of apoE with LRP and Effect on Neurite Outgrowth

Materials

Dimyristoylphosphatidylcholine (DMPC), DME/F12 (1:1 mixture of Dulbecco's nutrient modified Eagle's medium and Ham's mixture F12), media supplements (progesterone, putrescine, selenite, and transferrin), sodium chlorate, heparinase, lactoferrin, triolein, and egg yolk phosphatidylcholine (type XI-E) were purchased from Sigma Chemical Co. (St. Louis, Mo.), fetal bovine serum (FBS), and insulin from Gibco (Grand Island, N.Y.), suramin from Miles Inc. (FBA Pharmaceuticals, West Haven, Conn.), and DiI from Molecular Probes Inc. (Eugene, Oreg.). Neuro-2a was purchased from American Type Culture Collection (Rockville, Md.). Bovine CSF was obtained from Pel-Freez, Inc. (Fayetteville, Ark.).

Preparation of Lipoproteins and Liposomes

Rabbit β-VLDL (d<1.006 g/ml) were isolated from the plasma of New Zealand white rabbits fed a high-fat, high-cholesterol diet for four days according to the method described by Kowal (1989) *Proc. Natl. Acad. Sci. USA* 86:5810-5814. Rabbit VLDL (d<1.006 g/ml) were isolated by ultracentrifugation from fasting plasma obtained from rabbits fed a normal rabbit chow. The VLDL were washed once by ultracentrifugation at d=1.006 g/ml. Bovine CSF lipoproteins (d<1.21 g/ml) were isolated by ultracentrifugation according to the method described by Pitas et al. (1987) *J. Biol. Chem.* 262:14352-14360. They were washed once by recentrifugation through a solution of d=1.21 g/ml. Canine apoE $HDL_c$ (d=1.006-1.02 g/ml) were isolated by ultracentrifugation and Pevikon electrophoresis from the plasma of foxhounds fed a semisynthetic diet containing hydrogenated coconut oil and cholesterol according to the method described by Mahley et al. (1977) *Am. J. Pathol.* 87:205-226. The β-VLDL were iodinated according to the method described by Bilheimer et al. (1972) *Biochim. Biophys. Acta* 260:212-221, and free iodine was removed by PD10 column chromatography.

The DMPC vesicles were prepared essentially according to the method described by Innerarity et al. (1979) *J. Biol. Chem.* 254:4186-4190. The DMPC alone (90 mg) or with the addition of cholesterol (10 mg) was dissolved in benzene and dried by lyophilization. The lyophilized material was then resuspended in 3 ml of 0.15 M NaCl, 10 mM Tris-Cl, and 1 mM EDTA (pH 7.6) and sonicated for 30 min at 37EC using a sonifier cell disrupter (Branson 450, Danbury, Conn.) equipped with a microtip and full setting at 7 (50 watts).

Innerarity (1979), supra. The material was centrifuged for 10 min at 2,000 rpm (37EC), and the supernatant was used for addition to cells. The lipid emulsion A was prepared according to the methods described Pittman et al. (1987) *J. Biol. Chem.* 262:2435-2442; and Spooner et al. (1988) *J. Biol. Chem.* 263:1444-1453. Briefly, the lipids were mixed together in the following ratio: 100 mg of triolein and 25 mg of egg yolk phosphatidylcholine and then dried under a stream of nitrogen. The pellet was then resuspended in 5 ml of 10 mM Tris-Cl, 0.1 M KCl, and 1 mM EDTA (pH 8.0) buffer and sonicated according to the method described by Spooner et al. (1988). The material was then centrifuged for 10 min at 2,000 rpm. The composition of the final emulsion was 2.7:1 for triolein:phosphatidylcholine (wt:wt). The size and morphology of the emulsion particles were determined by negative staining electron microscopy.

Preparation of Expression Vectors

The expression vectors were assembled in the pBSSK plasmid (Stratagene, La Jolla, Calif.). The constructs contained the rat neuron-specific enolase (NSE) promoter (kindly provided by Dr. J. G. Sutcliffe, Scripps Clinic and Research Foundation, La Jolla, Calif.), which has been previously used to direct neuron-specific expression of the human amyloid precursor protein and β-galactosidase in transgenic mice. Quon et al. (1991) *Nature* 352:239-241; and Forss-Petter (1990) *Neuron* 5:187-197. In addition, the construct contained the first exon (noncoding), the first intron, and the first six bases of the second exon (prior to the initiation methionine) of the human apoE gene, followed by the apoE cDNA.

The apoE4 construct was identical except that it also contained the third intron (FIG. 1). The noncoding region of the fourth exon was downstream from the cDNA, followed by 112 bp of the 3'-flanking sequence of the human apoE gene that contains the polyadenylation signal. The apoE constructs for insertion in these expression vectors were kindly provided by Drs. S. Lauer and J. Taylor of the J. David Gladstone Institutes. The orientation of the cDNAs was confirmed by sequencing, using an Applied Biosystems automated sequencer. The final constructs were referred to as NSE-E3 (for apoE3 cDNA) and NSE-E4 (for apoE4 cDNA) (FIG. 1). Plasmid DNA was purified by two rounds of cesium chloride gradient ultracentrifugation according to the method described by Sambrook et al. (1989) *Molecular Cloning: A Laboratory Manual,* 2nd ed. Cold Spring Harbor Laboratory Press, Cold Spring Harbor, N.Y. To test the constructs, Chinese hamster ovary cells and human embryonic kidney 293 cells were transiently transfected (lipofectin-mediated), and the concentration of apoE in the medium was measured as described below. Similar levels of expression of apoE3 and apoE4 were achieved.

Production of Stably Transfected Neuro-2a Cell Lines

Cells at 20-30% confluence were cotransfected with pSV2neo and either NSE-E3 or NSE-E4 using a calcium phosphate precipitation protocol essentially as described by Chen et al. (1988) *BioTechniques* 6:632-638. Control cells were transfected with pSV2neo alone, following the same protocol. Stably transfected cells were selected by growth in DME/F12 media containing 10% FBS and 400 µg/ml of G418 (Geneticin, Gibco). Individual G418-resistant colonies were selected and expanded. Secretion of human apoE3 or apoE4 by the transfected cells was verified by Western blotting of the conditioned media.

ApoE Quantitation

Intracellular, cell-surface-bound, and secreted apoE were quantitated in cells maintained for 96 hr in N2 medium, a serum- and lipid-free medium (DME/F12 containing growth supplements as described in Bottenstein et al. (1980) *Exp. Cell Res.* 129:361-366), with or without added β-VLDL (40 µg cholesterol per ml). The medium was changed once at 48 hr. The secreted apoE reported is that present in the medium following the second 48 hr incubation. The media were collected and, after the addition of protease inhibitors, centrifuged to eliminate suspended cells. The cell monolayers were washed with PBS and incubated for 1 hr at 4 EC with 2 ml of DMEM/F12 containing 25 mM Hepes and 10 mM suramin, a polyanion that is able to release apoE bound to the cell surface. Ji et al. (1994). The apoE was precipitated from the medium and the suramin extract by addition of 50 µg/ml of fumed silica (Sigma, St. Louis, Mo.) and centrifugation at 13,000×g for 10 min.

Each pellet was washed three times with sterile water and dissolved in gel-loading buffer. Cellular apoE was extracted from the cells, following suramin removal of surface-bound apoE, using STEN buffer (50 mM Tris-Cl, pH 7.6, containing 150 mM NaCl, 2 mM EDTA, 1% NP-40, 20 mM PMSF, and 5 µg/ml leupeptin). Samples were electrophoresed on 5-20% polyacrylamide gradient gels containing sodium dodecyl sulfate, according to the method described by Ji et al. (1994) *J. Biol. Chem.* 269:13429-13436. The proteins were transferred to nitrocellulose paper by blotting and treated with an anti-human apoE polyclonal antiserum (1:1,000 dilution) raised in rabbit (generously provided by Dr. K. H. Weisgraber, Gladstone Institutes). The nitrocellulose immunoblot was then incubated with donkey anti-rabbit secondary antibody conjugated to horseradish peroxidase (1:5,000 dilution) (Amersham, Arlington Heights, Ill.). After washing to remove unbound antibody, the immunocomplex was detected using an ECL kit (Amersham), according to the manufacturer's instructions. Quantitation of the level of apoE bound, internalized, and secreted by the cells was accomplished by densitometric scanning (Ambis Scanner, San Diego, Calif.) and based on a standard curve of purified human plasma apoE3 and apoE4.

Cells were grown in DME/F12 containing 10% FBS and G418 (400 µg/ml). On the day the experiment was initiated, the cells were subcultured into 35 mm plates in DME/F12 with 10% FBS. The cells were allowed to adhere to the plastic plates for 2 hr at 37° C., and then the culture medium was changed to N2 medium with or without increasing concentrations of lipoproteins. After 48 hr at 37° C., the media were replaced with the same medium (with or without lipoproteins), and the incubation was continued for an additional 48 hr. (The CSF lipoproteins were dialyzed against N2 medium prior to addition to the cells.) The cells then were washed with DME/F12 containing 0.2% BSA, nonspecifically stained for 1 hr at 37° C. with DiI added in DMSO according to the method described by Nathan et al. (1994) *Science* 264:850-852, and fixed with 2.5% glutaraldehyde in PBS (v/v). Neurons were imaged in fluorescence mode with a confocal laser scanning system (MRC-600, BioRad, Hercules, Calif.), and the images were digitized with an Image-1/AT image analysis system (Universal Images, West Chester, Pa.). The neuronal images were coded before characterization, and the following variables were measured: 1) number of neurites (defined as cell surface projections at least one-half the cell diameter) on each neuron; 2) neurite branching (the number of branch points on each neurite); and 3) neurite extension (the length of the longest neurite, measured from the cell body). Typically, in each experiment the neurites of 20 to 40 neurons per plate were measured and the results preserved as the mean±S.E.M.

In studies on the effect of the inhibitors of lipoprotein binding to the LRP, cells were incubated for 1 hr at 37° C. in N2 medium containing the indicated concentrations of either lactoferrin, chlorate, or heparinase or with the receptor-associated protein (RAP). Then the β-VLDL were added, and the incubation was continued for a total of 96 hr. The reagents, except for β-VLDL, were re-added every 24 hr. The media and β-VLDL were replaced after 48 hr.

Cell Association and Degradation of $^{125}$I-β-VLDL

The cells were grown for 24 hr in 35 mm dishes in N2 medium alone. Then $^{125}$I-β-VLDL (3 μg of protein per ml of medium) were added, and the incubation was continued for 16 hr at 37 EC. The medium was analyzed for TCA-soluble lipoprotein degradation products according to the method described by Goldstein et al. (1983) *Met. Enzymol.* 98:241-260. The cells were placed on ice, washed with PBS containing 0.2% BSA, and dissolved in 0.1 N NaOH. Lipoprotein cell association was determined by measuring cellular radioactivity using a gamma counter (Beckman Gamma 8000, Beckman Instruments, Fullerton, Calif.) and according to the method described by Goldstein et al. (1983).

Cell Association of DiI-Labeled β-VLDL

The cells were grown for 24 hr in 35 mm dishes in N2 medium. Then DiI-labeled β-VLDL (4 μg of protein per ml of medium), was prepared according to the methods described by Pitas et al. (1983) *Arteriosclerosis* 3:2-12; and Pitas et al. (1981) *Arteriosclerosis* 1:177-185, were added, and the incubation was continued for 5 hr at 37° C.: The cells were then washed with PBS and fixed with 4% paraformaldehyde in PBS (v/v). Uptake of DiI-labeled β-VLDL was visualized by fluorescence microscopy. To quantitate the amount of DiI-labeled lipoprotein in the cells at the end of the incubation, the cells were scraped, using two 0.5 ml aliquots of PBS, and lyophilized. The DiI was extracted from the dried cell pellet with methanol and analyzed using a spectrofluorometer (excitation 520 nm, emission 570 nm). Pitas et al. (1983). Standards of DiI in methanol were used for quantitation.

Association of ApoE with Lipid Particles

ApoE3 and apoE4 were iodinated using Bolton-Hunter reagent (DuPont NEN, Boston, Mass.) according to the method described by Innerarity et al. (1983) *J. Biol. Chem.* 258:12341-12347, and then incubated with the lipid particles for 1 hr at 37° C. The samples were then fractionated by chromatography on a Superose 6 column (10/50 HR, Pharmacia Fine Chemicals, Uppsala, Sweden) and eluted with 1 mM EDTA in PBS at a constant flow rate of 0.5 ml/min. Fractions of 0.5 ml were collected and analyzed for cholesterol and triglyceride, and the $^{125}$I-apoE content was measured in a Beckman 8000 counter (Beckman Instruments) and according to the method described by Dong et al. (1994) *J. Biol. Chem.* 269:22358-22365.

Statistical Analysis

Data were analyzed using a paired t-test.

Results

The levels of apoE secreted into the medium, bound to the cell surface, and accumulated intracellularly by the stably transfected Neuro-2a cells expressing human apoE3 or apoE4 were assessed by Western blot analysis and quantitated by densitometry. The results obtained are presented in Table 1.

TABLE 1

ApoE3 or apoE4 secreted, releasable by suramin, or present inside cells stably transfected with apoE3 or apoE4 cDNA

| Cells | Secreted | Releasable ng of apoE/mg of cell protein | Intracellular |
|---|---|---|---|
| ApoE3-expressing | | | |
| Clone #1 | 54 | 6.2 | 140 |
| +β-VLDL | 56 | 7.2 | 119 |
| Clone #3 | 44 | 4.9 | 259 |
| +β-VLDL | 45 | 4.3 | 251 |
| ApoE4-expressing | | | |
| Clone #4 | 60 | 6.7 | 215 |
| +β-VLDL | 63 | 5.3 | 231 |
| Clone #5 | 69 | 8.0 | 135 |
| +β-VLDL | 62 | 6.5 | 128 |
| Clone #6 | 89 | 5.2 | 111 |
| +β-VLDL | 87 | 5.6 | 105 |

To obtain the results depicted in Table 1, transfected cells were incubated for 96 hr in medium with or without β-VLDL (40 μg cholesterol/ml). The medium was changed at 48 hr. ApoE secreted in the last 48 hr, intracellular, and suramin-releasable (surface-bound) apoE were quantitated at the end of the 96 hr of incubation as described in Nathan et al. (1995). The data are the mean of two separate determinations. The duplicates did not differ by more than 12%.

The results depicted in Table 1 indicate that the cells secreted 44-54 ng of apoE3 and 60-89 ng of apoE4 per mg of cell protein in 48 hr. The apoE3- and apoE4-secreting cells had similar amounts of apoE bound to the cell surface (releasable by suramin treatment), ranging from 4.9 to 8.0 ng of apoE per mg of cell protein. The intracellular content of apoE in the two apoE3-expressing cell lines was 140 and 259 ng of apoE per mg of cell protein. Similar amounts of intracellular apoE (111-215 ng/mg) were seen in the apoE4-expressing cell lines. The addition of β-VLDL to the cells did not have a significant effect on the amount of apoE secreted, surface-bound, or present within the apoE3- or apoE4-secreting cells (Table 1).

In initial experiments, two Neuro-2a cell lines that secreted similar amounts of apoE3 (clone 1, 54 ng/mg of cell protein) and apoE4 (clone 4, 60 ng/mg of cell protein) (Table 1) were used to examine neurite growth. When these cells were grown in N2 medium in the absence of β-VLDL, there were no apparent differences in neurite outgrowth between the apoE3- and apoE4-secreting cells. However, incubation of the cells in N2 medium containing β-VLDL resulted in a markedly different pattern in the neurite outgrowth from these cells. ApoE3-secreting cells incubated with β-VLDL developed long neurites, whereas in apoE4-secreting cells neurite outgrowth was suppressed.

Differences in neurite outgrowth in the absence and presence of increasing concentrations of β-VLDL were quantitated by measuring the number of neurites per cell, neurite branching, and neurite extension (FIGS. 2A, B, and C, respectively). The values for the non-apoE transfected control cells incubated for 96 hr in N2 medium in the absence of β-VLDL are set at 100%. The expression of either apoE3 or apoE4 by the transfected Neuro-2a cells did not influence neurite number, branching, or extension when the cells were grown in N2 medium in the absence of added lipoprotein (FIGS. 2A, B, and C). To obtain the results depicted in FIG. 2, cells (clone #1 for apoE3-expressing and clone #4 for apoE4 expressing) were incubated for 96 hr in N2 medium alone or in medium containing increasing concentrations of β-VLDL. The media were changed at 48 hr. The cells were stained with DiI and fixed, and the indicated parameters were measured. Each data point was obtained by the measurement of 20-50 cells expressing neurites in four separate experiments. The data are presented as the percentage of the value obtained with control cells with N2 medium alone. The data are the mean±the S.E.M. As depicted in FIG. 2, the average values obtained with control cells incubated with N2 medium alone were: A: neurites per cell=3; B: branch points per neurite=2; C: average neurite length=155 Tm.

For calculation of the level of significance for the effect of added β-VLDL, the results in the presence of β-VLDL are, compared to the data obtained with the same cells in the absence of β-VLDL (i.e., grown in N2 medium alone). *$p<0.025$; $p<0.010$; *$p<0.005$.

However, as shown in FIG. 2A, the addition of β-VLDL resulted in an increase in the number of neurons in the control cells and in the cells secreting apoE3 (significantly increased at 40 μg of β-VLDL cholesterol/ml compared with apoE3-secreting cells in N2 medium). On the other hand, in the presence of high concentrations of β-VLDL, the Neuro-2a cells secreting apoE4 showed a significant reduction in the number of neurites per cell as compared with the apoE4-secreting cells in the N2 medium.

As previously described for DRG cells (Handelmann et al. (1992) *J. Lipids Res.* 33:1677-1688; and Nathan et al. (1994)), the addition of β-VLDL alone resulted in increased branching of neurites. As shown in FIG. 2B, addition of β-VLDL to the non-apoE-transfected cells resulted in a significant increase in neurite branching. In addition, at the highest concentration of β-VLDL cholesterol, the apoE3-secreting cells displayed enhanced branching by comparison with the apoE3-secreting cells grown in N2 medium alone. In contrast, the apoE4-secreting cells tended to show decreased branching when incubated with β-VLDL; however, this decrease did not reach statistical significance.

Neurite extension was increased in the Neuro-2a cells secreting apoE3 when they were incubated with the highest concentrations of β-VLDL. In contrast, in the apoE4-secreting cells neurite extension was very significantly suppressed even at the lowest concentration of β-VLDL used (FIG. 2C).

Figure 3:
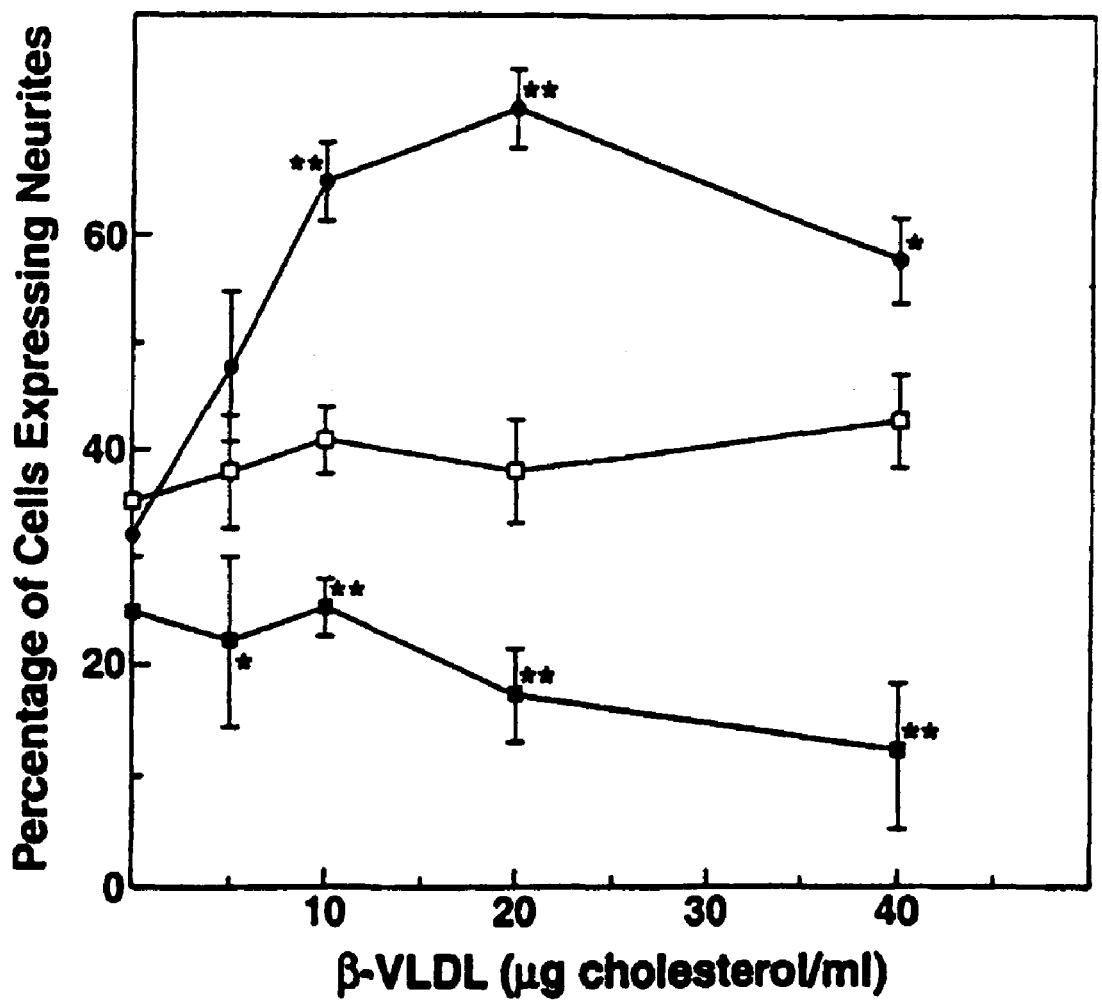
FIG. 3 is a graph depicting the effect of β-VLDL on the percentage of cells expressing neurites. Four different fields in each dish were selected, and the percentage of cells displaying neurites was measured. Data are the means of three different experiments performed in duplicate (±S.E.M.). The percentages of cells expressing neurites in the absence of β-VLDL were: control cells, 35±11 (open squares); apoE3-expressing cells, 32∀9 (closed circles); apoE4-expressing cells, 25±13 (closed squares). *p<0.025 versus control; **p<0.005 versus control.

The results described in FIG. 2 were based on a comparison of cells having neuritic outgrowths and did not take into account those Neuro-2a cells without neuritic extensions. Approximately 25-30% of the Neuro-2a cells in N2 medium possessed neurite extensions (defined as a cell-surface projection of at least one-half the cell diameter). However, as shown in FIG. 3, it was apparent that in the presence of β-VLDL, the number of apoE3-secreting cells developing neurites increased markedly to 60-70% of the total. On the other hand, the number of apoE4-secreting cells developing neuritic extensions was significantly reduced, compared with the control or apoE3-secreting cells. Thus, the apoE3-secreting cells incubated with β-VLDL not only had longer neuritic extensions but also showed an increase in the number of cells with neurites. The apoE4-secreting cells grown in the presence of β-VLDL showed fewer neurites, and those that were produced were much shorter.

To ensure that the differential effect of β-VLDL on neurite outgrowth in the apoE3- and apoE4-secreting cells was not due to clonal variation or to differences in the secretion or intracellular content of apoE in the various cell lines, additional experiments were performed with the other stably transfected cell lines secreting apoE3 or apoE4. Incubation of these cells with β-VLDL also resulted in differential effects of apoE3 and apoE4 on neurite outgrowth. The results obtained are presented in Table 2.

TABLE 2

Effect of β-VLDL (40 μg cholesterol/ml medium) on the number of neurites per cell, neurite branching, and neurite extension from cells stably transfected with apoE3 or apoE4

| Cell type | Number of Neurites | Branching | Extension |
|---|---|---|---|
| | (% of values obtained with control cells in N2 medium alone) | | |
| ApoE3-expressing | | | |
| Clone #1 | 165 ± 30 | 186 ± 39 | 186 ± 13 |
| Clone #2 | 150 ± 25 | 180 ± 15 | 190 ± 23 |
| Clone #3 | 170 ± 39 | 175 ± 20 | 180 ± 25 |
| ApoE4-expressing | | | |
| Clone #4 | 43 ± 25 | 65 ± 26 | 41 ± 9 |
| Clone #5 | 49 ± 15 | 70 ± 31 | 50 ± 15 |
| Clone #6 | 53 ± 19 | 60 ± 25 | 45 ± 19 |

In Table 2, the level of secretion of apoE by clones #1, #3, #4, #5, and #6 is as described for Table 1. Clone #2 secreted 36 ng of apoE3/mg of cell protein/48 hr. Surface-bound and internalized apoE was not quantitated for clone #2. The conditions for incubation with β-VLDL are as described for FIG. 2. Each data point was obtained by the measurement of 25-40 cells. The data are the mean±S.E.M.

As summarized in Table 2, in the presence of β-VLDL, all of the apoE4-secreting cells showed a significant reduction in the number of neurites expressed, branching, and neurite extension, whereas the apoE3-secreting cells displayed an increased number of neurites, increased branching, and increased extension as compared to cells grown in N2 medium lacking a source of lipoprotein.

To determine whether apoE4 blocks neurite extension in the presence of β-VLDL or whether it induces neurite retraction, the cells were incubated for 48 hr in N2 medium alone to stimulate neurite outgrowth. The medium was changed, and the cells incubated for an additional 48 or 96 hr in media with β-VLDL (40 μg of cholesterol per ml). The addition of β-VLDL did not decrease the extension of neurites of apoE4-expressing cells compared with cells incubated in N2 medium alone. Therefore, apoE4 in the presence of β-VLDL, inhibits neurite extension directly and does not cause a retraction of neurites that have already extended.

Other lipoproteins were used to determine if any lipid vehicle carrying apoE would substitute for β-VLDL. Incubation of the apoE3- or apoE4-expressing cells with rabbit VLDL, a lipoprotein rich in triglyceride (Tg), resulted in similar effects on neurite extension as obtained with β-VLDL. The results are presented in Table 3.

TABLE 3

Effect of β-VLDL, VLDL or lipid emulsions on neurite extension
from cells stably transfected with apoE3 or apoE4 cDNA

| Treatment | Lipid composition (wt/wt/wt) | Mean Size (nm ± S.D.) | Control | ApoE3-expressing | apoE4-expressing |
|---|---|---|---|---|---|
| | | | % of value obtained with control cells in N2 medium alone | | |
| N2 alone | , | , | 100 ± 10 | 110 ± 15 | 115 ± 11 |
| β-VLDL | CHOL:Tg:PL (5.6:0.4:1) | 43.7 ± 25.6 | 120 ± 15 | 160 ± 18$^a$ | 60 ± 13$^a$ |
| VLDL | CHOL:Tg:PL (1:7.4:1) | 39.5 ± 18.7 | 110 ± 11 | 155 ± 21$^a$ | 61 ± 19$^a$ |
| Emul A | Tg:PL (2.7:1) | 35.8 ± 14.9 | 95 ± 14 | 150 ± 12$^a$ | 75 ± 12$^a$ |

To obtain the results depicted in Table 3, cells (clone #1 for apoE3-expressing and clone #4 for apoE4-expressing) were incubated for 96 hr in N2 medium alone or containing the indicated concentrations of particles: β-VLDL, 40 µg cholesterol/ml medium (this corresponds to 5 µg triglyceride/ml medium); VLDL, 5 µg triglyceride/ml medium; emulsion A, 5 µg triglyceride/ml medium. CHOL=cholesterol; Tg=triglyceride; PL=phospholipid. Each data point was obtained by the measurement of 30-40 cells expressing neurites in three separate experiments. The data are the mean±S.E.M. $^a$p<0.010 versus control***.

As shown in Table 3, when the Neuro-2a cells secreting apoE3 were incubated with VLDL, they showed an increase in neurite extension, whereas the apoE4-secreting cells in the presence of VLDL showed an inhibition of neurite extension. In other experiments, human LDL and canine apoE HDL$_C$, an apoE-enriched plasma high density lipoprotein (HDL) induced by cholesterol feeding and resembling apoE-containing lipoproteins in the CSF (Pitas et al. (1987)), also were used. The apoE3- and apoE4-secreting Neuro-2a cells did not respond to LDL (40 µg cholesterol/ml) (i.e., there was no difference in neurite extension as compared with control cells grown in N2 medium alone). On the other hand, incubation of apoE HDL$_C$ (40 µg cholesterol/ml) with the apoE4-secreting or apoE3-secreting cells resulted in only a small reduction or increase in neurite extension, respectively (control cells in N2 medium, 100%; apoE4-secreting cells plus HDL$_C$, 85-90% of the value obtained with N2 medium; apoE3-secreting cells plus HDL$_C$, 110% of the value obtained with N2 medium).

Liposomes and lipid emulsions also were used in an attempt to define the type of lipid vehicle required for the delivery of the apoE. The DMPC emulsion alone or DMPC complexed with cholesterol were incubated with the apoE3- and apoE4-secreting cells for 96 hr at increasing phospholipid concentrations of up to 45 µg phospholipid and 5 µg cholesterol/ml medium (higher concentrations were toxic to the cells).

In these studies, there was no effect on neurite outgrowth with either of the apoE-transfected Neuro-2a cells. Previously, it was shown that apoE complexes with DMPC and mediates high-affinity binding to the LDL receptor. Pitas et al. (1980) *J. Biol. Chem.* 255:5454-5460. On the other hand, a lipid emulsion particle (emulsion A in Table 3), which was a triglyceride- and phospholipid-containing spherical particle (approximately 35.8 nm), caused a significant enhancement of neurite extension in the apoE3-secreting cells and was associated with an inhibition of outgrowth in the apoE4-secreting cells. Thus, specific combinations of lipids and/or a unique particle size may be required to elicit the apoE isoform, specific effects on neurite outgrowth. It is interesting to note that the delivery of cholesterol to the cells does not appear to be required for the differential effect.

Figure 4:
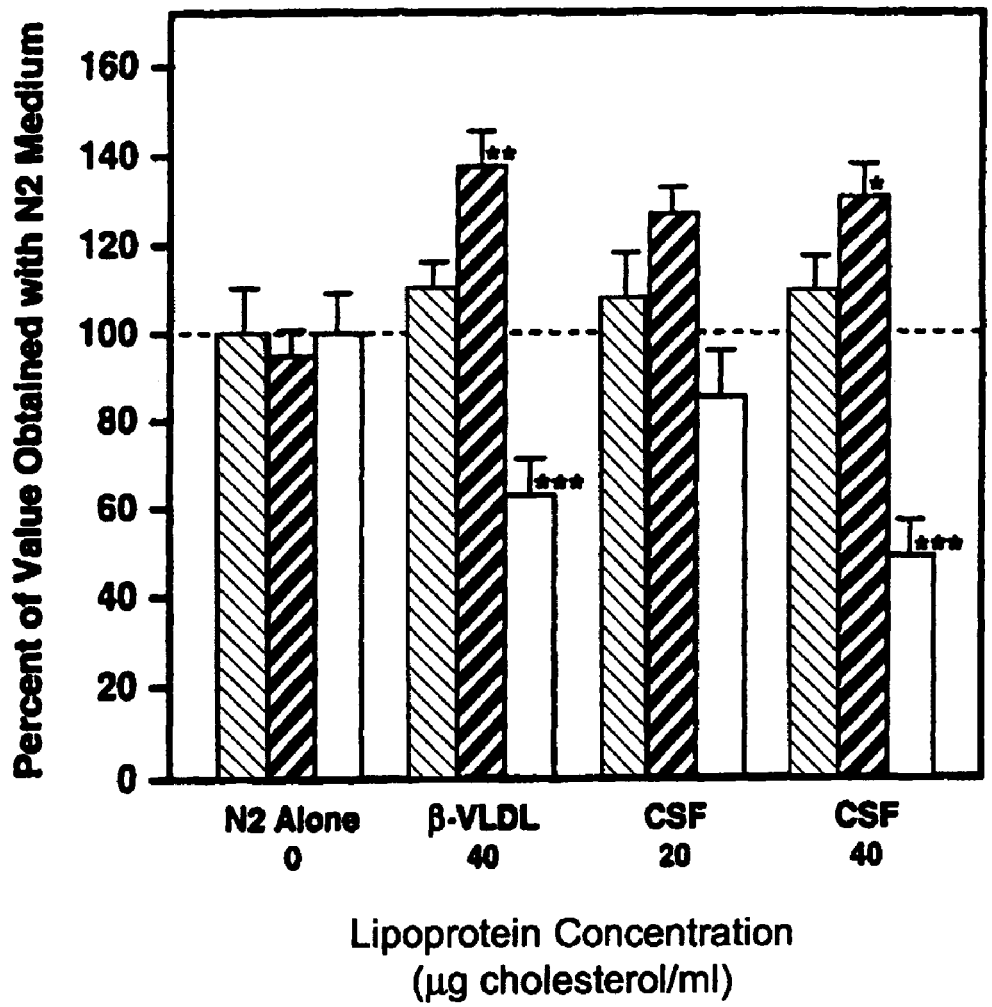
FIG. 4 is a bar graph depicting the effect of cerebrospinal fluid (CSF) lipoproteins on neurite extensions from Neuro-2a cells stably transfected to express apoE3 or apoE4. Cells were incubated with β-VLDL or bovine CSF lipoproteins (d<1.21 g/ml). Each data point represents the measurement of 20-40 neurons. The data are reported as the mean±S.E.M. The solid black bars represent the control. The striped bars represent apoE3 expressing cells. The solid white bars represent apoE4 expressing cells. *p<0.025, p<0.01, *p<0.005.

Additional studies using the lipoproteins from bovine CSF suggest that natural lipoproteins in the CNS may mediate the isoform-specific effects of apoE3 and apoE4. As shown in FIG. 4, addition of lipoproteins isolated from CSF (d<1.21 g/ml) to the cells caused an inhibition of neurite outgrowth from the apoE4-expressing cells and an increase in outgrowth from the apoE3-expressing cells. When CSF lipoproteins were used at a concentration of 40 µg lipoprotein cholesterol/ml, the effect was similar to that obtained using β-VLDL at the same concentration.

CSF lipoproteins (d<1.21 g/ml) were analyzed for protein and cholesterol content and apolipoprotein composition. The ratio of cholesterol to protein was approximately 1:1, similar to data reported for canine CSF. Pitas et al. (1987). The bovine CSF lipoproteins (d<1.21 g/ml) contained only apoE and apoA-I when separated by sodium dodecyl sulfate polyacrylamide gel electrophoresis and visualized by Coomassie Brilliant Blue staining. These results are similar to those reported previously for human and canine CSF lipoproteins. Pitas et al. (1987); and Roheim et al. (1979) *Proc. Natl. Acad. Sci. USA* 76:4646-4649.

The ability of the neuroblastoma cells to bind, internalize, and degrade β-VLDL was examined to determine whether the differences in neurite outgrowth in the apoE3- and apoE4-expressing cells was due to a different ability of the secreted apoE3 and apoE4 to stimulate the delivery of apoE and/or lipoprotein lipids to the cells. In these studies, $^{125}$I-β-VLDL were used to quantitate the binding, uptake, and degradation of the lipoproteins in the Neuro-2a cells. The results are presented in Table 4.

TABLE 4

Cell association and degradation of $^{125}$I-β-VLDL
by stably transfected and control cells

| | $^{125}$I-β-VLDL | |
|---|---|---|
| Cell type | Cell association | Degradation |
| | (ng of lipoprotein protein/mg of cell protein) | |
| Control cells | 750 ± 16 | 2,467 ± 331 |
| ApoE3-expressing cells | 671 ± 40$^a$ | 1,945 ± 219 |
| ApoE4-expressing cells | 662 ± 50$^a$ | 1,788 ± 188$^b$ |

To obtain the results depicted in Table 4, cells were incubated for 24 hr in N2 medium alone. The $^{125}$I-β-VLDL (3 µg protein/ml medium) were then added, and after 16 hr at 37° C. the lipoprotein cell association (bound and internalized) and degradation by Neuro-2a cells were measured. The data reported are the mean of two separate experiments performed in duplicate (±S.D.). Control=cells transfected with pSV2neo alone. In Table 4, a represents <0.05 versus control and b represents <0.01 versus control.

The results presented in Table 4 indicate that the total amount of cell-associated (bound and internalized) $^{125}$I-β-VLDL was very similar in the apoE3- and apoE4-secreting cells (both were slightly lower than that seen in the non-apoEtransfected control cells). The degradation of $^{125}$I-β-VLDL by the apoE3- and apoE4-secreting cells was similar. There was a small (but statistically significant) decrease in the degradation of $^{125}$I-β-VLDL by the apoE4-secreting cells when compared with the non-apoE-transfected control Neuro-2a cells.

In a parallel experiment, the cells were incubated with DiI-labeled β-VLDL to visualize the internalization of the lipoproteins in the apoE3- and apoE4-secreting cells by fluorescence microscopy. Following internalization, DiI is trapped in the lysosomes, and the fluorescent intensity of the cells, therefore, is proportional to the total amount of lipoprotein internalized and degraded. Pitas et al. (1983). In these studies, no difference in the uptake of DiI-labeled β-VLDL was observed in the apoE3- and apoE4-secreting cells. Extraction and quantitation of the DiI from cells incubated with DiI-labeled β-VLDL (40 μg of cholesterol per ml) for 16 hr at 37° C. confirmed the visual impression that the uptake of DiI-labeled β-VLDL was similar in the apoE3- and apoE4-secreting cells. The control cells incorporated 8.9±0.4 ng of DiI per mg of cell protein, while the apoE3- and apoE4-expressing cells incorporated 10.2±1.0 and 10.8±0.3 ng of DiI per mg of cell protein, respectively.

To demonstrate that apoE binds to the lipid particles when it is present at the concentrations secreted by the cells, radiolabelled apoE3 or apoE4 was incubated with the β-VLDL, VLDL, or emulsion A for 1 hr at 37° C. (100 ng of apoE with 40 μg β-VLDL cholesterol or 100 ng of apoE with either 5 μg of VLDL or emulsion A triglyceride) and fractionated by FPLC. Approximately 70% of the apoE was associated with the β-VLDL and 50% with the VLDL and emulsion A. There was no difference in the amount of apoE3 or apoE4 associated with the lipid particles.

Example 2

Specific Inhibition of apoE Binding to apoE Binding R

To determine which receptor was involved in mediating the differential effects of apoE3 and apoE4 on neurite outgrowth, inhibitors that block the binding and internalization of apoE-enriched lipoproteins by the HSPG-LRP pathway, but not by the LDL receptor pathway, were used. The effect on neurite outgrowth was then determined. Prior to the addition of β-VLDL, the cells were preincubated for 1 hr with either heparinase (20 units/ml) and chlorate (20 mM), with the RAP (5 Tg/ml), or with lactoferrin (10 μg/ml). The binding of apoE-enriched lipoproteins to the LRP requires their initial binding to cell-surface HSPG. Heparinase and chlorate cleave and reduce the sulfation of cell-surface HSPG, respectively. Ji et al. (1993) *J. Biol. Chem.* 268:10160-10167; and Humphries et al. (1989) *Met. Enzymol.* 179:428-434. Lactoferrin blocks binding of lipoproteins to both HSPG and LRP, whereas the RAP primarily blocks the binding of apoE-enriched lipoproteins to the LRP. All of these reagents previously have been shown to inhibit the uptake of apoE-enriched β-VLDL by the LRP. Mahley et al. (1994) *Ann. N.Y. Acad. Sci.* 737:39-52; Ji et al. (1993); Ji et al. (1994a); and Willnow et al. (1992) *J. Biol. Chem.* 267:26172-26180. As shown in FIG. 2, β-VLDL alone stimulated the outgrowth of neurites. The stimulation of neurite outgrowth by β-VLDL was further enhanced in the apoE3-expressing cells and markedly inhibited in the apoE4-secreting cells (Table 5).

TABLE 5

Effect of chlorate, heparinase, the RAP, and lactoferrin in the presence of β-VLDL on neurite extension from cells stably transfected with apoE3 or apoE4 cDNA

| Treatment | Control | ApoE3-expressing | ApoE4-expressing |
|---|---|---|---|
| | % of value obtained with control cells in N2 medium alone | | |
| N2 alone | 100 ± 8 | 105 ± 10 | 103 ± 9 |
| β-VLDL (40 μg cholesterol/ml) | 160 ± 13 | 209 ± 13$^a$ | 70 ± 4$^b$ |
| β-VLDL + chlorate (20 mM) and heparinase (20 units/ml) | 159 ± 14 | 163 ± 20$^c$ | 138 ± 12 |
| β-VLDL + RAP (5 μg/ml)$^d$ | 176 ± 11 | 179 ± 15 | 160 ± 16 |
| β-VLDL + lactoferrin (10 μg/ml) | 128 ± 16 | 154 ± 19$^c$ | 130 ± 12 |

To obtain the results depicted in Table 5, cells were incubated for 1 hr in N2 medium alone or containing the indicated concentrations of chlorate, heparinase, RAP, or lactoferrin. Then the β-VLDL were added, and the incubation was continued for a total of 96 hr. The reagents, except for β-VLDL, were re-added every 24 hr. The media and β-VLDL were changed at 48 hr. Each data point was obtained by measuring 30-40 neurons expressing neurites in two separate experiments. Data are the mean±S.E.M. $^a$p<0.05, $^b$p<0.01 versus value obtained with control cells (non-apoE-expressing cells incubated with β-VLDL). $^c$p<0.05 versus apoE3-expressing cells with β-VLDL alone. $^d$In a parallel set of experiments, 5 μg/ml of RAP did not block the binding of DiI-labeled LDL to the Neuro-2a cells.

The results depicted in Table 5 indicate that the addition of chlorate and heparinase or the RAP did not block the stimulatory effect of β-VLDL on neurite outgrowth in the control cells (Neuro-2a cells not expressing apoE), suggesting that the effect of β-VLDL alone is mediated by the LDL receptor; however, these reagents blocked the isoform-specific effects in the cells secreting apoE (Table 5). Chlorate and heparinase treatment of the cells or the addition of the RAP prevented the stimulation of neurite extension in the apoE3-expressing cells incubated with β-VLDL (that is, significantly decreased the β-VLDL, induced neurite extension in the Neuro-2a cells secreting apoE3). Moreover, chlorate and heparinase or the RAP blocked the inhibition of neurite extension seen in the apoE4-expressing cells (that is, the apoE4-expressing cells in the presence of β-VLDL did not demonstrate inhibition of neurite extension but, in fact, showed increased extension) (Table 5). In the presence of heparinase and chlorate or the RAP, in the apoE-secreting cells, neurite outgrowth was similar to that observed when β-VLDL were added to the control cells in the absence of apoE (Table 5). Therefore, in the presence of these reagents, the LDL receptor, mediated effect of β-VLDL was not blocked. Lactoferrin also blocked the effects of apoE3 and apoE4 on neurite outgrowth; however, it also slightly suppressed the effect of β-VLDL on neurite extension in the control cells. These data show that inhibition of the interaction between β-VLDL and the HSPG-LRP pathway prevents the differential effects of apoE3 and apoE4 on neurite outgrowth (Table 5).

In dorsal root ganglion or neuroblastoma cells, apoE3 plus a source of lipid supports and facilitates neurite extension. ApoE3 appears to accumulate widely in cell bodies and neurites, stabilize the cytoskeleton and support neurite elongation, and directly or indirectly modulate microtubule assembly. ApoE4, on the other hand, does not appear to accumulate within neurons or support neurite extension, and may even destabilize the microtubule apparatus. The apoE4 effect appears to be mediated via the LRP pathway. Individuals with apoE4 clearly have normal neuronal development early in life. However, apoE4 may exert its detrimental effects later in life, by not allowing or supporting remodeling of synaptic connections. This affect is believed to be important in the pathogenesis of Alzheimer's disease because apoE4 is believed to contribute to Alzheimer's disease by aiding the formation of dense, complicated, possibly toxic plaques of Aβ peptide.

Example 3

Methods of Detection of Agents that Interfere with the apoE4 Domain Interaction

ApoE4 is iodinated using the Bolton-Hunter reagent (New England Nuclear Corp., Boston, Mass.) as previously described by Innerarity et al. (1979) *J. Biol. Chem.* 254:4186-4190, with specific activities ranging from 200 to 1100 dpm/ng. The iodinated apoE4 (0.5-2 mg in 50-10 ml 0.1 M $NH_4HCO_3$) is incubated with the test reagent or compound and the mixture is added to 250 ml of plasma from normal subjects at 37° C. for 2 h. Plasma is then fractionated into the various lipoprotein classes by chromatography on a Superose 6 column (10/50 HR, Pharmacia Fine Chemicals, Uppsala, Sweden) eluted with 20 mM sodium phosphate (pH 7.4), containing 0.15 M NaCl. The column flow rate is 0.5 ml/min, 0.5 ml fractions are collected, and the $^{125}I$ content is determined in a Beckman 8000 gamma counter (Beckman Instruments, Fullerton, Calif.). Reagents that interfere with apoE4 domain interaction will shift the preference of the "modified" apoE4 from VLDL to HDLs, resulting in a distribution that resembles that of apoE3 (run in parallel as a control).

ApoE Metabolism

The metabolism of apoE-enriched β-VLDL by cultured neurons (Neuro-2a cells) was examined in three ways: (1) by measuring the cell association (binding and internalization) of apoE-enriched $^{125}I$-β-VLDL; (2) by examining the metabolism of apoE-enriched DiI-labeled β-VLDL (DiI serving as a fluorescent marker for the lipid moieties of the lipoprotein particle); and (3) by quantitating the ability of the apoE-enriched β-VLDL to increase the content of cellular cholesterol.

Example 4

Binding and Internalization of ApoE-Enriched β-VLDL Particles

Materials and Methods for Examples 4-6

Heparinase I and specific phospholipase C were purchased from Sigma Chemical Company (St. Louis, Mo.). Suramin was obtained from Research Biochemicals International (Natick, Mass.). Purified human plasma apoE and sheep anti-human apoE antibody were provided by Dr. Karl Weisgraber (Gladstone Institute of Cardiovascular Disease, San Francisco, Calif.). Donkey anti-sheep IgG was purchased from Jackson ImmunoResearch Laboratories, Inc. (West Grove, Pa.).

Preparation of Lipoproteins

Rabbit β-VLDL (d<1.006 g/ml) were isolated from the plasma of New Zealand White rabbits fed a high-fat, high-cholesterol diet for 4 days. The ratio of cholesterol to protein in this β-VLDL ranged from ~15 to 20:1. Human apoE-enriched β-VLDL were prepared by incubating apoE with β-VLDL at 37° C. for 1 h. For some experiments, the apoE-enriched β-VLDL were reisolated by fast-performance liquid chromatography as follows. Either $^{125}I$-β-VLDL and unlabeled apoE or $^{125}I$-apoE and unlabeled β-VLDL were mixed in a 1:1.5 ratio of β-VLDL protein to apoE and incubated at 37° C. for 1 h. The mixture (250 μl) was then fractionated by chromatography on a Superose 6 column (Pharmacia Fine Chemicals, Uppsala, Sweden, 10/50 HR). The flow rate was 0.5 ml/min, and 0.5 ml fractions were collected. The elution profile was monitored by quantitation of $^{125}I$ and cholesterol.

Labeling of Lipoproteins and ApoE

The β-VLDL were iodinated by the method of Bilheimer et al. (1972) *Biochim. Biophys. Acta.* 260:212-221. Apolipoproteins E3 and E4 were iodinated by the Bolton-Hunter procedure (Bolton et al. (1973) *Biochem. J.* 133:529-539). Free iodine was removed by P10 column chromatography. The β-VLDL were labeled with 1,1'-dioctadecyl-3,3,3',3'-tetramethylindocarbocyanine (DiI), as previously described (Pitas et al. (1981) *Arteriosclerosis* 1:177-185).

Detection of Intact ApoE in Cell Extracts

Murine neuroblastoma (Neuro-2a) cells were grown to ~100% confluence in Dulbecco's modified Eagle's medium (DMEM)/F 12 (1:1) containing 10% fetal bovine serum (FBS), washed with N2 medium, and incubated in N2 medium with β-VLDL (40 μg cholesterol/ml) alone or together with 30 μg/ml of iodinated apoE3 or iodinated apoE4. At the times indicated, the surface-bound apoE was removed by incubation with 10 mM suramin for 30 min at 4° C. The cells were then washed three times with phosphate-buffered saline (PBS) at 4° C. and gently scraped with a rubber policeman. The cells were dissolved in sodium dodecyl sulfate (SDS)—sample buffer, and the cell proteins were separated by 3-20% SDS—polyacrylamide gel electrophoresis (PAGE) and transferred to nitrocellulose membranes; apoE was detected by autoradiography.

Cell Culture

Neuro-2a cells were maintained in DMEM/F12 (1:1) containing 10% FBS; this medium was replaced with serum-free medium ~16 h before use. Human skin fibroblasts were grown in DMEM containing 10% FBS. The LDL receptor-negative fibroblasts were grown in minimal essential medium supplemented with 10% FBS. Human hepatoma (HepG2) cells were maintained in minimal essential medium containing 10% FBS, 1% human nonessential amino acids, and 1% sodium pyruvate as described (Ji et al. (1994) *J. Biol. Chem:* 269:2764-2772). Mutant Chinese hamster ovary (CHO) cells pgs A-745 (xylose transferase-deficient), which do not produce any glycosaminoglycans, and pgs D-677 (N-acetylglucosamine transferase-deficient and glucuronic acid transferase-deficient), which do not produce heparin sulfate (Esko (1991) *Curr. Opin. Cell Biol.* 3:805-816) were kindly provided by Dr. J. D. Esko (University of Alabama, Birmingham). The CHO cells were maintained in F12 medium containing 7.5% FBS. Mouse LRP-negative ($LRP^{-/-}$) and LRP heterozygous fibroblasts ($LRP^{+/-}$), provided by Dr. J. Herz (University of Texas Southwestern Medical School, Dallas, Tex.), were maintained in DMEM containing 10% FBS. The cholesterol content of the β-VLDL or cultured cells was assayed.

Immunochemistry

Neuro-2a cells or fibroblasts grown in tissue culture dishes were washed with serum-free medium and incubated at 37° C. with apoE3 (30 μg/ml) or apoE4 (30 μg/ml) plus β-VLDL (40 μg of cholesterol/ml for the time indicated. After incubation, the cells were placed immediately on ice and washed with phosphate buffer. Cells were then fixed with 3% paraformaldehyde in 0.1 M phosphate buffer (pH 7.4) for immunofluorescence cytochemistry. Immunofluorescence from apoE was detected. The intensity of apoE immunofluorescence was quantitated by confocal microscopy.

Cell Association, Internalization, and Degradation of ApoE Plus β-VLDL

Cultured cells were grown to ~100% confluence, washed twice with fresh serum-free medium, and incubated at 37° C. with apoE-enriched β-VLDL. Before addition to the cells, the β-VLDL and apoE were incubated together (5 and 7.5 μg of protein, respectively, unless otherwise indicated) for 1 h at 37° C. Some cells were incubated with 50 μM chloroquine, and inhibitor of lysosomal protease, at 37° C. for 2 h before addition of the apoE-enriched β-VLDL. At the times indicated, the cells were placed on ice, and the medium was assayed for protein degradation products. For the cell association studies, Neuro-2a cells were washed five times on ice with 0.1 M PBS containing 0.2% bovine serum albumin and once with 0.1 M PBS. Cell-associated ligand represents both bound and internalized material. The fibroblasts were washed three times with DMEM-Hepes on ice and incubated with 10 mM suramin at 4° C. for 30 min to remove surface-bound ligand. The radioactivity remaining within the cells represents that which was "internalized." After washing, the cells were dissolved in 0.1 N NaOH for measurement of radioactivity and protein concentration.

Internalization of $^{125}$I-apoE-enriched β-VLDL by fibroblasts and by Neuro-2a cells was also studied at 18° C. The cells were placed in an 18° C. incubator for 20 min before the addition of the lipoproteins and then incubated for an additional 3 h at 18° C. After incubation, the cells were placed on ice, washed three times with DMEM-Hepes, and incubated with 10 mM suramin at 4° C. for 30 min to remove cell surface-bound $^{125}$I-apoE. Degradation products of $^{125}$I-β-VLDL or $^{125}$I-apoE in the medium were assayed.

Uptake of DiI-Labeled β-VLDL by Cultured Cells

Neuro-2a cells were incubated for 2 h at 37° C. with DiI-labeled β-VLDL alone or together with either apoE3 or apoE4. The cells were then washed and solubilized with 0.1 N NaOH, and the cell-associated DiI, which is proportional to the total amount of lipoprotein metabolized (bound, internalized, and degraded), was assayed.

Heparinase and Specific Phospholipase C Treatment of Cells

The cells were pretreated at 37° C. with heparinase I (10 units/ml) for 1 h or with specific phospholipase C (5 units/ml) for 30 min. The cells were then incubated in the presence of the enzymes with β-VLDL together with either apoE3 or apoE4. The β-VLDL (5 μg protein/ml) and apoE (7.5 μg/ml) were mixed and incubated together for 1 h at 37° C. before addition to the cells.

Pulse Chase of $^{125}$I-apoE+β-VLDL by Wild-Type and HSPG-Deficient CHO Cells

Cultured cells were grown to ~100% confluence, placed on ice, and washed twice with cold DMEM-Hepes. The cells were then incubated with $^{125}$I-apoE+β-VLDL at 4° C. for 1 h to allow for cell-surface binding (zero time bound ligand). Cells were rinsed three times with cold F12 medium to remove unbound ligands. Prewarmed F12 medium was added; and the cells were incubated at 37° C. for the times indicated. At each point, the cells were again placed on ice, and the culture medium was collected. To 0.5 ml of medium was added 0.4 ml of 0.2% bovine serum albumin (Sigma) and 0.4 ml of 50% trichloroacetic acid (TCA). The medium was then incubated at 4° C. for 30 min and centrifuged at 3,000 rpm for 10 min. The supernatant was collected for $^{125}$I-apoE degradation assay, and the pellet was counted as TCA-precipitable intact $^{125}$I-apoE. The cells were washed once with cold DMEM-Hepes, incubated with 10 mM suramin on ice in a cold room for 30 min, and then dissolved in 0.1 N NaOH. Cellular radioactivity (internalized apoE) was measured with a gamma counter, and protein concentration was determined by Lowry's method.

Results

The cell association of $^{125}$I-β-VLDL or $^{125}$I-β-VLDL enriched with either human apoE3 or apoE4 by Neuro-2a cells was examined at 37° C. (FIG. 5). In these studies, the maximal cell association of β-VLDL alone was ~225 ng/mg cell protein. The cell association of β-VLDL was enhanced ~1.7-fold by apoE3 or apoE4. There was therefore no major isoform-specific difference in the ability of apoE3 or apoE4 to promote the binding and internalization of $^{125}$I-β-VLDL, suggesting that similar amount of β-VLDL was internalized. In addition, DiI-labeled p-VLDL were used to examine the uptake of the β-VLDL particles by Neuro-2a cells (FIG. 6). DiI internalized with lipoproteins is retained by cells and can be used to quantitate the total amount of lipoprotein metabolized (bound, internalized, and degraded). In these studies, at 2 h both apoE3 and apoE4 stimulated the uptake of DiI-labeled β-VLDL (~1.8-2-fold) compared with the amount of DiI-labeled β-VLDL internalized in the absence of apoE [apoE4 stimulated β-VLDL uptake to a slightly greater extent than apoE3 ($p<0.002$)].

Figure 7:
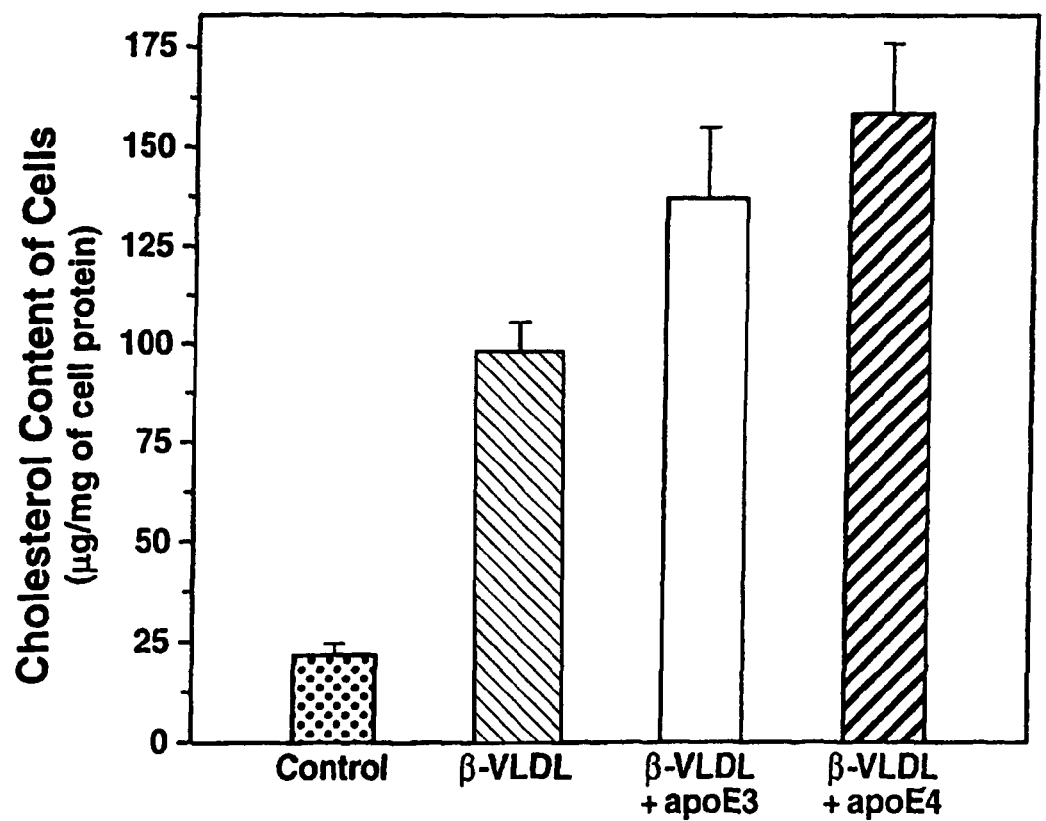
FIG. 7 is a bar graph of the amount of cholesterol in μg/mg of cell protein for the four different types of cells as labeled.

To establish further that apoE3 and apoE4 stimulated similar β-VLDL particle uptake, the cells were incubated in medium alone, medium containing β-VLDL, or medium containing β-VLDL and either apoE3 or apoE4, and the cholesterol content of the cells was determined (FIG. 7). The β-VLDL alone increased the cellular cholesterol content ~4.7-fold, compared with the control cells maintained in the absence of lipoprotein. The β-VLDL enriched with either apoE3 or apoE4 increased the cellular cholesterol content [~1.5-fold and ~1.7-fold, respectively; the cholesterol content with apoE4 was significantly greater ($p<0.005$)] compared with the cells incubated with β-VLDL alone. Free apoE3 or apoE4 added without lipid had essentially no effect on the cellular cholesterol level. Taken together, the results examining the effect of apoE3 and apoE4 on the uptake of $^{125}$I-β-VLDL or DiI-labeled β-VLDL and the ability of the cells to accumulate β-VLDL-derived cholesterol demonstrate that apoE3 and apoE4 stimulate β-VLDL internalization to a similar extent in Neuro-2a cells, with apoE4 being somewhat more active. Differences in lipoprotein particle uptake could not therefore account for the difference in the accumulation of apoE3 versus apoE4 (apoE3 greater than apoE4) in Neuro-2a cells incubated with apoE-enriched β-VLDL.

Example 5

Intracellular Accumulation of ApoE Isoforms

Figure 8:
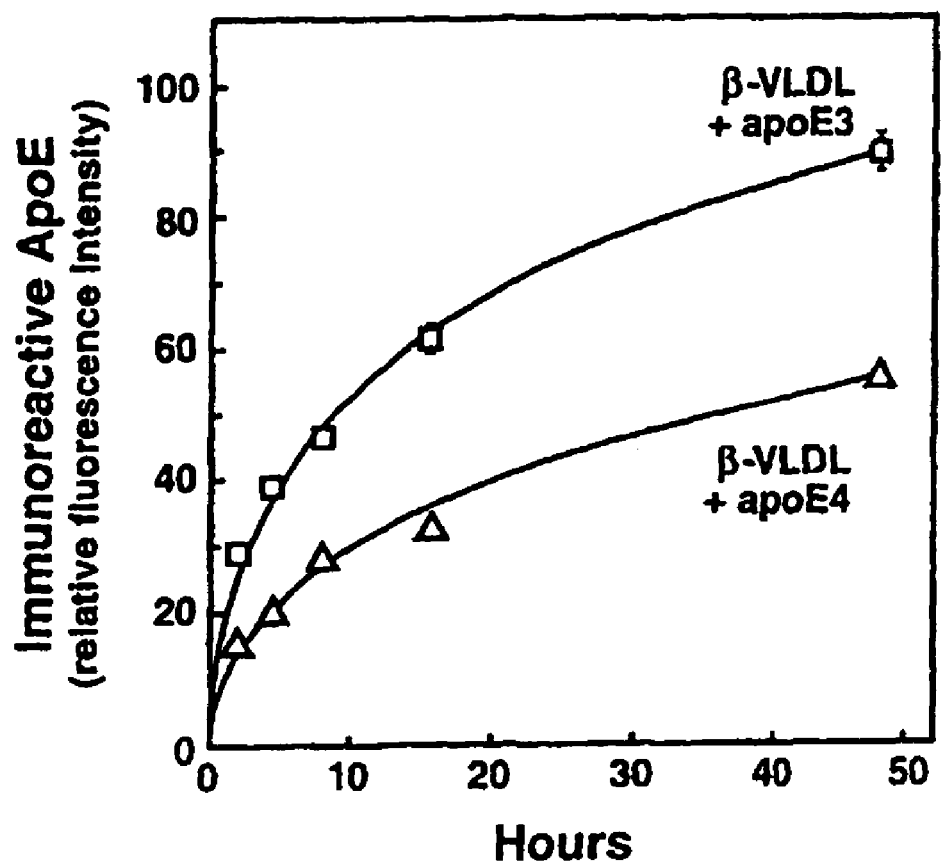
FIG. 8 is a graph of the relative fluorescence intensity of ApoE over time in hours.

The time course for differential accumulation of apoE3 and apoE4 was analyzed in the Neuro-2a cells (FIG. 8). The cells were incubated with apoE-enriched β-VLDL for 2 to 48 h, permeabilized, and processed for immunocytochemistry with a polyclonal antibody that detects purified human apoE3 and E4 equally well on western blots. Immunoreactive apoE was detected and quantitated by confocal microscopy to measure the relative fluorescence intensity. At the earliest time point (2 h), the cells contained approximately 1.8-fold more apoE3 than apoE4. This difference in the level of immunoreactive apoE was maintained for up to 48 h (~1.6-fold more apoE3 than apoE4) (FIG. 8).

The accumulated intracellular apoE was primarily intact protein. Cells were incubated with apoE-enriched β-VLDL for the times indicated; the cellular proteins were extracted, resolved by SDS-PAGE, and transferred to nitrocellulose, and apoE was detected by autoradiography. Autoradiography demonstrated a greater cellular accumulation of apoE3 than apoE4 and no obvious accumulation of degradation products. Western blot analysis yielded similar results, revealing the differential intracellular accumulation of intact apoE.

Figure 9:
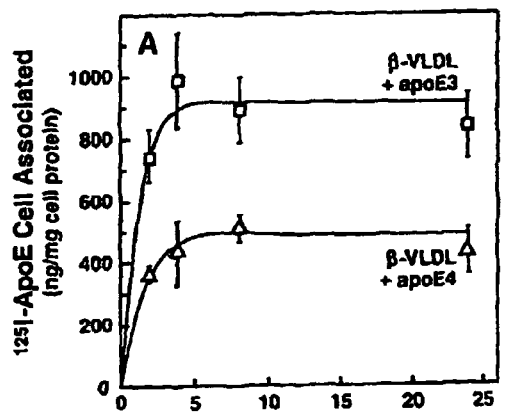
FIG. 9 is a graph of the amount of cell associated $^{125}$I-ApoE over time for two different types of cells.
Figure 10:
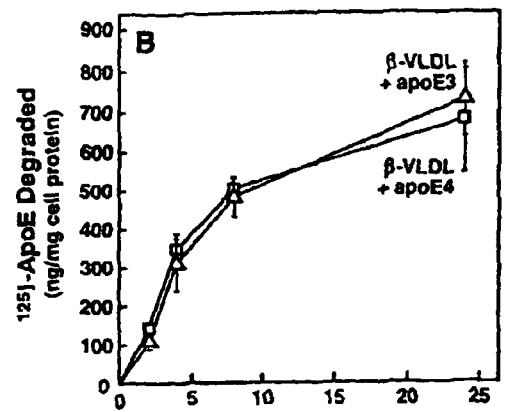
FIG. 10 is a graph of the amount of $^{125}$I-ApoE degraded over time for two different types of cells.
Figure 11:
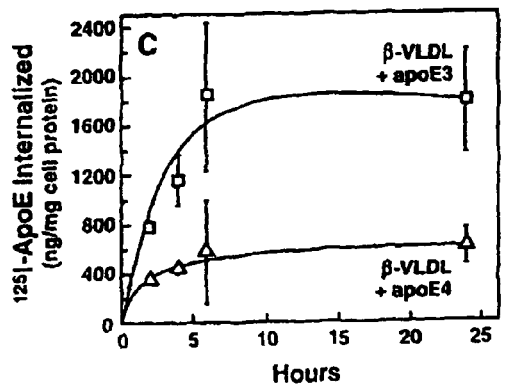
FIG. 11 is a graph of the amount of $^{125}$I-ApoE which is internalized by two different types of cells over time as measured in hours.
Figure 12:
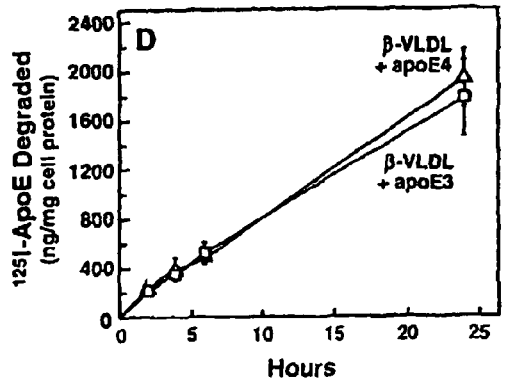
FIG. 12 is a graph of the amount of $^{125}$I-ApoE degraded over time for two different types of cells as measured in hours.

To determine if the difference in accumulation or retention of apoE3 and apoE4 by cells was due to a difference in cell association (binding and internalization) or to a difference in degradation of internalized apoE3 or apoE4, studies were performed using β-VLDL enriched with $^{125}$I-apoE3 or $^{125}$I-apoE4. In these studies, the differential cellular association or internalization of the iodinated apoE3 and apoE4 in both Neuro-2a cells (FIG. 9) and human skin fibroblasts (FIG. 11) was also apparent beginning at the earliest time point (2 h) and continuing to the end of the experiment (24 h). The difference in apoE3 and apoE4 content of the cells was maximal after 4 to 8 h of incubation. In the Neuro-2a cells, the amount of apoE3 associated with the cells was twice the amount of apoE4 associated with the cells (FIG. 9), whereas in fibroblasts apoE3 was threefold more abundant than apoE4 in the cells (FIG. 11). Likewise, $^{125}$I-apoE2 also accumulated intracellularly to a greater extent than apoE4 (~1.5-fold greater than apoE4 at 2 h). In contrast to the differential cell association or internalization of $^{125}$I-apoE3 and $^{125}$I-apoE4 in the Neuro-2a cells and fibroblasts, respectively, there was no significant difference in the degradation of the iodinated apoE3 or apoE4 by the cells (FIGS. 10 and 12).

The differential cellular accumulation of apoE3 and apoE4 from apoE-enriched β-VLDL was also observed in hepatocytes. As shown in Table 6, HepG2 cells incubated with $^{125}$I-apoE3 plus β-VLDL displayed about 2.5-fold greater cell association of apoE compared with cells incubated with $^{125}$I-apoE4 plus β-VLDL. Data from the immunological and autoradiographic studies, as well as the binding and degradation experiments, showed differential accumulation of apoE3 and apoE4 in Neuro-2a cells, fibroblasts, and hepatocytes incubated with apoE3- or apoE4-enriched β-VLDL.

TABLE 6

Cell association of $^{125}$I-apoE3- or $^{125}$I-apoE4-enriched β-VLDL by HepG2 cells

| Time | $^{125}$I-apoE3 (ng/mg cell protein) | $^{125}$I-apoE4 (ng/mg cell protein) |
|---|---|---|
| 4 hours | 1062 ± 171 | 51 ± 10 |
| 8 hours | 1466 ± 38 | 683 ± 6 |

Mean ± S.D. obtained from two independent experiments performed in duplicate.

In the experiments described thus far, the apoE3 and apoE4 were incubated with the β-VLDL at 37° C. for 1 h, and then the mixture was added to the cells. Separation of the mixture by fast-performance liquid chromatography demonstrated that ~50% of the apoE was associated with β-VLDL particles. One possible reason for the differential accumulation might be that more apoE3 than apoE4 associates with the β-VLDL and that more apoE3 is therefore delivered to the cells. This possibility was ruled out by examining the amount of $^{125}$I-apoE3 or $^{125}$I-apoE4 associated with β-VLDL after isolation of apoE-enriched β-VLDL by fast-performance liquid chromatography. In fact, slightly more apoE4 than apoE3 was associated with the lipoprotein particles (7.0 versus 6.1 μg/mg of β-VLDL cholesterol). Furthermore, using the fast-performance liquid chromatography-purified $^{125}$I-apoE-enriched β-VLDL, we demonstrated that the differential apoE accumulation occurred with apoE on the β-VLDL particles and not with lipid-free or lipid-poor apoE. The cell association was greater in Neuro-2a cells incubated with purified $^{125}$I-apoE3-enriched β-VLDL than in those incubated with purified $^{125}$I-apoE4-enriched β-VLDL (58 versus 39 ng/mg of cell protein at 2 h; 101 versus 65 ng/mg of cell protein at 4 h).

Example 6

Mechanisms Responsible for Differential Accumulation of ApoE Isoforms

To explore in more detail how differential processing of apoE3 versus apoE4 could explain the differential accumulation, we examined the internalization of iodinated apoE-enriched β-VLDL by fibroblasts and Neuro-2a cells at 18° C., a temperature at which lipoprotein internalization occurs but degradation does not (FIGS. 13 and 14). Analysis of the culture medium for degradation products of the $^{125}$I-apoE confirmed that degradation did not occur under the conditions used. In these studies, apoE3 accumulated to a greater extent than apoE4 in both fibroblasts (FIG. 13) and neurons (FIG. 14), demonstrating that the differential accumulation was due to differential handling of at least a portion of the internalized apoE and not to differences in lysosomal degradation. This conclusion was supported by studies in fibroblasts, in which degradation was blocked by chloroquine. Even in the absence of lysosomal degradation, the differential accumulation of apoE3 and apoE4 was apparent when the cells were incubated with apoE3- or apoE4-enriched β-VLDL.

Figure 15:
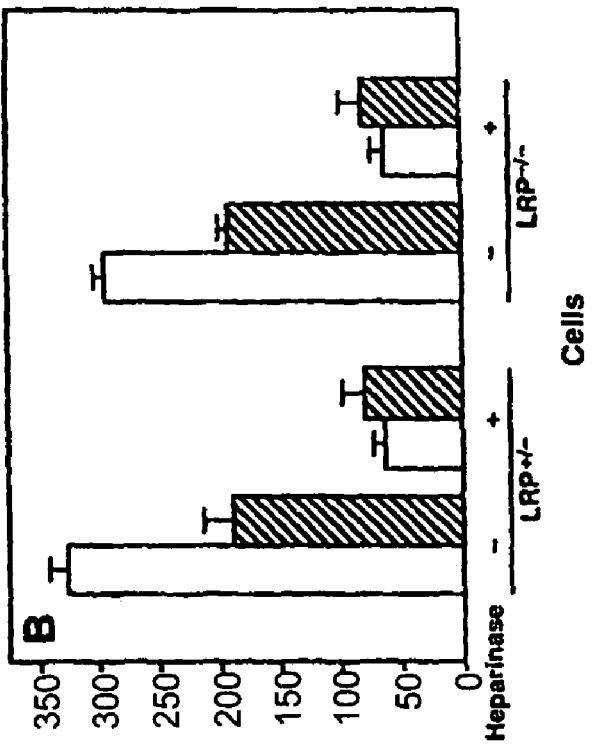
FIG. 15 is a bar graph of the amount of $^{125}$I-ApoE internalized by human fibroblasts expressing or lacking the LDL receptor.
Figure 16:
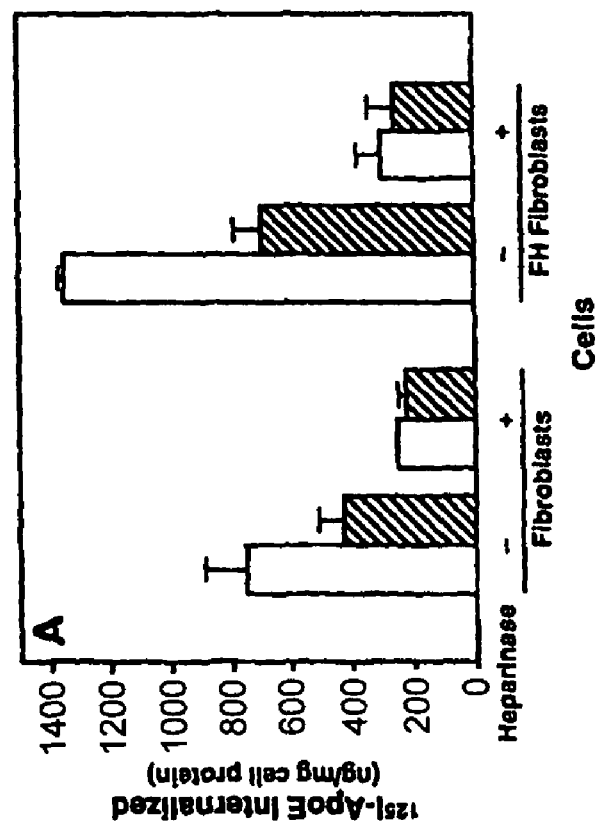
FIG. 16 is a bar graph of the amount of $^{125}$I-ApoE internalized by two different types of cells expressing or lacking LRP.

To identify the mechanism of the differential cellular accumulation of apoE3 and apoE4, we made use of fibroblasts that lacked expression of the LDL receptor, the LRP, or specific cell-surface proteoglycans. The differential cellular accumulation of the apoE3 and apoE4 from apoE-enriched β-VLDL occurred in both LDL receptor-expressing and LDL receptor-negative fibroblasts, demonstrating that the LDL receptor was not involved in the differential accumulation (FIG. 15). On the other hand, the differential accumulation was blocked totally by prior treatment of the normal or FH fibroblasts with heparinase, and the total cell association was significantly decreased for both isoforms, suggesting that the differential effect might be mediated either by the HSPG/LRP complex or by HSPG alone (FIG. 15). As shown in FIG. 16, embryonic mouse fibroblasts either heterozygous for LRP expression (LRP$^{+/-}$) or lacking LRP expression (LRP$^{-/-}$) displayed differential accumulation of apoE3 and apoE4. Therefore, LRP expression is not required for the differential accumulation of apoE3 versus apoE4. However, heparinase treatment of these cells blocked the effect, again indicating a role for cell-surface HSPG (FIG. 16). As indicated, heparinase markedly decreased total internalization of both apoE3- and apoE4-enriched β-VLDL, further suggesting the importance of HSPG alone in mediating the enhanced metabolism of apoE-enriched lipoproteins.

Figure 17:
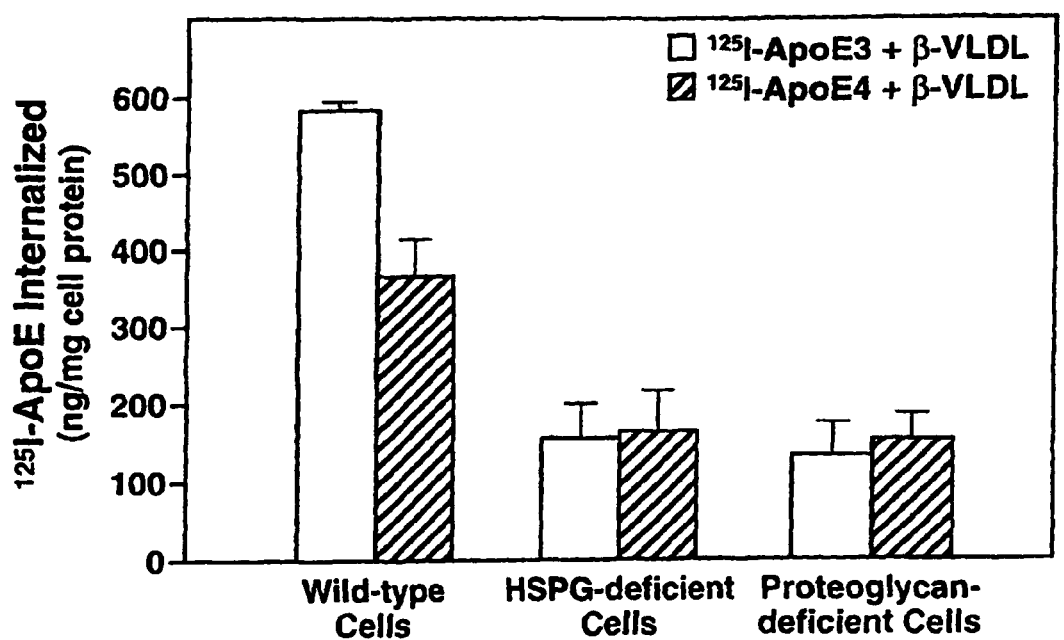
FIG. 17 is a bar graph of the amount of $^{125}$I-ApoE internalized for the different types of cells as labeled.

The role of HSPG in the apoE3 and apoE4 differential accumulation was examined further in control CHO cells, in mutant CHO cells specifically lacking HSPG expression, and in CHO cells lacking expression of all proteoglycans (FIG. 17). The differential cellular accumulation or retention of $^{125}$I-apoE3 versus $^{125}$I-apoE4 was apparent in the wild-type CHO cells; however, the differential accumulation or retention was completely abolished in both the HSPG-deficient and the proteoglycan-deficient CHO cells, conclusively demonstrating the importance of cell-surface HSPG in this process. Likewise, the levels of apoE3 and apoE4 internalized by the CHO mutant cells were very significantly reduced.

Figure 18:
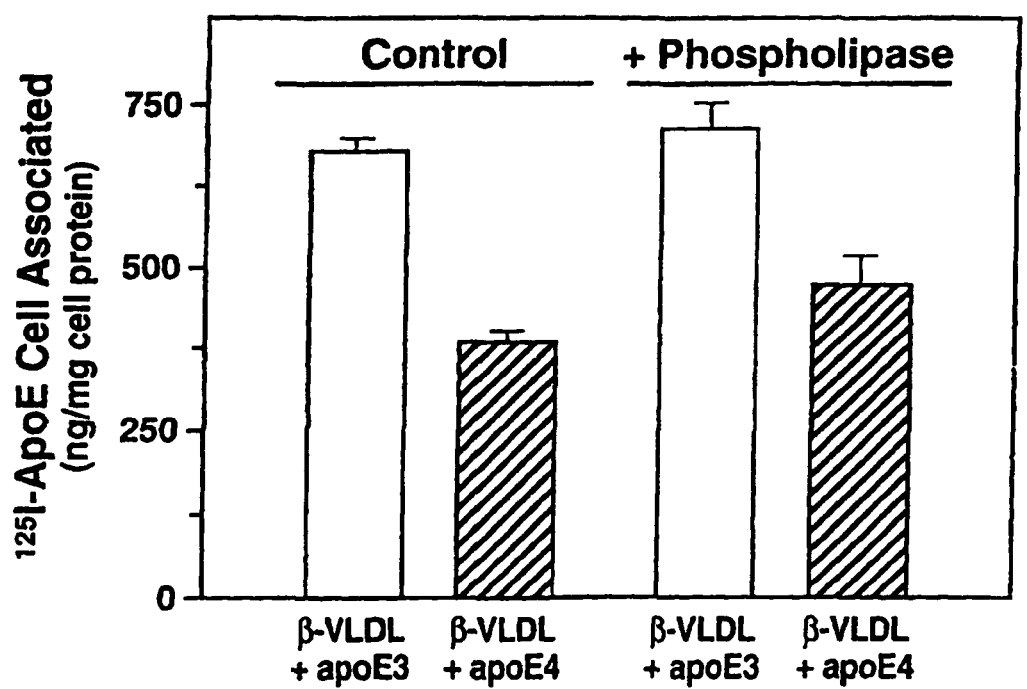
FIG. 18 is a bar graph of $^{125}$I-ApoE associated with the different types of cells as labeled.

Proteoglycans associate with cell membranes either by glycerophosphatidylinositol (GPI) anchors or by transmembrane spanning of their core proteins. These classes of proteoglycans undergo different rates of cellular processing. The GPI-anchored proteoglycans exhibit fast endosome to lysosome transport and undergo lysosomal degradation with an intracellular half-life of ~30 min, whereas the core protein-anchored proteoglycans exhibit slow endosome to lysosome transport (half-life ~4 h) and undergo delayed processing. The retention of apoE by the cells would be consistent with use of the slow pathway for endosome to lysosome transport and would suggest that the differential accumulation of apoE3 and apoE4 in the cells is not due to internalization of apoE with GPI-anchored proteoglycans. This was demonstrated by examining the effect of specific phospholipase C, which removes GPI-anchored HSPG, on the cell association of iodinated apoE-enriched β-VLDL with fibroblasts (FIG. 18). Under the conditions used, the phospholipase removed ~15% of $^{35}$S from cells labeled for 24 h with [$^{35}$S]O$_4$. Specific phospholipase C treatment of the cells did not affect the differential accumulation of apoE3 and apoE4 in the cells or the total binding and internalization of either the apoE3- or apoE4-enriched β-VLDL, demonstrating that GPI-anchored HSPG were not involved (FIG. 18).

Consideration was given to the possibility that the apoE4 isoform differential resulted from shunting of apoE3 specifically into an intracellular compartment and/or retroendocytosis or retarded internalization of apoE4. To evaluate these possibilities, we conducted a modified A pulse-chase@ study in which CHO cells were incubated with $^{125}$I-apoE-enriched β-VLDL for 1 h at 4° C., washed to remove unbound lipoproteins, and then warmed to 37° C. for various times to follow internalization, degradation, and retention (see Materials and Methods). At the specific times, the medium was removed for analysis of both degradation products (degraded apoE) and TCA-precipitable proteins (released intact apoE), and the cells were washed with suramin (suramin-releasable apoE) and then counted (internalized apoE).

Table 7 shows that the amount of apoE3 and apoE4 bound at 4° C. (zero time) was similar; however, the amount of apoE3 in the cells (internalized=accumulated or retained) after 30, 60, and 120 min at 37° C. was approximately twofold greater than the amount of apoE4. At each time point, we found a small amount of the $^{125}$I-apoE that was suramin-releasable (i.e., apoE present on the cell surface). Between 30 and 120 min, the amount of $^{125}$I-apoE3 and apoE4 degraded increased and was approximately equal for both isoforms. Thus, similar fractions of internalized apoE3 and apoE4 were degraded. Of interest was the greater amount of apoE4 that appeared in the medium during the incubation period, especially at 30 and 60 min. This TCA-precipitable, intact apoE could represent apoE that is retroendocytosed or is on or near the cell surface and rapidly released upon warming. Thus, with time apoE4 is released to a greater extent or internalized to a lesser extent than apoE3 or, alternatively, more apoE3 is sequestered into a compartment and unavailable to be released. Therefore, more apoE3 accumulates and is retained by the cells. Typically, 80-90% of the total apoE bound to the cells at 4° C. at zero time was recovered in the various fractions of the medium and cells after the warm-up periods (Table 7).

TABLE 7

Metabolism of $^{125}$I-apoE3- and $^{125}$I-apoE4-enriched β-VLDL by Wild-type CHO Cells

| | 30 min | | 60 min | | 120 min | |
|---|---|---|---|---|---|---|
| | ApoE3 | ApoE4 | ApoE3 | ApoE4 | ApoE3 | ApoE4 |
| | | | (ng/mg cell protein) | | | |
| Internalized (retained) | 157 | 84 | 123 | 55 | 78 | 27 |
| Suramin-releasable (cell surface) | 45 | 27 | 39 | 10 | 12 | 10 |
| Degraded | 15 | 12 | 34 | 35 | 45 | 43 |
| TCA-precipitable (released intact) | 182 | 245 | 181 | 238 | 232 | 225 |
| Total | 399 | 368 | 377 | 338 | 367 | 305 |

Similar amounts of $^{125}$I-apoE3 and $^{125}$I-apoE4 (399 ng/mg and 378 ng/mg of cell protein, respectively) were bound to the cells at 4° C. (i.e., zero time). Recovery of $^{125}$I-apoE (total) in the fractions analyzed after warming to 37° C. is also reported in the table. Data represent results from one experiment performed in quadruplicate. The experiment was repeated three times with similar results.

Data from this pulse-chase study are graphically illustrated in FIG. 19. Three separate experiments were performed with this design and yielded comparable results. In wild-type CHO cells, apoE3 accumulated and was retained to a greater extent than apoE4, similar amounts of apoE3 and apoE4 were degraded at all time points, and more apoE4 reappeared in the medium at 30 and 60 min. By contrast, HSPG-deficient CHO cells bound much less $^{125}$I-apoE3+β-VLDL and $^{125}$I-apoE4+β-VLDL (77 and 75 ng/mg of cell protein) than wild-type CHO cells (399 and 378 ng/mg of cell protein); the HSPG-deficient cells internalized and degraded similar amounts of apoE3 and apoE4 at all time points. Similar amounts of suramin-releasable and TCA-precipitable $^{125}$I-apoE3 and $^{125}$I-apoE4 (FIG. 10B) were also found. Thus, HSPG-deficient cells not only have markedly reduced uptake of apoE but also do not show any isoform-specific differential accumulation, degradation, or retention.

The metabolism of apoE-enriched β-VLDL was examined to determine if apoE3 and apoE4 stimulate the same level of uptake of β-VLDL particles. Further, the cellular uptake (retention or accumulation) or the apoE from apoE-enriched β-VLDL is examined more directly by immunocytochemistry and by following the metabolism of iodinated apoE.

Incubation of Neuro-2a cells with either apoE3- or apoE4-enriched β-VLDL resulted in a similar cell association of β-VLDL and a similar increase of cellular cholesterol. This shows that in neurons, as in fibroblasts, apoE3 and apoE4 stimulate the uptake of similar numbers of lipoprotein particles. On the other hand, when the cellular accumulation specifically of apoE3 and apoE4 was examined in Neuro-2a cells by either immunofluorescence or analysis of extracted cellular proteins, a differential accumulation of apoE3 and apoE4 was observed. These observations were confirmed in Neuro-2a cells and extended to fibroblasts and hepatocytes by examining the cellular association of internalization of $^{125}$I-apoE3- or $^{125}$I-apoE4-enriched β-VLDL. In all three cell types, intracellular apoE3 accumulated to a greater extent than apoE4 (~2-fold). Likewise, apoE2 also accumulated to a greater extent than apoE4 in Neuro-2a cells (~1.5-fold). The differential accumulation of apoE3 and apoE4 occurred in both LDL receptor-negative human fibroblasts and in LRP-negative murine embryonic fibroblasts, demonstrating that these receptors are not significantly involved. However, the differential accumulation or retention was abolished by treating the cells with heparinase.

The role of the HSPG in this process was confirmed by the use of mutant CHO cells deficient in HSPG synthesis. In these cells, the accumulation of both apoE3 and apoE4 was reduced, and the differential accumulation of apoE3 and apoE4 was abolished. Treatment of the cells with specific phospholipase C, which releases phospholipid-anchored HSPG, had no effect on the differential accumulation of apoE3 and apoE4 from apoE-enriched β-VLDL. Enhanced degradation of apoE4 was not the reason for the difference in cellular accumulation of apoE3 and apoE4 by the cells, since the differential accumulation occurred at 18° C., a temperature at which endosome-lysosome fusion does not occur, as well as in the presence of chloroquine, which inhibits lysosomal degradation.

The pulse-chase studies (Table 7, FIGS. 19 and 20) suggest a possible mechanism for the differential accumulation or retention of apoE. After similar amounts of $^{125}$I-apoE3- and $^{125}$I-apoE4-enriched β-VLDL were bound to the CHO cells at 4° C., warming the cells to 37° C. resulted in internalization of more apoE3 than of apoE4. On the other hand, more apoE4 was found in the medium at the early time points (30 and 60 min) suggesting that the differential apoE accumulation and retention resulted from a preferential release of apoE4 from the cells. In these same studies, the HSPG-deficient CHO cells bound, internalized, and degraded much less apoE, and there was no differential between apoE3 and apoE4.

Cell-surface HSPG bind a number of biologically important molecules. In addition, HSPG can function as a receptor directly involved in binding and internalization of specific ligands. This has been demonstrated for certain viruses, thrombospondin, lipoprotein and hepatic lipases, thrombin, and fibroblast growth factor (FGF). In addition, HSPG facilitates the interaction of ligands with other receptors or serve as a bridge functioning like a co-receptor. For example, HSPG can facilitate the interaction of FGF with the FGF receptor, a co-receptor function for HSPG and the LRP in the binding and internalization of apoE- and hepatic lipase-containing lipoproteins. As demonstrated in the present study, apoE-containing lipoproteins can be bound and apoE internalized in an HSPG-dependent process without participation of the LDL receptor or the LRP. Heparinase treatment alone abolishes the differential accumulation of apoE. Heparinase treatment of cultured cells does not interfere with LDL receptor-mediated LDL binding or LRP-mediated binding of $α_2$-macroglobulin.

The ability of HSPG alone or in complex with a co-receptor to function in the internalization of ligands suggests ways in which the intracellular processing of these molecules may differ. The intracellular fate of FGF is determined by which pathway is used. When FGF is internalized by HSPG alone, it is degraded; however, when FGF is internalized via the HSPG/FGF receptor pathway, a portion of the FGF enters the cytoplasm and ultimately the nucleus. Clearly, apoE-enriched lipoproteins can be internalized by three cellular mechanisms: the LDL receptor, the HSPG/LRP pathway, and an HSPG-dependent/LRP-independent pathway. Thus, the intracellular fate of apoE may depend on the proportion of the protein entering the cell via each of these pathways. Specifically, the HSPG-dependent/LRP-independent pathway accounts for the differential handling of apoE3 versus apoE4 that is responsible for the greater accumulation of apoE3 than apoE4. One can speculate that apoE3-enriched lipoprotein uptake via the HSPG pathway directs apoE3 to a separate (intracellularly sequestered) pool, allowing it to accumulate in the cells. On the other hand, apoE4-enriched lipoproteins taken up via the HSPG pathway may fail to escape the typical endosomal/lysosomal cascade and thus apoE4 does not accumulate. Alternatively, apoE4 complexed to HSPG may be recycled and released at the cell surface (retroendocytosis).

Results provided here show that incubation of neurons, fibroblasts, and hepatocytes with β-VLDL together with either apoE3 or apoE4 results in the retention of intact apoE by the cells and in a greater cellular accumulation of apoE3 than apoE4. Cell-surface HSPG appear to play a primary role in both the retention and the apoE and the differential accumulation of apoE3 versus apoE4. The LRP and the LDL receptor are not primarily involved. The intracellular fate of the apoE remains to be determined; however, the retention of apoE by the cells is most likely due to association with the slow endosome to lysosome transport of HSPG. It remains to be determined whether or not apoE in this pathway can escape lysosomal degradation and enter the cytoplasmic compartment, where it might interact with microtubule-associated proteins or other cellular components that could account for the differential effects of apoE3 and apoE4 on neurite outgrowth and the cytoskeleton.

Example 7

Identification of Compounds that Interfere with Domain Interactions

Small organic molecules were identified that block the domain interaction in ApoE4 and reverse the enhanced risk associated with this isoform. The strategy used to identify the molecules was to use available structural information to narrow the choices for physical testing. The recently determined structure of the N-terminal domain of human apoE4 provided an exciting opportunity for structure-based drug design. The general approach was to find molecules which bind to the appropriate region of the N-terminal domain and block the interaction with the C-terminal domain, a "negative image" approach. The Available Chemicals Directory (ACD; Molecular Design Limited, Inc., San Leandro, Calif.) has been screened computationally using the structure of the N-terminal domain of human apoE4. The ACD contains model-built coordinates of over 200,000 compounds available from chemical suppliers.

Search Methods—Negative Image Approach

In the negative image approach, the program DOCK models the binding of each candidate molecule to the target protein. Kuntz, I. D. (1992) *Science* 257; 1078-82; and Ewing and Kuntz (1997) *J Comput. Chem.* 18:1175-1189. The space available for binding is described by a set of spheres that collectively fill the site. The centers of the spheres are then treated as possible ligand atom positions, and each molecule is combinatorially placed in the site in hundreds to thousands of positions. Simple scoring functions, one reflecting shape complementarity and another consisting of a Lennard-Jones van der Waals term and a Coulombic electrostatic term, are used to evaluate the positions. Precalculated grids allow rapid scoring. Meng et al. (1992) *J. Comput. Chem.* 13:505-524. For each molecule, the best position according to each scoring function is saved. At the end of the process, the several hundred best-scoring molecules according to each function are examined graphically. Kuntz and coworkers have applied the DOCK strategy to several targets, including the HIV 1 protease and thymidylate synthase.

DOCK Search

DOCK version 4.0 was used to search the ACD against the N-terminal domain structures of both apoE3 and ApoE4. Kuntz (1997) *J. Comput. Chem.* 18:1175-1189. The site of interest included residues 109, 112, and 61, plus surrounding regions. All protein atoms in the structure were used in computing scores. Searches were performed at two different levels of sampling (roughly, this corresponds to how many positions are tried for each molecule).

Over 2000 molecules that scored well when docked to apoE4 were output from DOCK. In most cases, molecules that also appeared on the corresponding lists for apoE3 were removed from consideration. Compounds were further screened visually using the graphics program MIDAS, by evaluation of complementarity with the target site and the presence of desired druglike characteristics. Ferrin et al. (1988). *J. Mol. Graph.* 6:13-27; and Lipinski et al. (1997) *Adv. Drug Delivery Rev.* 23:3-25. For example, molecules that were too large, hydrophobic, or peptide-like were removed from consideration. Natural products with a large number of stereocenters were also discarded, as they would not be amenable to synthesis of derivatives. This process led to a list of 115 compounds, with 65 initial recommendations (one per set of close analogs).

Assay for Domain Interaction

Since apoE4 displays a preference for large triglyceride-rich lipoprotein particles that is mediated by domain interaction, an emulsion binding assay was developed to test the candidate compounds for their ability to interfere with domain interaction.

Preparation of emulsion particles. Triolein (160 mg) and L-alpha-Phosphatidylcholine (40 mg) are combined and dried under nitrogen. After the addition of 8 mls of buffer (10 mM Tris, 100 mM KCl, 1 mM EDTA, pH 8.0), the mixture is sonicated in a water bath to obtain a heterogeneous mix of emulsion particles. The particles are harvested by ultracentrifugation (TLA 100.2 rotor, 30,000 rpm for 30 minutes) and the subsequent lipid cake is removed by tube slicing and resuspended in 100 µt 20 mM Phosphate Buffer (PB). Triolein and phospholipid content are measured and total emulsion particle concentration is determined.

Radiolabelling Freshly denatured and renatured Apolipoprotein E3 and E4 are radiolabelled using Bolton-Hunter Reagent [$^{125}$I] (ICN). Specific Activity is determined using Lowry method and Gamma 8000 counter.

Binding Affinity Assay. The binding affinity of apoE3 and apoE4 to emulsion particles was determined as follows. In glass tubes, 25 µg of protein (with iodinated tracer) was reduced with 1% β-mercaptoethanol. Two hundred and fifty µg of emulsion particles and 2.5 µl of compound (10 mM stock) were added and the final mixture was brought up to 250 µl with 20 mM phosphate buffer (PB). The reaction mixture was then incubated in a 37° C. water bath for 2 hours before being transferred to 1.5 ml ultracentrifuge tubes. Finally, 50 µl of 60% sucrose was mixed with the sample and 400 µl 20 mM PB was carefully layered on top. Using a TLA 100.2 rotor, the tube was spun at 30,000 rpm for 30 minutes and subsequently cut to separate the floating emulsion particle layer from the free protein at the bottom of the tube. These fractions were then combined with the respective half of the actual tube and counted using a Gamma-8000. From these results, total emulsion-bound protein was compared to total free protein. Protein-only assays yielded 94.5-96.6% of protein accumulated in the bottom portion of the tube. In emulsion particle-only assays, 94% of emulsion particles accumulated in the top portion of the tube.

Control binding assays were conducted without the addition of compounds to determine recovery and apoE3 and apoE4 respective affinity for emulsion particles. Table 8 shows the results.

TABLE 8

|  | Apo E3, n = 9 %(bound/free) | Apo E4, n = 9 %(bound/free) |
|---|---|---|
| Mean | 29.8/70.2 | 59.4/40.6 |
| Range | 20-39/61-81 | 50-70/30-50 |
| Median | 33/67 | 60/40 |
| Mean | 92% | 88% |

Once the Apo E3 and E4 binding affinity had been determined, assays including the DOCK compounds were conducted. ApoE4 controls were included in the initial assay and apoE3 and apoE4 controls were included in the follow up assay.

In an initial screen, 14 compounds interfered with domain interaction and 6 partially interfered. In a follow-up assay, 8 of the 14 compounds were confirmed to interfere with domain interaction with little or no effect on the binding of apoE3 to the emulsions. Table 9 shows the results of the eight compounds that interfere with domain interaction. Values are provided as % bound/% free of either apoE4 ("E4") or apoE3 ("E3").

TABLE 9

| Compound | Supplier | Cat. # | Family | E4 + cpd | E4 control | E4 + cpd n = 3 | E4 control | E3 control n = 4 | E3 + compound |
|---|---|---|---|---|---|---|---|---|---|
| Z-D-Tyr (BZL)-OH | Bachem | C-1415 | blocked amino acid | 25/75 23/77 | 69/31 62/38 | 57/43 | 43/57 | 33.5/66.5 | 26/74 |
| Azocarmine G | Acros | 40157-0250 | disulfonate | 12/88 15/85 | 49/51 53/47 | 57/43 | 46/54 | 33.5/66.5 | 30/70 |
| Glycine cresol red | Fluka | 50100 | dye | 29/71 23/77 | 57/43 48/52 | 57/43 | 48/52 | 33.5/66.5 | 33/67 |
| Erythrosin B | ICN | 190450 | dye | 11/89 10/90 | 57/43 48/52 | 57/43 | 26/74 | 33.5/66.5 | 20/80 |
| 5-chloro-2-(4-chloro-2-(3,4-dichloro phenylureido | Aldrich | S39863-2 | monosulfanate | 22/78 19/81 | 57/43 48/52 | 57/43 | 49/51 | 33.5/66.5 | 14/86 |
| RCL S19, 214-7 | Aldrich | S19214-7 | mono-sulfoalkyl compound | 33/67 36/64 | 57/43 59/41 | 57/43 | 48/52 | 33.5/66.5 | 29/71 |

TABLE 9-continued

| Compound | Supplier | Cat. # | Family | E4 + cpd | E4 control | E4 + cpd n = 3 | E4 control | E3 control n = 4 | E3 + compound |
|---|---|---|---|---|---|---|---|---|---|
| 3-butyl-1-ethyl-5-(2-(3-sulfobutyl-benzo(1,3)oxazo | Synthon | ST-342 | mono-sulfoalkyl compound | 28/72 21/79 | 60/40 60/40 | 57/43 | 45/55 | 33.5/66.5 | 30/70 |
| RCL S3, 301-5 | Aldrich | S03301-5 | misc. | 19/81 18/82 | 59/41 57/43 | 57/43 | 38/62 | 33.5/66.5 | 26/74 |

Example 8

Effects of apoE4 on Aβ Production

Aβ production assay. Stable neuroblastoma B103 cell lines transfected with a wildtype hAPP cDNA construct (B 103-APP) were selected by growing them in Dulbecco's modified Eagle's medium (DMEM) containing 10% fetal calf serum (FBS) and 400 µg/ml G418. A cell line expressing APP at similar levels in mouse brains has been identified by RNase protection assay (RPA) and was used in the studies described below. To determine Aβ production, B103-APP cells were incubated with serum-free minimal essential medium (MEM) containing N2 supplements with or without apoE isoforms for 24 h at 37° C. After incubation, 50 µl of medium was collected and assayed for Aβ levels with an ELISA method. The cells were lysed, and cellular proteins were determined by the Lowry method. AP production was normalized to cellular protein.

Effects of cellular cholesterol on APP processing and Aβ production. Recent studies indicate that the cholesterol-lowering drugs called statins decrease Aβ production in an animal model and lower the risk for AD in human population. Both in vivo and in vitro studies have also shown that cholesterol delivery to cells increases Aβ production. Using this knowledge, it was determined whether the rat neuroblastoma B103 cells stably transfected with the human amyloid precursor protein (APP) (B103-APP) can be used as a cellular tool to study the effects of some reagents, such as apoE isoforms, on APP processing and Aβ production. When the cholesterol level in B103-APP cells was increased by incubation with the cholesterol-rich lipoprotein β-VLDL, the secretion of APPα decreased and the production of Aβ increased. In contrast, when cellular cholesterol was lowered by the HMG-CoA reductase inhibitor lovastatin, the secretion of APPα increased and production of Aβ decreased. These data are consistent with the idea that cellular cholesterol level is critical for Aβ production and that higher cellular cholesterol decreases a-secretase activity and therefore increases Aβ production. Thus, the B103-APP cell line is proved to be a useful cell line to study APP processing and Aβ production.

Effects of apoE isoforms on APP processing and Aβ production. Many studies suggest that apoE has isoform-specific effects on the deposition and clearance of Aβ. Few studies, however, focus on whether apoE also influences APP processing and Aβ production. A major role for apoE is to transport cholesterol into cells. Therefore, apoE may modulate Aβ production by altering cellular cholesterol content. The effects of β-VLDL with or without apoE4 or apoE3 on Aβ production were examined. The results are shown in FIGS. 21A-D. Incubation of cultured B103-APP cells with apoE3- or apoE4-enriched rabbit β-VLDL stimulated Aβ production by comparison to cells incubated without lipoproteins or with β-VLDL alone. However, when apoE-enriched β-VLDL was fractionated by FPLC into two distinct fractions (a large β-VLDL fraction and a smaller lipid-poor apoE-containing fraction) (FIG. 21A), β-VLDL and β-VLDL-enriched in either apoE3 or apoE4 stimulated Aβ production to the same extent (FIG. 21B), even though there was no difference in the cholesterol content of the treated cells. These results suggest that β-VLDL and β-VLDL containing apoE3 or apoE4 increase cellular cholesterol content, which in turn increases Aβ production; however, enrichment of β-VLDL with apoE3 or apoE4 has no further effect on Aβ production.

On the other hand, lipid-poor apoE fractions increased Aβ production in an isoform-specific manner, with apoE4 being more active than apoE3 (FIG. 21C). This isoform-specific effect was further confirmed by treating cells with lipid-free apoE. Lipid-free apoE3 increased Aβ production by 30% and lipid-free apoE4 increased Aβ production by nearly 70% (FIG. 21D). Since the cellular cholesterol content was not changed by lipid-free apoE, these data suggest that the isoform-specific effect of apoE on Aβ production may be not mediated by changing the cellular content of cholesterol. In other words, apoE and cholesterol may regulate Aβ production by different mechanisms.

To explore the possible mechanisms responsible for the isoform-specific effects of apoE on Aβ production, it was determined whether apoE isoforms interact with Aβ and prevent its degradation differentially, thereby retaining different amounts of Aβ in the media. $^{125}$I-labeled Aβ (350 pg/ml) was incubated with or without apoE3 or apoE4 with neo-transfected B103 cells. The cell association and degradation of Aβ was unchanged after a 24-h incubation. Furthermore, apoE3 and E4 had no effect on APPα secretion and α-secretase activity. Similarly, apoE3 and apoE4 did not affect α-secretase activity enzymatically in whole-cell lysates.

Differential effect of apoE3 and apoE4 on APP recycling Since the majority of secreted Aβ is generated within the endosomal pathway when mature APP recycles back to the cell surface, it is possible that apoE3 and E4 stimulate Aβ production by differentially affecting APP recycling. In support of this hypothesis, inhibition of endocytosis by growing cells at 22° C. completely abolished the isoform-specific effects of apoE on Aβ production. To confirm further the effects of apoE on APP recycling, an internalization assay was performed. Cell-surface APP was detected by measuring the radioactivity associated with an APP amino-terminal antibody (1 G7) bound to the cell surface and then released after a 30-minute incubation with an acetic acid. The intracellular APP was detected by measuring radiolabeled 1G7 in cell lysates, and the ratio of intracellular to cell-surface APP was calculated. ApoE increased the internalization of APP in an isoform-specific manner, with apoE4 being more effective than E3. The increased rate of APP internalization may provide more APP for α-secretase and therefore generate more Aβ.

LRP may mediate the apoE4 enhancement of Aβ production. ApoE is a ligand for many cell-surface receptors, including the LDL receptor, LDL receptor-related protein (LRP), heparan sulfate proteoglycans (HSPG), the VLDL receptor, and the apoE receptor-2. Therefore, the receptor responsible for mediating the stimulatory effect of apoE4 on Aβ production was investigated. Receptor associated protein (RAP) is an LRP antagonist. B103-APP cells were pre-incubated without or with RAP at a low concentration (25 nM), which blocks the LRP pathway, or a high concentration (1 µM), which blocks both the LRP and the LDL receptor pathway, at 37° C. for 1 hour and then were further incubated with apoE3 or apoE4 (7.5 µg/ml) for 24 hours. A low concentration of RAP (25 nM), which at least partially blocks the LRP pathway, abolished the apoE4 enhancement of Aβ production, suggesting the potential involvement of the LRP pathway. Interestingly, a high concentration of RAP (1 µM), which blocks both the LRP and the LDL receptor pathways, had a similar effect as the low concentration of RAP, suggesting that the LDL receptor pathway may not be involved in apoE enhancement of Aβ production.

ApoE4 domain interaction may be responsible for apoE4 enhancement of Aβ production. Interaction between the carboxyl- and amino-terminal domains is a unique biophysical property of apoE4. The apoE isoforms differ in their lipoprotein-binding preference: apoE2 and apoE3 prefer HDL, whereas apoE4 prefers VLDL. It is this domain interaction that determines the VLDL preference of apoE4. Arg-112 in apoE4 likely reorients the side chain of Arg-61 from the position it occupies in apoE2 and apoE3, allowing it to form a salt bridge with Glu-255. In apoE2 and apoE3, Arg-61 has a different conformation, and domain interaction does not occur. Only human apoE has Arg-61; the 17 other species in which the apoE gene has been sequenced all have Thr-61. Mutation of Arg-61 to threonine or Glu-255 to alanine in apoE4 prevents domain interaction and converts apoE4 to a form that, like apoE3, binds preferentially to HDL.

Whether domain interaction is required for apoE4 to stimulate Aβ production was investigated. B103-APP cells were incubated with apoE4(Arg-61→Thr) (7.5 µg/ml), which lacks intramolecular domain interaction, at 37° C. for 24 hours. Aβ production was determined and compared with that obtained from the B103-APP cells incubated with apoE3 or apoE4 (7.5 µg/ml). This study demonstrated that replacement of Arg-61 with threonine abolished the enhanced Aβ production, suggesting that apoE4 domain interaction involves in stimulating Aβ production.

Identification of small molecules that disrupt apoE4 domain interaction. As discussed in Example 7, the DOCK program was used to identify small molecules (molecular weight, ~500-600) that interact with apoE4 and disrupt domain interaction, as determined with an in vitro lipoprotein distribution assay. DOCK, a computer-modeling program developed at the University of California, San Francisco for rational drug design, contains model-built coordinates for over 200,000 compounds. The crystallographic structures of apoE3 and apoE4 in the region where apoE4 domain interaction is postulated to occur (critical residues 61, 109, and 112 and surrounding residues) were searched for complementarity with 200,000 compounds in the Available Chemical Directory to identify small molecules docking specifically with apoE4. Approximately 2000 molecules scored well when docked to apoE4; this number was reduced to 60 molecules by visual evaluation of the molecular fit, and about a dozen have been chosen for more extensive studies.

Figure 22:
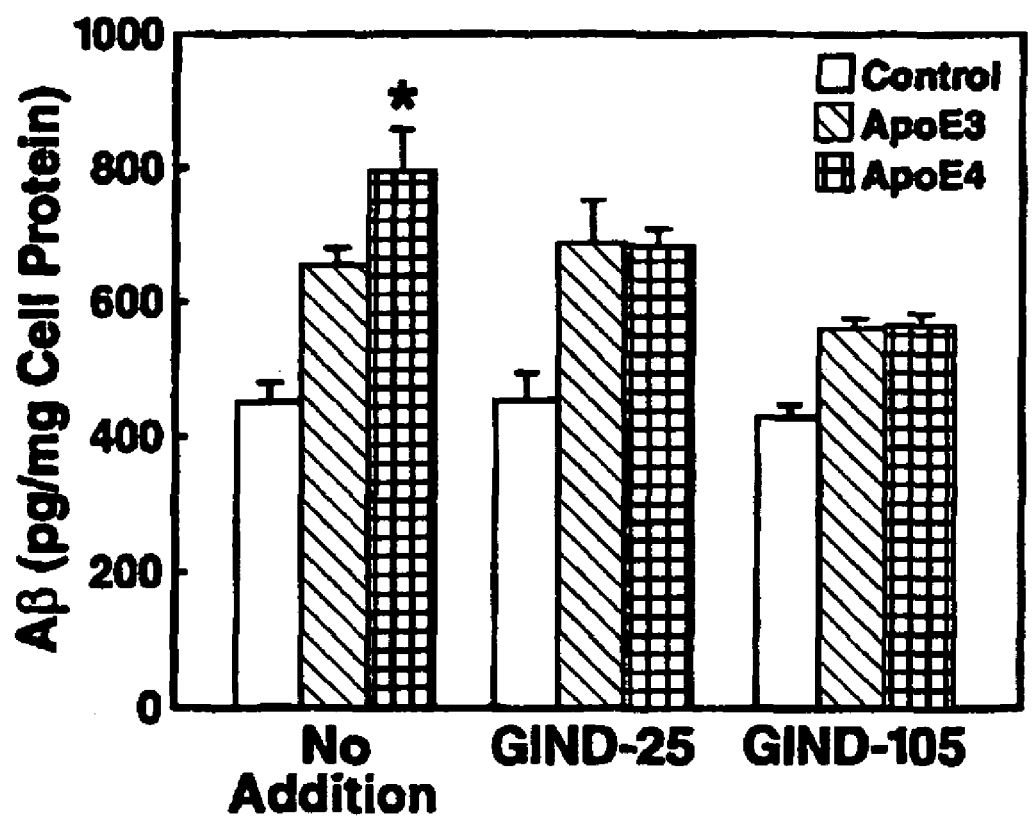
FIG. 22 depicts the effects of compounds on apoE4 enhancement of Aβ production.

The effect of eight of these small molecules (shown in Table 9) on apoE4 enhancement of Aβ production was examined. Four of the eight compounds-azocarmine G, glycine cresol red, 5-chloro-2-(4-chloro-2-(3,4-dichloro phenylureido), and 3-butyl-ethyl-5-(2-(3-sulfobutyl-benzo(1,3)oxazo, also referred to as GIND25, GIND29, GIND32 and GIND105, respectively—abolished completely the apoE4 enhancement of Aβ production, but had no effect on apoE3 (FIG. 22). The four active small molecules are sulfoalkyl compounds that presumably interact with critical basic residues and fit in the groove between helices 2 and 3 of apoE4, thus disrupting domain interaction.

Taken together, as a result of domain interaction, apoE4 increases APP recycling by interacting with cell-surface LRP, leading to increased production of Aβ. The small molecules, or their derivatives, that interact with apoE4 and disrupt domain interaction are useful reagents to decrease apoE4-associated Aβ overproduction.

Example 9

Characterization of Compounds that Inhibit apoE4 Domain Interaction

Materials and Methods

Purified recombinant human apoE3, apoE4, Thr-61 mutant of apoE4 (apoE4-Thr-61), and the receptor-related protein (RAP) were produced as described. Dong and Weisgraber ((1996) *J. Biol. Chem.* 271:19053-19057; Morrow et al. ((2002) *J. Biol. Chem.* 277:50380-50385; and Morrow et al. ((1999) *Protein Expr. Purif.* 16:224-230. Monoclonal antibody (mAb) 6E10 against residues 1-17 of Aβ (detecting sAPPα) and mAb 4G8 against residues 17-24 of Aβ were purchased from Signet (Dedham, Mass.). mAb 266 and mAb 3D6, which recognize residues of 1-5 and 13-28 of Aβ, respectively, were from Elan Pharmaceuticals (South San Francisco, Calif.). mAb 1G7, which recognizes the extracellular domain of APP (residues 380-665), was kindly provided by Dr. Edward H. Koo (University of California at San Diego, La Jolla, Calif.). Lovastatin was from Merck Sharp and Dohlne (Rahway, N.J.). GIND-25 (azocarmine-G), mevalonate, and methyl-β-cyclodextrin were from Sigma (St. Louis, Mo.). GIND-105 (3-butyl-1-ethyl-5-[2-(3-sulfobutyl-benzo[1,3]oxazolin-2-ylidene)-ethylidene]-2-thioxo-imidazolidin-4-one potassium salt was from Synthon (Wolfen, Germany).

Preparation of Lipoproteins. Rabbit β-migrating very low density lipoproteins (β-VLDL) were prepared from rabbits fed a high-cholesterol diet as described. Ji et al. ((1993) *J. Biol. Chem.* 268:10160-10167. Human apoE-enriched β-VLDL were prepared by incubating apoE isoforms with β-VLDL at 37° C. for 1 h.

Cell Culture. Rat neuroblastoma B103 cells stably expressing human wildtype APP (hAPP695wt) (Xu et al. ((1999) *Proc. Natl. Acad. Sci. USA* 96:7547-7552; Esposito, et al. (2004) *J. Neurochem.* 91:1260-1274) were generated in Dr. Lennart Mucke's laboratory at the Gladstone Institute of Neurological Disease and maintained in Dulbecco's modified Eagle's medium (DMEM) (GIBCO, Grand Island, N.Y.) containing 400 µg/ml G418, 10% fetal bovine serum, and 5% horse serum at 37° C. Twenty-four hours after plating into 48-well plates ($1 \times 10^5$ cells per well), cells were washed twice with serum-free DMEM and cultured for another 24 h in DMEM containing 1% N-2 supplement (GIBCO) to induce differentiation. The cells were treated with either β-VLDL (25 µg/ml cholesterol), recombinant human apoE isoform-enriched β-VLDL (7.5 µg/ml apoE and 25 µg/ml cholesterol), or recombinant human apoE (7.5 µg/ml apoE) in fresh DMEM containing 1% N-2 supplement for an additional 24 h. In some experiments, RAP (25 nM or 1 µM) was added to the cells 1 h before apoE treatment.

In some experiments, cells were treated with lovastatin, as described but with a minor modification. Fassbender et al. (2001) *Proc. Natl. Acad. Sci. USA* 98:5856-5861. Briefly, cells were maintained in differentiation medium containing 4 µM lovastatin and 0.25 mM mevalonate for 24 h. After treatment for 5 min with 5 mM methyl-β-cyclodextrin, which depletes cell membrane cholesterol (Bodovitz and Klein (1996) *J. Biol. Chem.* 271:4436-4440; Kojro et al. (2001) *Proc. Natl. Acad. Sci. USA* 98:5815-5820), the cells were incubated in fresh differentiation medium containing lovastatin and mevalonate for 24 h. The conditioned medium was collected, and cellular cholesterol extracted with chloroform/methanol (Huang et al. (1994) *Proc. Natl. Acad. Sci. USA* 91:1834-1838) and quantitated with a kit from Abbott Laboratories (Abbott Park, Ill.).

Detection of sAPPα. Media conditioned for 24 hours were normalized by protein content and subjected to SDS/PAGE. Proteins were then transferred onto nitrocellulose membranes. The sAPPα was detected by mAb 6E10 and visualized with an enhanced chemiluminescence system (Pierce, Rockford, Ill.).

Aβ Assay. Aβ secreted into the medium was detected with a sandwich enzyme-linked immunosorbent assay (ELISA), using mAb 266 as a capturing antibody and 3D6 as a detecting antibody, as described. Johnson-Wood et al. ((1997) *Proc. Natl. Acad. Sci. USA* 94:1550-1555). Aβ was quantified from a standard curve ($A\beta_{42}$; Bachem, Torrance, Calif.) and normalized by total cellular protein.

Cell Association and Degradation of $^{125}I$-$A\beta_{40}$ by Neo-transfected B103 Cells. B103 cells stably transfected with a neomycin-resistance gene (B103-neo) were incubated with a $^{125}I$-labeled 40-amino acid form of A, ($^{125}I$-$A\beta_{40}$) (225 pg/ml, 0.1 µCi/ml) at 37° C. in the presence of apoE3 or apoE4 (7.5 µg/ml). Culture medium was collected after 24 h, and the degradation products of $^{125}I$-$A\beta_{40}$ in the medium were assayed as described. Goldstein et al ((1983) *Methods Enzymol.* 98:241-250). The cells were washed five times on ice with phosphate-buffered saline (PBS) containing 0.2% bovine serum albumin and once with PBS and lysed by 0.1 N NaOH. The cell-associated $^{125}I$-$A\beta_{40}$ was determined by counting the radioactivity in the cell lysate.

Assay for β-secretase Activity. The activity of β-secretase in lysates of cells treated with or without apoE isoforms was assayed, as described (Dong et al. (1994) *J. Biol. Chem.* 269:22358-22365), using a fluorogenic substrate (10 µM, MCA-Glu-Val-Lys-Met-Asp-Ala-Glu-Phe-Lys-DNP-NH₂; SEQ ID NO: 1) (Calbiochem, La Jolla, Calif.). Fluorescence was recorded on a spectrofluorimeter for 10 min with excitation and emission wavelengths of 325 nm and 393 nm, respectively. β-Secretase activity was calculated as the increase in fluorescence per min/mg of cellular protein.

APP Internalization Assay. The internalization of cell-surface APP was measured as described (Koo and Squazzo (1994) *J. Biol. Chem.* 269:17386-17389; Perez et al (1999) *J. Biol. Chem.* 274:18851-18856). Briefly, mAb 1G7, which recognizes the amino-terminal domain of APP, was radioiodinated with IODO-GEN according to the manufacturer's instructions. B103-APP cells or B103-neo cells (background control) grown in six-well plates were treated with apoE3 or apoE4 (7.5 µg/ml) for 24 h, washed with binding buffer (DMEM containing 0.2% bovine serum albumin and 20 mM HEPES), and incubated with radiolabeled 1G7 antibody (2-5 µCi/µg) in the presence of apoE in the same buffer for 30 min at 37° C. Unbound antibody was removed by washing five times with ice-cold PBS. Antibody bound to cell-surface APP was detached by two 5-min washes with ice-cold PBS (pH 2.0). The radioactive cell-surface bound APP antibody was quantitated by counting the low pH-wash buffer, and this represented cell-surface APP. Cells were then lysed with 0.2 N NaOH, and the radioactivity in the cell lysate, representing internalized APP, was determined. Therefore, the ratio of the radioactivity in cell lysate to that in the low pH-wash buffer represents a measure of internalized versus cell-surface APP.

Search for Compounds Capable of Disrupting ApoE4 Domain Interaction. The Available Chemicals Directory of over 200,000 compounds (Molecular Design Limited, Inc., San Leandro, Calif.) was screened computationally using the x-ray structures of the amino-terminal domain of human apoE4 and apoE3 (Wilson et al. (1991) *Science* 252:1817-1822; and Dong et al. (1994) *J. Biol. Chem.* 269:22358-22365). The Available Chemicals Directory, with coordinates for over 200,000 compounds, was screened using the program DOCK, version 4.0 (Kuntz (1992) *Science* 257:1078-1082; Ewing and Kuntz (1997) *J. Comput. Chem.* 18:1175-1189). The target site included residues 109, 112, and 61 plus surrounding regions. DOCK modeled the binding of each candidate molecule to the target protein. The space available for binding was described by a set of spheres that collectively fill the site. The centers of the spheres were then treated as possible ligand atom positions, and each molecule was combinatorially placed in the site in hundreds to thousands of positions. Simple scoring functions, one reflecting shape complementarity and another consisting of a Lennard-Jones van der Waals term and a Coulombic electrostatic term, were used to evaluate the positions. Precalculated grids allowed rapid scoring. Meng et al. (1992) *J. Comput. Chem.* 13:505-524. For each molecule, the best position according to each scoring function was saved. At the end of the process, several hundred best-scoring molecules according to each function were examined graphically.

Over 2000 molecules that scored well when docked to apoE4 were obtained from the DOCK search. In most cases, molecules that also appeared on the corresponding lists for apoE3 were removed from consideration. Compounds were further screened visually using the graphics program MIDAS (Ferrin et al. (1988) *J. Mol. Graph.* 6:13-27) for electrostatic and shape complementarity with the target site. Lipinski et al. (1997) *Adv. Drug Deliv. Rev.* 23:3-25. This process led to a list of 115 compounds, with 65 initial recommendations (one per set of close analogs).

Preparation of Emulsion Particles and VLDL Binding Affinity Assay. VLDL-like emulsion particles were prepared using triolein (160 mg) and L-alpha-phosphatidylcholine (40 mg), as described. Dong and Weisgraber (1996) supra; and Dong et al. (1994) *J. Biol. Chem.* 269:22358-22365. The binding affinity of $^{125}I$-labeled apoE3 and apoE4 to the emulsion particles was determined, as described (Dong and Weisgraber (1996) supra; and Dong et al. (1994) supra), in the presence or absence of various amounts of small molecule compounds. Binding of apoE3 and apoE4 to emulsion particles without compounds was used as a control.

siRNA Preparation and Transfection. Double stranded siRNAs specific for the rat LRP gene were chemically synthesized by Dharmacon (Lafayette, Colo.) according to the following sequences: siLRP6600 sense, 5'-UGGCAUCUCAGUAGACUAUUU-3' (SEQ ID NO:2), antisense 5'-AUAGUCUACUGAGAUGCCAUU-3' (SEQ ID NO:3); siLRP12348 sense, 5'-UGUGUACUGGACCGAUU-CAUU-3' (SEQ ID NO:4), antisense 5'-UGAAUCGGUC-CAGUACACAUU-3' (SEQ ID NO:5). B103-APP cells grown in 48-well plates ($1.0 \times 10^5$ cells/well) for 24 h were transfected with both siRNAs (2 µg/ml for each) using Lipofectamine (Invitrogen) according to the manufacturer's instructions. The transfection complex was diluted in a final volume of 250 µl of Opti-MEM, and was replaced 3 h later with DMEM supplemented with 10% FBS and 5% horse serum. Seventy-two h post transfection, cells were treated with apoE3 or apoE4 and Aβ production was assayed 24 h later, as described above.

Statistical analysis. Results are reported as mean±SD. Differences were evaluated by t test or analysis of variance.

Results

Effects of Cellular Cholesterol on APP Processing and Aβ Production

Figure 23:
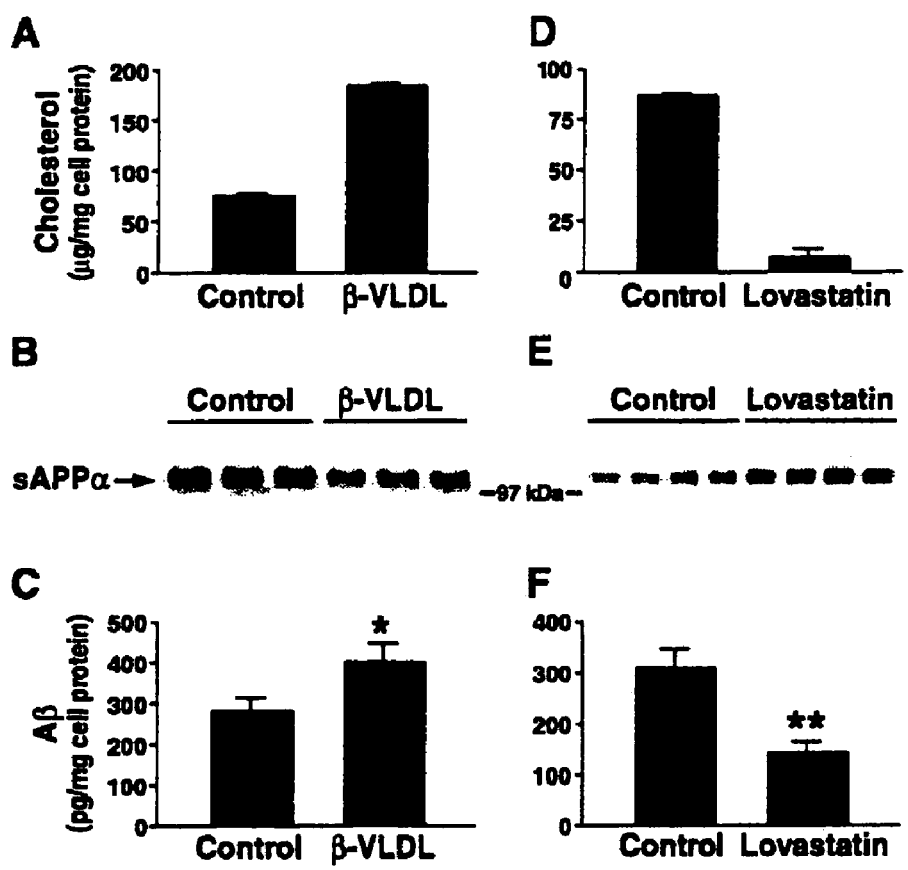
FIGS. 23A-F depict the effects of cellular cholesterol content and apoE isoforms on the secretion of sAPPα and Aβ.

Rat neuroblastoma B103 cells stably transfected with human APP and expressing APP at levels similar to those in mouse brains (Esposito et al. (2004) *J. Neurochem.* 91:1260-1274) were incubated with cholesterol-rich β-VLDL. There was an increase in cholesterol content of the cells (FIG. 23A), a decrease in the secretion of sAPPα (FIG. 23B), and an increase in the production of Aβ (FIG. 23C). In contrast, when cellular cholesterol was lowered with lovastatin (FIG. 23D), sAPPα secretion increased (FIG. 23E) and Aβ production decreased (FIG. 23F). These data are consistent with the concept that cellular cholesterol content can modulate Aβ production and that increased cellular cholesterol levels decrease α-secretase activity and therefore increase Aβ production.

FIGS. 23A-23F. Effects of cellular cholesterol content and apoE isoforms on the secretion of sAPPα and Aβ. B103-APP cells were treated with β-VLDL (25 μg/ml cholesterol), lovastatin (4 μM) or medium alone (control), as described. Cellular cholesterol content was determined after treatment with β-VLDL (A) or lovastatin (D) treatment. sAPPα levels in 24-h-conditioned medium were determined using mAB 6E10 (1 μg/ml) after treatment with β-VLDL (B) or lovastatin (E). (C and F) Aβ in 24-h-conditioned medium were detected by ELISA after treatment with β-VLDL (C) or lovastatin (F). Mean±S.D. of two experiments, each repeated 4-6 times. *, $P<0.05$ vs. control; **, $P<0.01$ vs. control.

Differential Effects of Human ApoE Isoforms on APP Processing and Aβ Production

Figure 24:
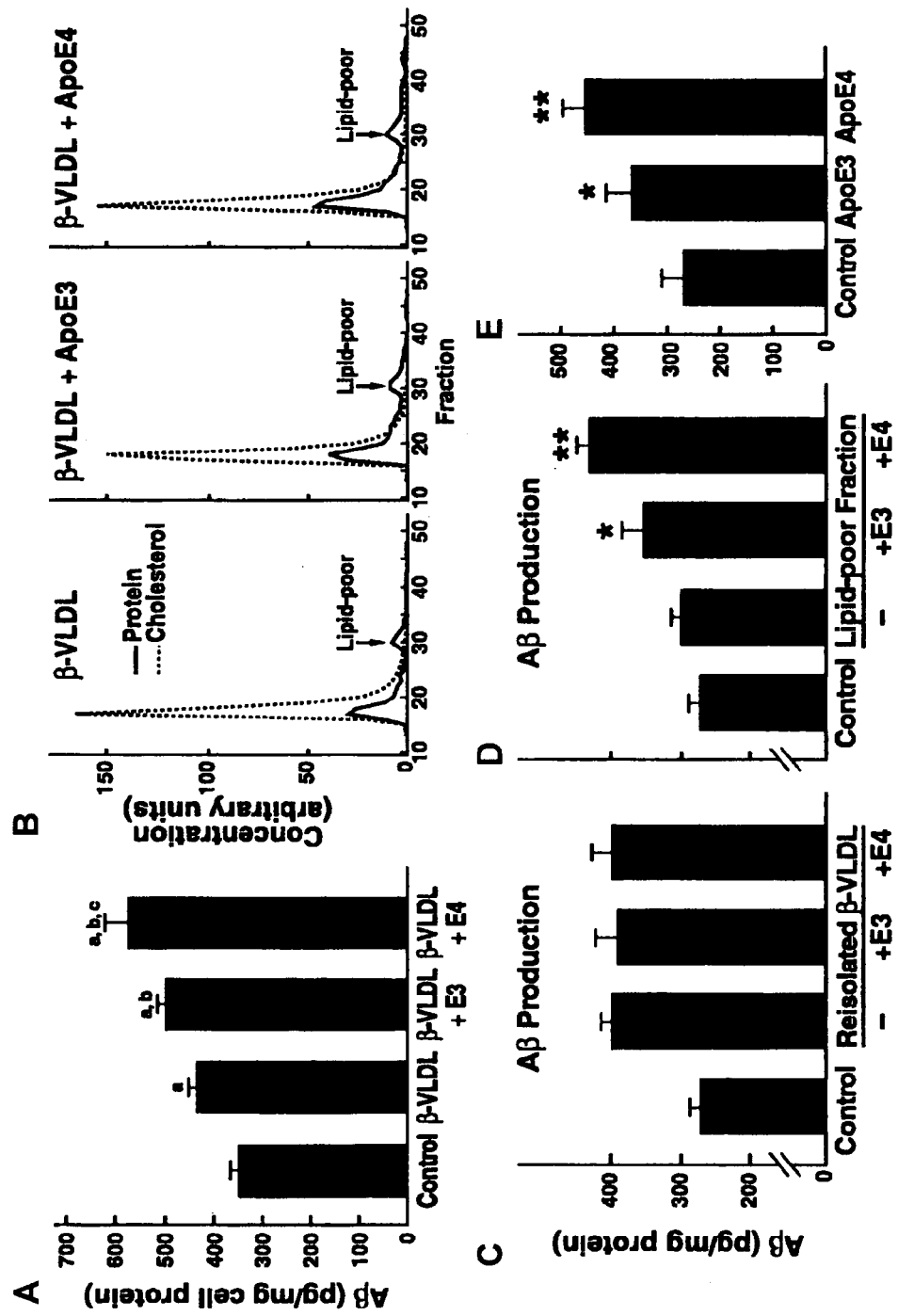
FIGS. 24A-D depict the effect of lipid-poor apoE fractions or free apoE on Aβ production.

Incubation of cultured B103-APP cells with rabbit β-VLDL enriched with human apoE3- or apoE4 stimulated Aβ production compared with cells incubated without lipoproteins or with β-VLDL alone (FIG. 24A). However, when β-VLDL enriched with human apoE was fractionated by fast-performance liquid chromatography into two distinct fractions (a major fraction of apoE-containing β-VLDL and a smaller fraction of lipid-poor apoE) (FIG. 24B), the reisolated β-VLDL enriched with either apoE3 or apoE4 stimulated Aβ production to the same extent (FIG. 2C). In addition, the apoE-containing β-VLDL gave results identical to those of reisolated β-VLDL that were not incubated with human apoE (FIG. 24C). Interestingly, there was no difference in the cholesterol content of any of the treated cells. These results suggest that β-VLDL and β-VLDL containing apoE3 or apoE4 increased cellular cholesterol content and Aβ production to a similar extent and that there was no differential effect of apoE3 or apoE4 under these conditions.

On the other hand, the lipid-poor apoE fraction (FIG. 24B) increased Aβ production in an isoform-specific manner, with apoE4 being more active than apoE3 (FIG. 24D). This isoform-specific effect was further confirmed by treating the cells with lipid-free apoE. Lipid-free apoE3 increased Aβ production by ~30%, whereas lipid-free apoE4 increased Aβ production by ~60% (FIG. 24E) compared to medium alone. Since the cellular cholesterol content was not changed by lipid-free apoE, these data suggest that the isoform-specific effects of apoE on Aβ production are not mediated by changing the cellular content of cholesterol. In other words, apoE and cholesterol may regulate Aβ production by different mechanisms.

FIGS. 24A-D. Lipid-poor apoE fractions or free apoE increase Aβ production in an isoform-specific manner. (A) ApoE3- or apoE4-enriched β-VLDL were prepared by incubating apoE isoforms with β-VLDL at 37° C. for 1 h. Cells were then treated with either medium alone (control), β-VLDL (25 μg/ml cholesterol), or apoE-enriched β-VLDL (7.5 μg/ml apoE and 25 μg/ml cholesterol). Conditioned media were collected after 24 h and assayed for Aβ by ELISA. Values are the mean±S.D. of two experiments, each repeated four times for each condition. a, $P<0.05$ vs. control; b, $P<0.05$ vs. β-VLDL; c, $P<0.05$ vs. β-VLDL+apoE3. (B) ApoE isoforms were incubated with β-VLDL at 37° C. for 1 h. The apoE3- or apoE4-enriched β-VLDL and β-VLDL alone were then fractionated by fast-performance liquid chromatography as described. The elution profiles, which were monitored by quantitation of cholesterol and protein, showed two distinct fractions: a major β-VLDL or apoE-containing β-VLDL fraction and a smaller, lipid-poor apoE-containing fraction. (C and D) Samples from the major β-VLDL or apoE-containing β-VLDL fractions (C) were normalized by cholesterol content and incubated with B103-APP cells at 25 μg/ml cholesterol. Samples from the smaller, lipid-poor apoE-containing fractions (D) were normalized by protein content and incubated with the cells at 7.5 μg/ml of protein. The 24-h-conditioned media were assayed for Aβ by ELISA. Values are the mean±S.D. of two experiments, each repeated 4-6 times for each condition. *, $P<0.05$ vs. control (medium only); **, $P<0.05$ vs. lipid-poor fraction of apoE3 or free apoE3. (E) Recombinant human apoE3 or apoE4 (7.5 μg/ml) was incubated with B103-APP cells for 24 h. The conditioned media were assayed for Aβ by ELISA. Values are the mean±S.D. of three experiments, each repeated 4-6 times for each condition. *, $P<0.05$ vs. control (medium only); **, $P<0.05$ vs. apoE3.

To explore the possible mechanisms responsible for the isoform-specific effects of apoE on Aβ production, it was determined whether the apoE isoforms interact with Aβ and prevent its degradation differentially, thereby retaining different amounts of Aβ in the medium. $^{125}$I-labeled Aβ (350 pg/ml) was incubated with B103-neo cells with or without apoE3 or apoE4. The cell association and degradation of Aβ were not significantly different after incubation for 24 h (Table 10).

TABLE 10

| Cell association and degradation of $^{125}$I-Aβ$_{1-40}$ | | |
|---|---|---|
| | Cell association (fmol/mg cell protein) | Degradation (fmol/mg cell protein) |
| Control | 11.2 ± 1.3 | 73.5 ± 16.4 |
| ApoE3 | 10.8 ± 2.5 | 88.0 ± 6.7 |
| ApoE4 | 14.7 ± 2.5 | 80.8 ± 22.9 |

$^{125}$I-Aβ$_{1-40}$ (350 pg/ml) was incubated with B103-neo cells with or without apoE3 or apoE4. The cell association and degradation of Aβ were measured after a 24-h incubation, as described in *Methods, above*.

Furthermore, apoE3 and E4 had no significant effect on sAPPα secretion or α-secretase activity. Similarly, apoE3 and apoE4 did not significantly affect β-secretase enzyme activity in whole-cell lysates.

Differential Effects of ApoE3 and ApoE4 on APP Recycling

Since the majority of secreted Aβ is generated within the endosomal pathway when mature APP recycles back from the cell surface to endosomes, it is possible that apoE3 and apoE4 stimulate Aβ production by differentially affecting APP recycling. In support of this hypothesis, inhibition of endocytosis by growing cells at 22° C. completely abolished the isoform-specific effects of apoE on Aβ production (FIG. 25A).

To assess further the effects of apoE on APP recycling, the internalization assay established by Koo and associates was performed. Koo and Squazzo (1994) supra; Perez et al. (1999) *J. Biol. Chem.* 274:18851-18856. ApoE increased the internalization (or recycling) of APP in an isoform-specific manner, with apoE4 being more effective than E3 (FIG. 25B). The increased rate of APP internalization (or recycling) by apoE4 may deliver more APP for β-secretase cleavage and therefore generate more Aβ.

Figure 25:
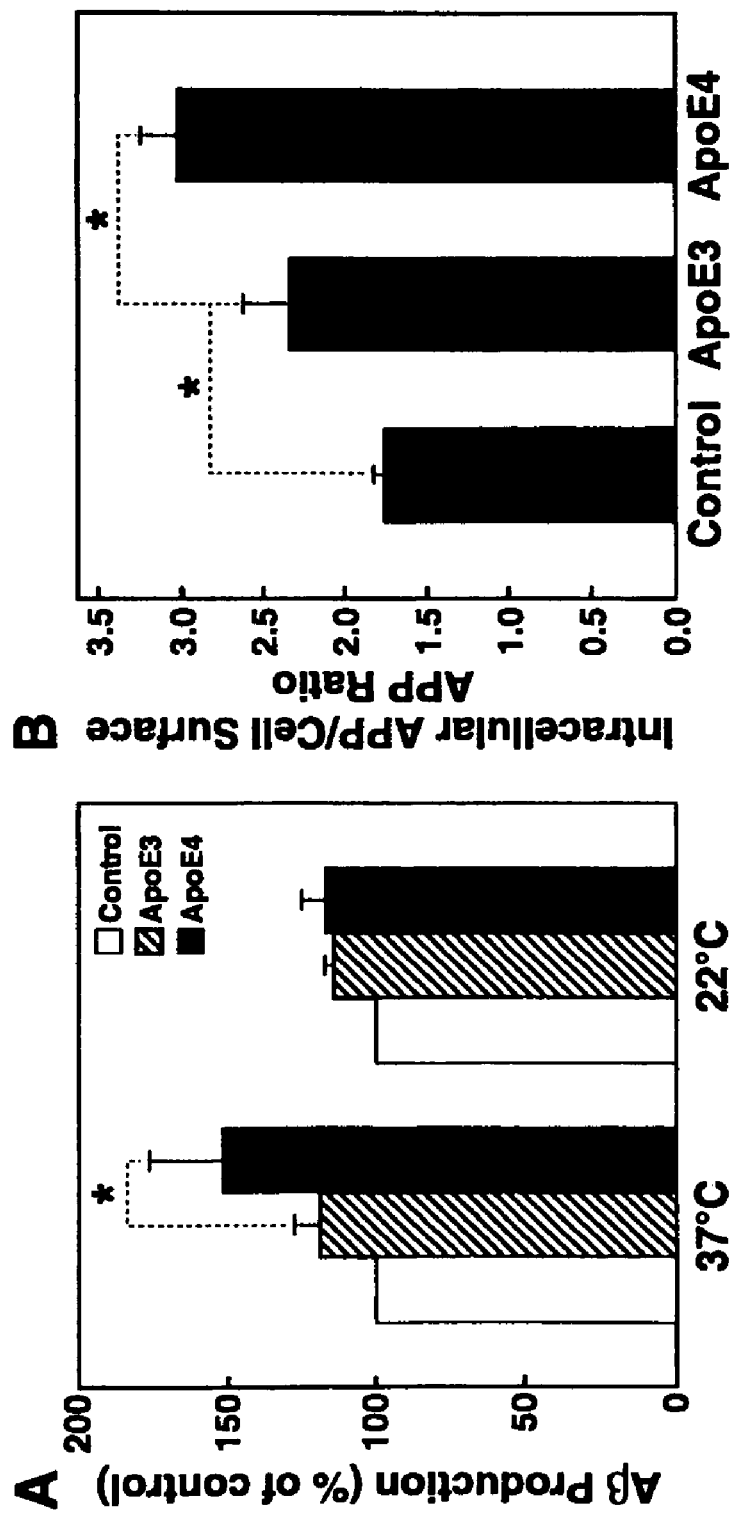
FIGS. 25A and 25B depict the effect of ApoE3 and apoE4 on Aβ production.

FIGS. 25A and 25B. ApoE3 and apoE4 exert isoform-specific effects on Aβ production through their differential effects on intracellular APP recycling. (A) Blockage of APP recycling by culturing cells at low temperature abolished the apoE4-enhanced Aβ production. Recombinant human apoE3 or apoE4 (7.5 μg/ml) was incubated with B103-APP cells at either 22° C. or 37° C. for 24 h. The conditioned media were assayed for Aβ by ELISA. Values are the mean±S.D. of two experiments, each repeated 4-6 times for each condition. *, P<0.05. (B) ApoE4 increased the internalization of cell-surface APP to a greater extent than apoE3. Internalization of cell-surface APP after apoE treatment was determined by measuring the uptake of radioiodinated 1G7 antibody, as described in *Methods*. The results are expressed as a ratio of the radioactivity associated with the internalized versus cell-surface pools of APP. Values are the mean±S.D. of two experiments, each repeated three times for each condition. *, P<0.05.

LRP Mediates the ApoE4 Enhancement of Aβ Production.

ApoE is a ligand for many cell surface receptors, including the LDL receptor, the LRP, heparan sulfate proteoglycans the VLDL receptor, and the apoE receptor-2. To determine the receptor responsible for mediating the stimulatory effect of apoE4 on Aβ production, B103-APP cells were preincubated without or with RAP at a low concentration (25 nM), which blocks the LRP pathway, or at a high concentration (1 μM), which blocks both the LRP and the LDL receptor pathway, at 37° C. for 1 h and then apoE3 or apoE4 (7.5 μg/ml) was added and incubation continued for 24 h. The low concentration of RAP (25 nM) abolished the apoE4-induced enhancement of Aβ production (FIG. 26A), suggesting that the LRP pathway was involved. Interestingly, a high concentration of RAP (1 μM), which blocks both the LRP and the LDL receptor, and a low concentration of RAP (FIG. 26A) had similar effects, suggesting that the LDL receptor pathway may not be involved in apoE enhancement of Aβ production. Furthermore, knockdown (70-80%) of LRP expression by a specific siRNA abolished apoE4-enhanced Aβ production (FIG. 26B), confirming a critical role of the LRP in this process. Interestingly, knockdown of the LRP also decreased significantly Aβ production in control cells, suggesting involvement of the LRP in baseline production of Aβ.

Figure 26:
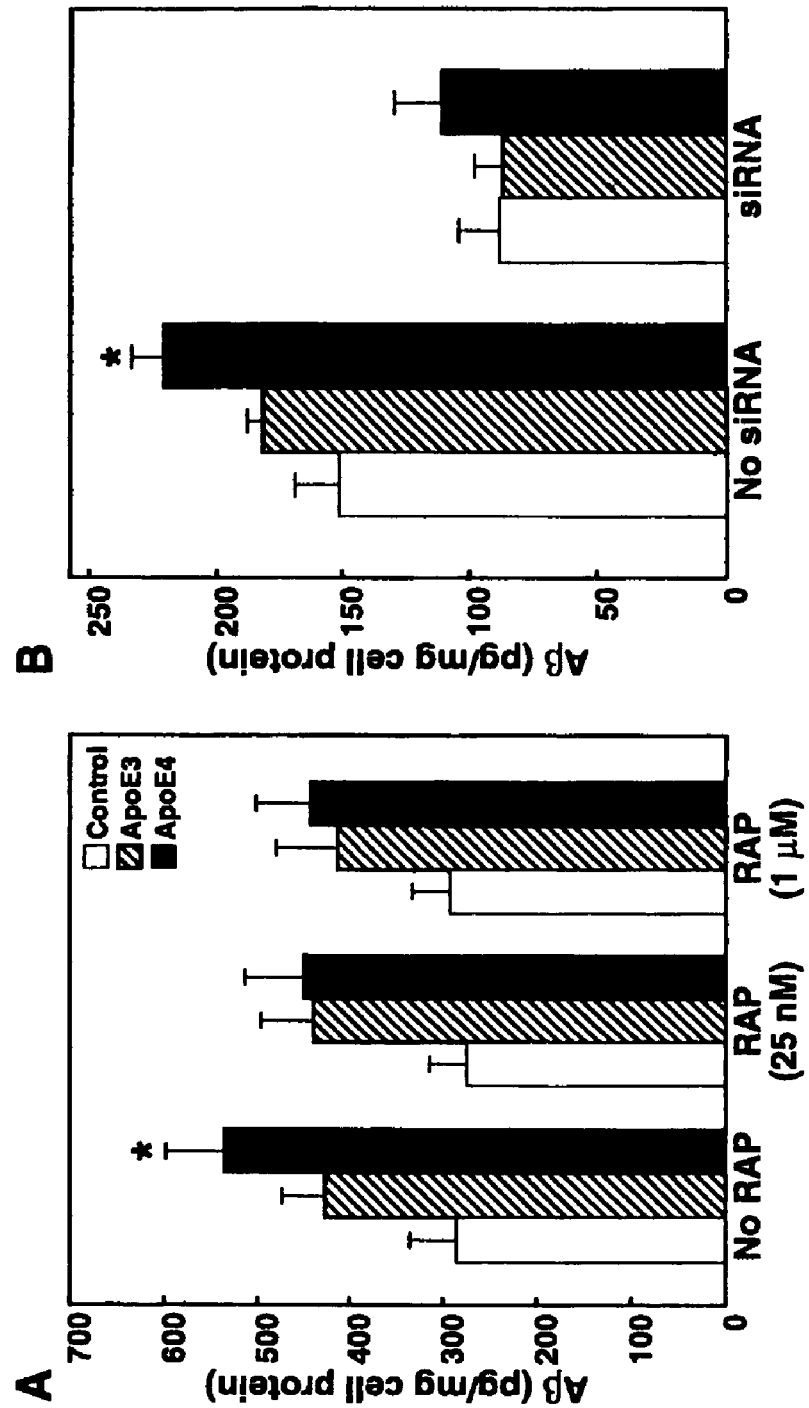
FIGS. 26A and 26B depict LRP mediated enhancement of Aβ production by apoE4.

FIGS. 26A and 26B. The LRP mediates the enhancement of Aβ production by apoE. (A) B103-APP cells were preincubated without or with RAP at a low concentration (25 nM), which blocks the LRP pathway, or a high concentration (1 μM), which blocks both the LRP and the LDL receptor pathway, at 37° C. for 1 h and were then incubated with apoE3 or apoE4 (7.5 μg/ml) for 24 h. The conditioned media were assayed for Aβ by ELISA. *, P<0.05 vs. apoE3. (B) B103-APP cells were treated for three days with siRNA (2 μg nucleotides/well) specific for the rat LRP gene, and were then incubated with apoE3 or apoE4 (7.5 μg/ml) for 24 h. The conditioned media were collected 24 h after apoE treatment and assayed for Aβ by ELISA. Values are the mean±S.D. of percent of control B103 cells without apoE treatment (n=4). *, P<0.05 vs. apoE3.

ApoE4 Domain Interaction Is Responsible for the Enhancement of Aβ Production by ApoE4.

Figure 27:
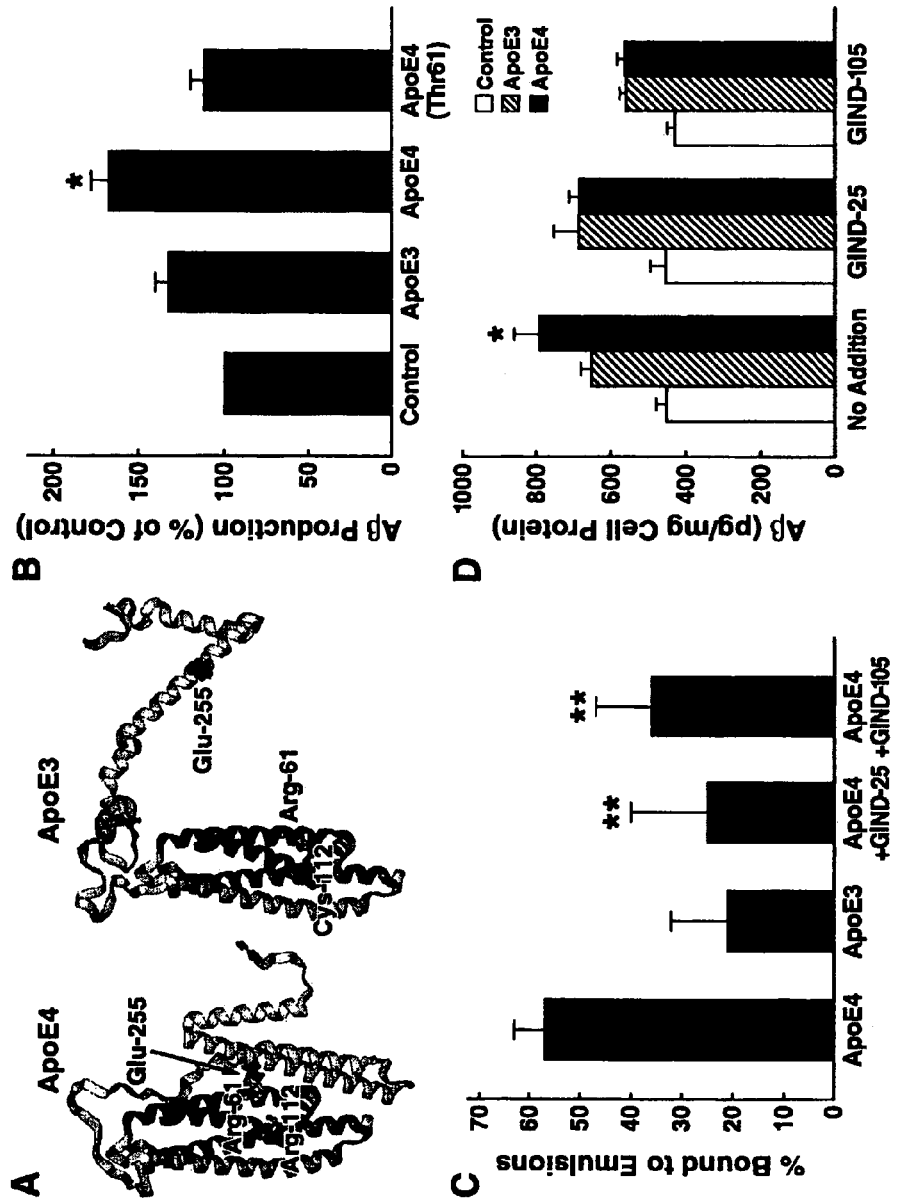
FIGS. 27A-D depict the effect of apoE4 domain interaction on Aβ production by apoE4.

Interaction between the carboxyl- and amino-terminal domains is a unique biophysical property of apoE4, which involves the formation of a salt bridge between Arg-61 and Glu-255 (FIG. 27A). Mutation of either Arg-61 to threonine or Glu-255 to alanine in apoE4 prevents domain interaction and converts apoE4 to a form structurally and functionally resembling apoE3 (FIG. 27A). Therefore, the role of domain interaction in apoE4 stimulation of Aβ production was determined. B 103-APP cells were incubated at 37° C. for 24 h with apoE4-Thr-61 (7.5 μg/ml). Aβ production was determined and compared with that obtained from the B103-APP cells incubated with apoE3 or apoE4 (7.5 μg/ml). Replacement of arginine with threonine at residue 61 abolished the enhanced Aβ production, suggesting that apoE4 domain interaction is involved in stimulating Aβ production (FIG. 27B).

FIGS. 27A and 27B. ApoE4 domain interaction is responsible for the enhancement of Aβ production by apoE4. (A) A model of apoE4 domain interaction as a target for drug development. (B) B103-APP cells were incubated with apoE3, apoE4, or apoE4-Thr-61 (7.5 μg/ml) at 37° C. for 24 h. The conditioned media were collected and assayed for Aβ by ELISA. Values are the mean±S.D. of three experiments, each repeated four times for each condition. *, P<0.05 vs. apoE3 or apoE4-Thr-61. (C) Both GIND-25 (disulfonate) and GIND-105 (monosulfoalkyl) are capable of blocking apoE4 domain interaction as determined by a VLDL-like emulsion binding assay. Values are the mean±S.D. of 5-8 assays. P<0.01 for both compounds vs. apoE4 alone. (D) Compounds GIND-25 and GIND-105 abolish the enhancement of Aβ production by apoE4. Recombinant human apoE3 or apoE4 (7.5 μg/ml) was preincubated with or without GIND-25 or GIND-105.(5 μM) at 37° C. for 30 min and then further incubated with B103-APP cells for 24 h. The conditioned media were collected and assayed for Aβ by ELISA. Values are the mean±S.D. of three experiments, each repeated 3-5 times for each condition.

Small Molecular Compounds Capable of Disrupting Domain Interaction Abolish the Enhancement of Aβ Production by ApoE4.

The preferential binding of apoE4 to VLDL is mediated by domain interaction. Sixty-five small molecule compounds obtained from the DOCK screening were assayed for their abilities to block apoE4 domain interaction using an in vitro VLDL binding assay. Eight out of the 65 compounds were found to inhibit significantly the binding of apoE4 to VLDL-like emulsion particles, suggesting that they disrupt the apoE4 domain interaction. Most of those compounds had little or no effect on apoE3 binding to the emulsion particles. Two compounds (GIND-25, a disulfonate) and GIND-105, a monosulfoalkyl) that inhibited significantly the apoE4 binding (FIG. 27C), but had no significant effect on apoE3 binding, were selected to determine if they could abolish the enhancement of Aβ production resulting from apoE4 domain interaction. Both compounds were water-soluble and had no significant toxicity to B103 cells at the micromole level. As demonstrated in FIG. 27D, both compounds decreased Aβ production induced by apoE4 to levels similar to those induced by apoE3. These results suggest that small molecule compounds capable of disrupting domain interaction can abolish the enhancement of Aβ production by apoE4.

As shown in FIGS. 28A-C, neither apoE3 nor apoE4 changes cellular cholesterol content, sAPPα level, or β-secretase activity. (28A) Cellular cholesterol content was determined after B103-APP cells were treated with recombinant human apoE3 or apoE4 (7.5 βg/ml) for 24 h. Cellular cholesterol was extracted by chloroform and quantitated. (28B) Recombinant human apoE3 or apoE4 (7.5 μg/ml) or β-VLDL (25 μg/ml cholesterol) was incubated with B103-APP cells for 24 h. The conditioned media were normalized by protein content and subjected to SDS/PAGE with 12% gels. Levels of sAPPα were detected with mAb 6E10 (1 μg/ml). (28C) The β-secretase activity was measured after B103-APP cells were treated with recombinant human apoE3 or apoE4 (7.5 μg/ml) for 24 h. Whole-cell extracts were prepared as described in *Methods*. β-secretase activity was measured by incubating 50 μl of cell extract with a fluorogenic substrate (10 μM MCA-Glu-Val-Lys-Met-Asp-Ala-Glu-Phe-Lys-DNP-NH$_2$; SEQ ID NO:1) at 37° C. in reaction buffer (40 mM Tris, pH 7.5, 1 mM CaCl$_2$).

Example 10

FRET Analysis of Inhibition apoE4 Domain Interaction

To establish a cell-based high throughput assay for screening small molecules that disrupt apoE4 domain interaction, a fluorescence resonance energy transfer (FRET) assay was used to analyze living neuronal cells expressing apoE3 or apoE4, as described. Xu et al. (2004) *J. Biol. Chem.* 279: 25511-25516. FRET—the non-radioactive transfer of photon energy from an excited fluorophore (donor) to another fluorophore (acceptor)—occurs only when the donor and acceptor are in close proximity (<100 Å). Thus, this approach can be used to measure nanometer scale distances.

To measure apoE4 domain interaction in living neuronal cells, stably transfected Neuro-2a cells, expressing YFP-apoE3-CFP or YFP-apoE4-CFP at similar levels, were used. Neuro-2a cells were stably transfected with one of two constructs: 1) YFP-apoE3-CFP is a construct comprising, in order from 5' to 3', a yellow fluorescent protein (YFP) coding sequence, a human apoE3 coding sequence, and cyan fluorescent protein (CFP) coding sequence, cloned into a pFLAG-CMV3 vector (Sigma); and 2) YFP-apoE4-CFP is a construct comprising, in order from 5' to 3', a yellow fluorescent protein (YFP) coding sequence, a human apoE4 coding sequence, and cyan fluorescent protein (CFP) coding sequence, cloned into a pFLAG-CMV3 vector. Xu et al. (2004) *J. Biol. Chem.* 279:25511-25516. The constructs are depicted schematically in FIG. 29.

Figure 31:
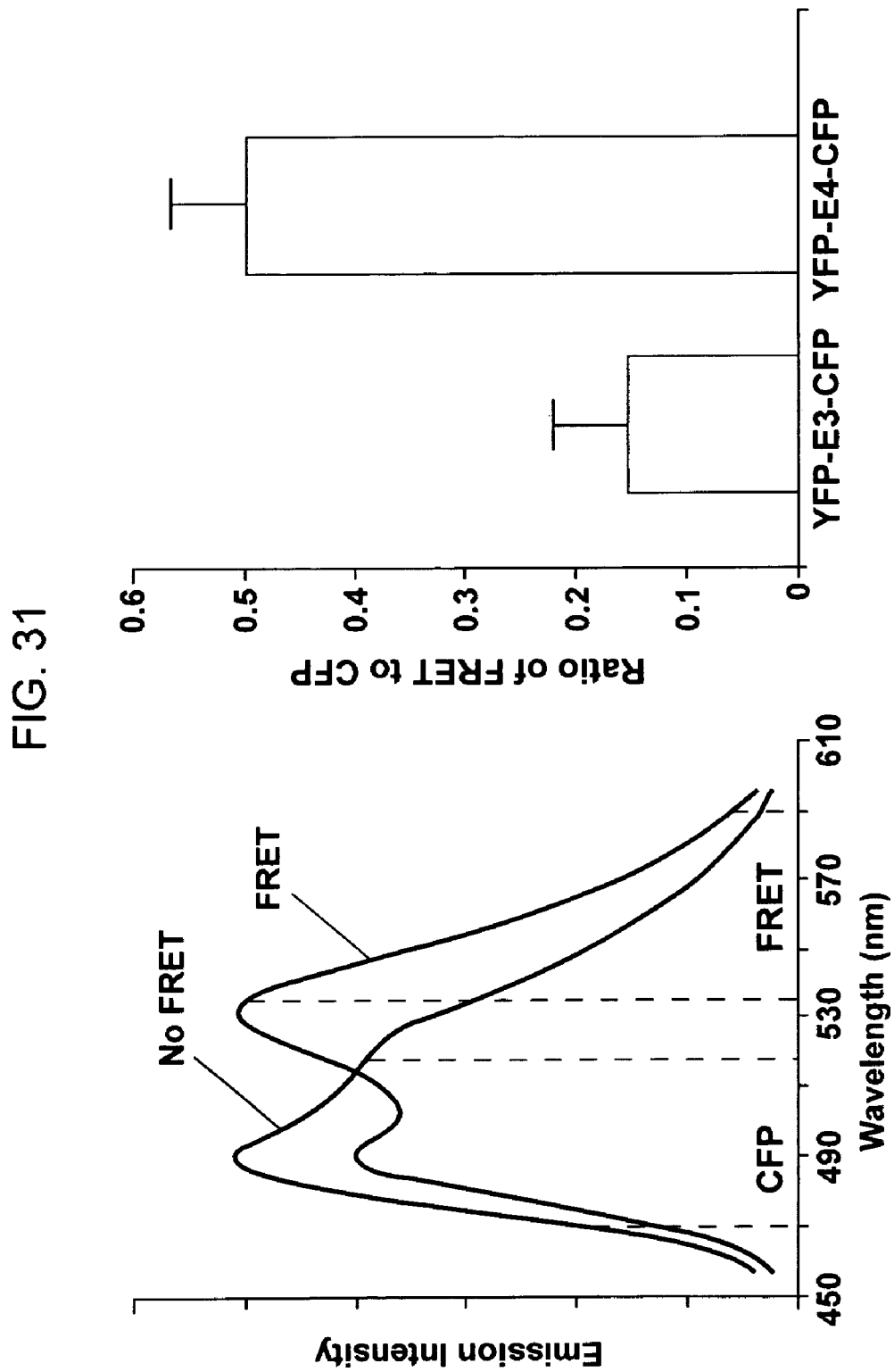
FIG. 31 depicts the ratio of FRET to CFP fluorescence as a measure of domain interaction.

Since the emission spectrum of CFP (460-520 nm) overlaps with the excitation spectrum of YFP (480-520 nm), FLEXstation (Molecular Devices) can be used to measure FRET in living cells expressing YFP-apoE3-CFP or YFP-apoE4-CFP in a high throughput manner. Since CFP and YFP are in close proximity in apoE4, but not in apoE3, due to the domain interaction, part of the emission energy under CFP excitation is transferred from CFP to YFP, thereby increasing YFP emission and decreasing CFP emission (depicted schematically in FIG. 30). Thus, the ratio of FRET to CFP emission in cells expressing YFP-apoE4-CFP is much higher than that in those expressing YFP-apoE3-CFP (FIG. 31). Furthermore, treatment of the cells expressing YFP-apoE4-CFP with small molecules that disrupt apoE4 domain interaction should decrease the ratio of FRET to CFP emission, which can be used as a high throughput screening assay. Since the FLEXstation can read FRET in both cells and the culture media treated without or with various small molecules, this assay allows one to know whether a small molecule affects apoE4 domain interaction only in the medium ("medium FRET") or also inside the cell ("intracellular FRET"). In addition, after measurement of the intracellular FRET, the cells can be incubated further with MTT to determine the cytotoxicity of the compound. Thus, the cell-based FRET assay can simultaneously provide three sets of data-intracellular FRET, medium FRET, and cytotoxicity.

Experimental Procedures

Preparation of cDNA Constructs Encoding ApoE3 or ApoE4 Fused with YFP and CFP—PCR products encoding wildtype human apoE3 or apoE4 without a stop codon were subcloned into a pFLAG-CMV3 vector (Sigma) that contains an amino-terminal FLAG tag and a signal peptide sequence. A PCR product encoding YFP without a stop codon was amplified from the pEYFP-N1 vector (Clontech, Palo Alto, Calif.) and subcloned into the pFLAG-CMV3-apoE3 and pFLAG-CMV3-apoE4 vector at the N-terminus of apoE. Finally, a PCR product encoding CFP with a stop codon was amplified from the pECFP-C1 vector (Clontech) and subcloned into the pFLAG-CMV3-YFP-apoE3 and pFLAG-CMV3-YFP-apoE4 vector at the C-terminus of apoE. cDNA constructs encoding YFP-apoE3-CFP and YFP-apoE4-CFP were generated. All DNA constructs were confirmed by sequence analysis.

Cell Cultures and Transfection—Mouse neuroblastoma Neuro-2a cells (American Type Culture Collection) were maintained at 37° C. in minimum essential medium containing 10% fetal bovine serum. Neuro-2a cells were transfected with the apoE cDNA constructs described above using Lipofectamine 2000 reagent (Invitrogen, Carlsbad, Calif.). Stable cell lines expressing YFP-apoE3-CFP or YFP-apoE4-CFP were selected by continuously incubating them in minimum essential medium containing 10% fetal bovine serum and 400 μg/ml of G418.

Quantifying FRET in Transfected Neuro-2a Cells—Stably transfected Neuro-2a cells expressing YFP-apoE3-CFP or YFP-apoE4-CFP at similar levels were selected by fluorescence activated cell sorter (FACS). YFP and CFP images of transfected cells were acquired with the Meta Detector, and their fluorescence intensities were analyzed with the mounted computer. The FRET signal was calculated as the ratio of YFP to CFP fluorescence intensity under CFP excitation. For each YFP-apoE-CFP construct, the FRET signal was measured in at least 12 cells from different fields.

Quantifying FRET in the Culture Medium—Neuro-2a cells stably expressing YFP-apoE3-CFP or YFP-apoE4-CFP and wildtype cells were grown in T175 flasks to 90% confluence and incubated with serum-free minimum essential medium containing N2 supplement for 24 h. The conditioned medium (20 ml/flask) was concentrated about 20-fold with Centriplus-YM-10 concentrators (Amicon, Bedford, Mass.), dialyzed against PBS, illuminated at the CFP excitation wavelength (430 nm), and scanned for emission spectrum. The FRET signal was calculated as the ratio of emission at 525 nm (YFP) to that at 475 nm (CFP). Conditioned medium from cells expressing apoE3-CFP or apoE4-CFP was used to determine baseline fluorescence in the absence of FRET.

Statistical Analysis-Results are reported as mean±SD. Differences were evaluated by t test or analysis of variance.

Results

Figure 32:
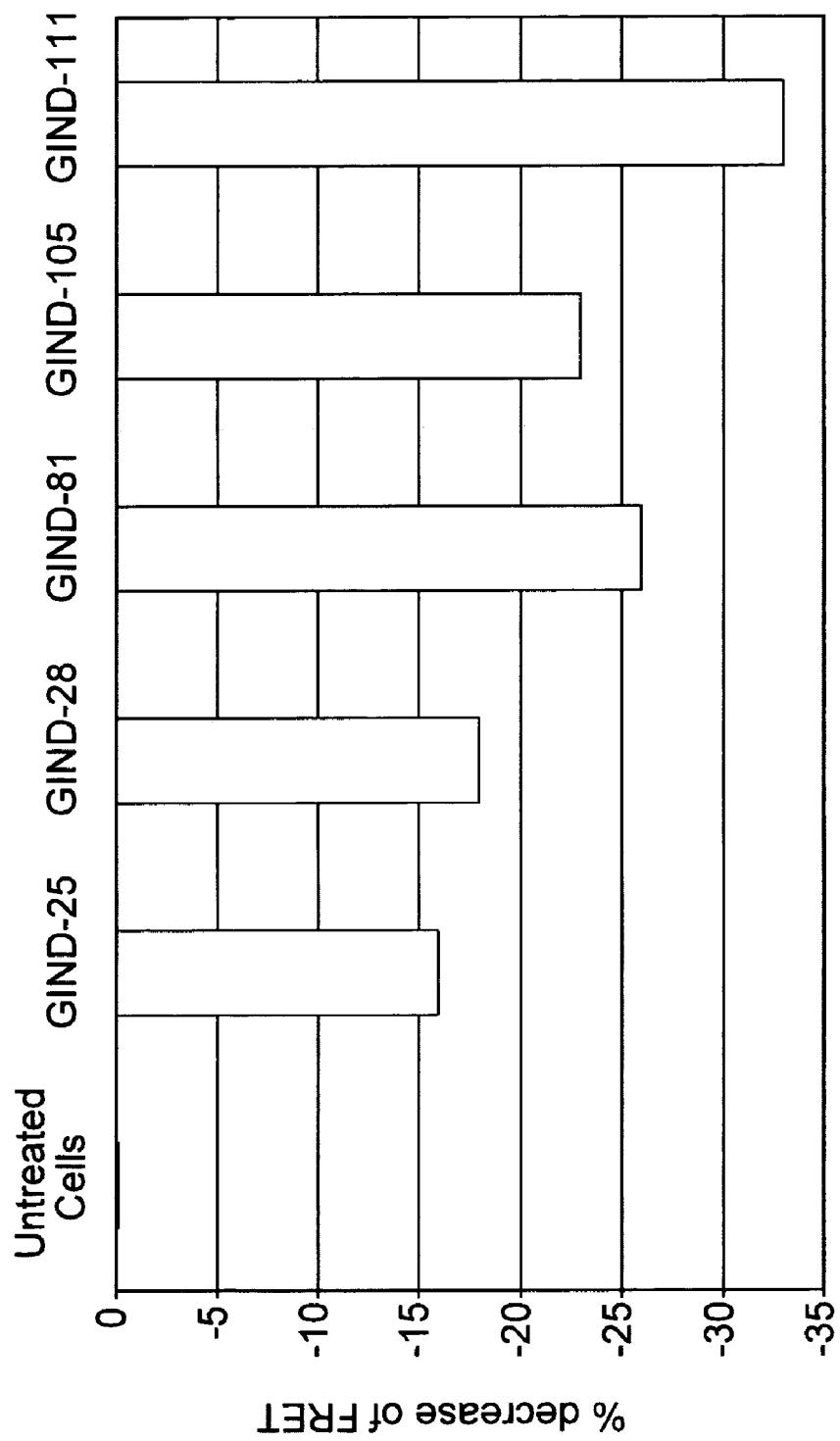
FIG. 32 depicts the effects of various compounds on intracellular-FRET of YFP-apoE4-CFP cells.
Figure 33:
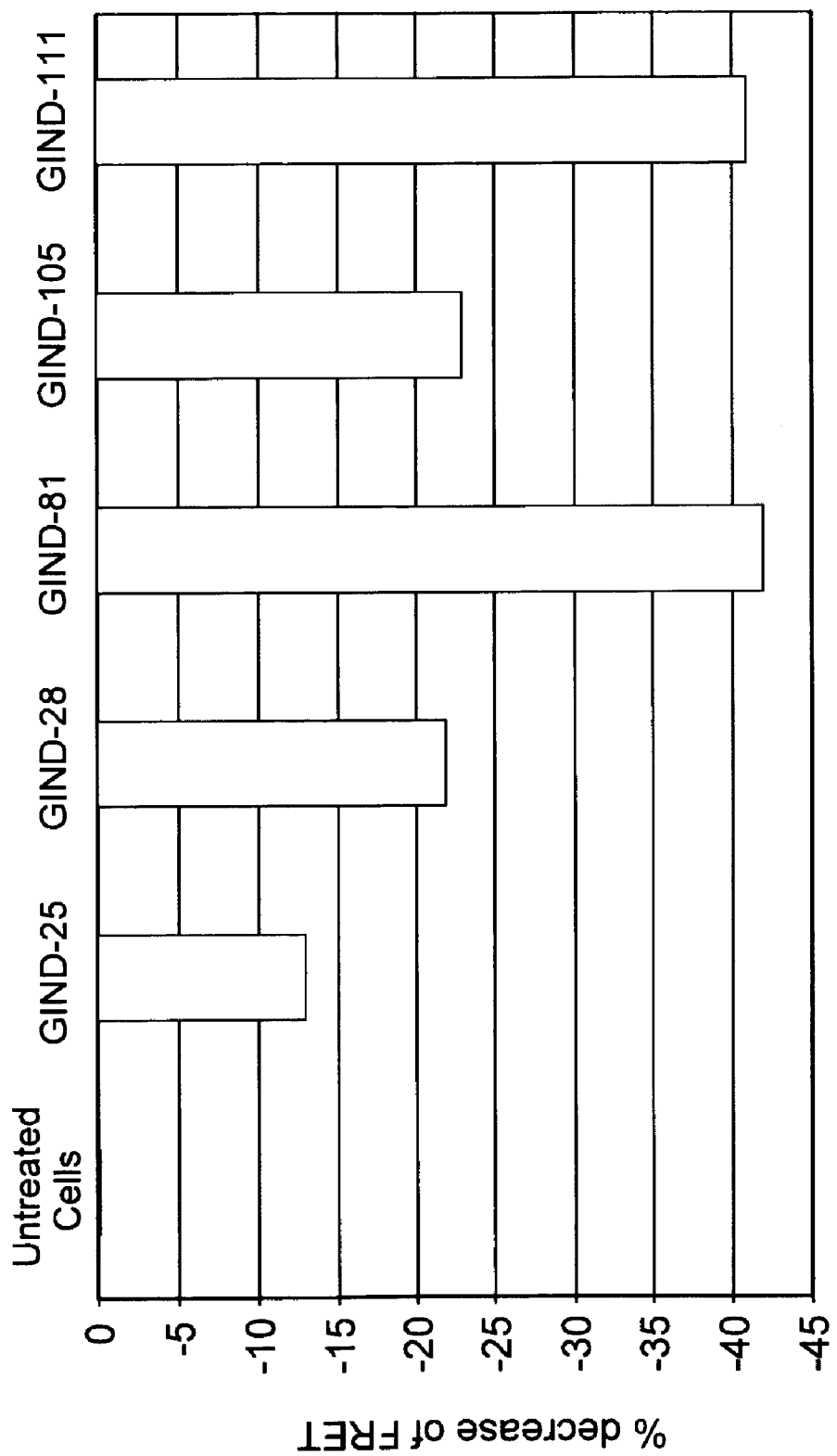
FIG. 33 depicts the effects of various compounds on FRET in medium of YFP-apoE4-CFP cells.
Figure 34:
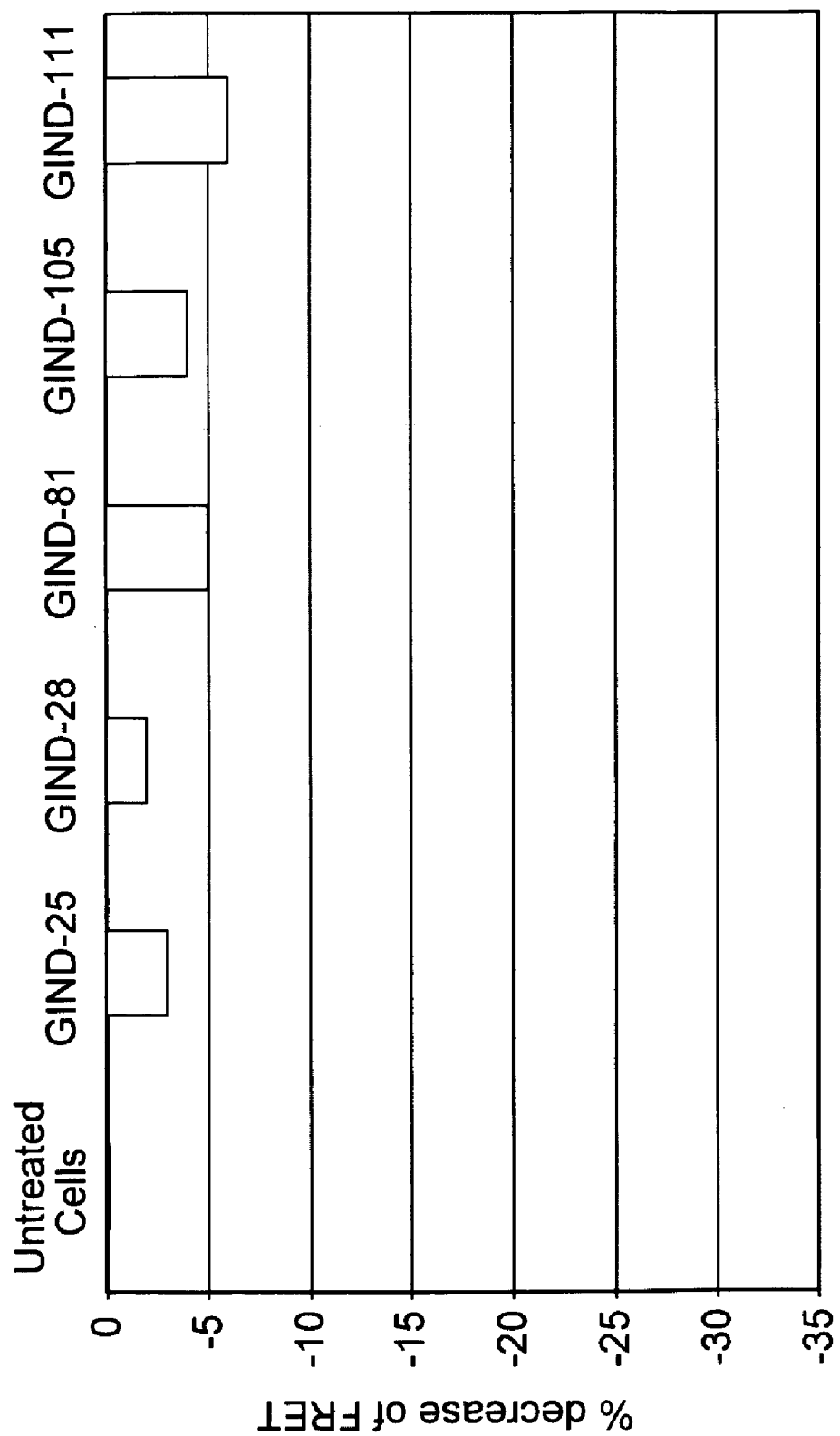
FIG. 34 depicts the effects of various compounds on intracellular FRET of YFP-apoE3-CFP cells.
Figure 35:
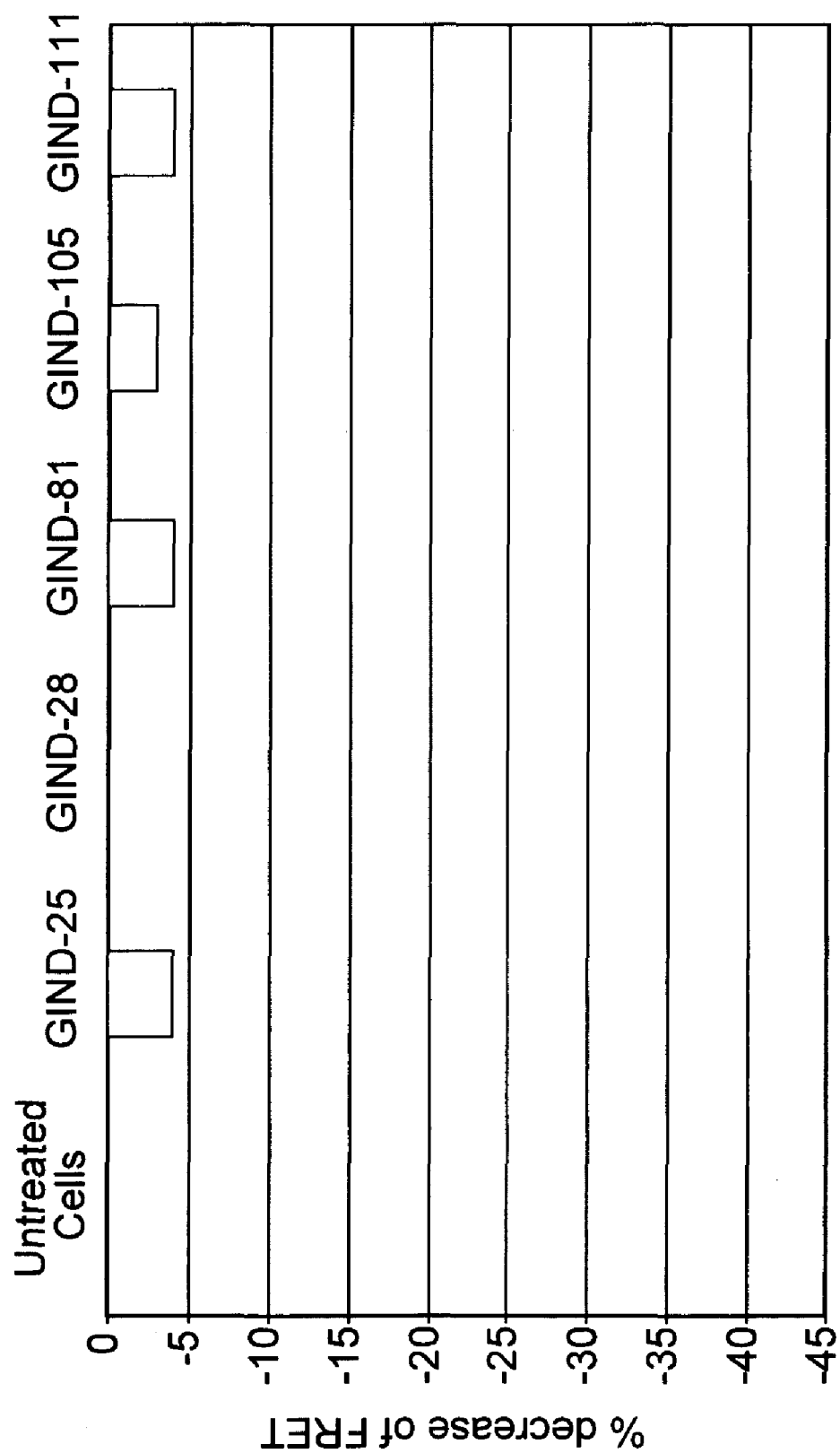
FIG. 35 depicts the effects of various compounds on FRET in medium of YFP-apoE3-CFP cells.
Figure 36:
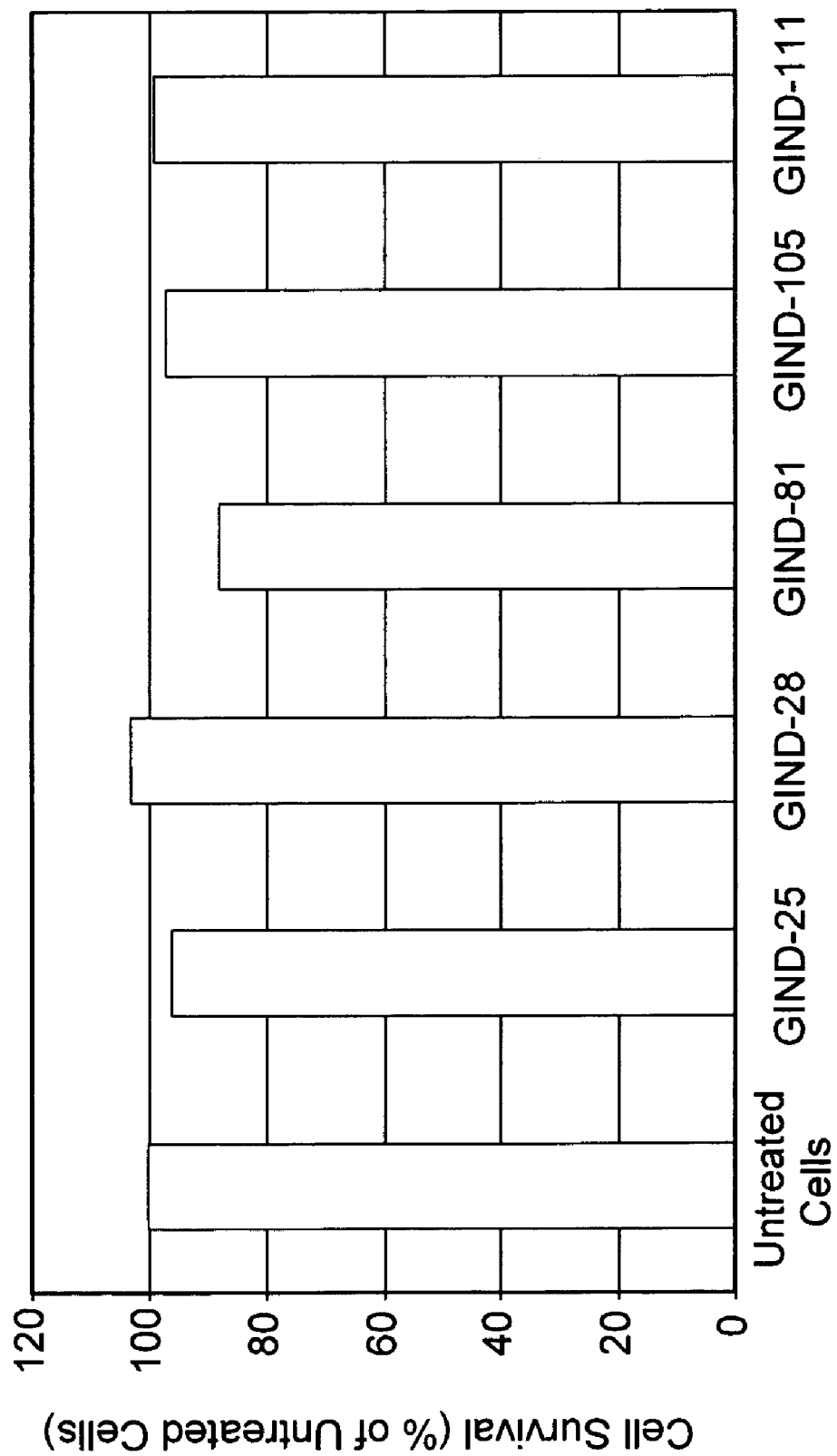
FIG. 36 depicts the effects of various compounds on survival of YFP-apoE4-CF: cells.

Using the cell-based FRET assay, some of the DOCK compounds that could disrupt apoE4 domain interaction were tested in a VLDL binding assay. Compounds GIND-25, GIND-28, GIND-81, GIND-105, and GIND-111, at the dose of 5-20 μM, decreased significantly the ratio of FRET to CFP emission in both the cells expressing YFP-apoE4-CFP (FIG. 32) and their media (FIG. 22), indicating that these compounds disrupt the apoE4 domain interaction. Importantly, none of these compounds altered significantly the ratio of FRET to CFP emission in cells expressing YFP-apoE3-CFP (FIG. 34) and their media (FIG. 35). MTT ([3-(4,5-dimethylthiazol-2-yl)-2,5-diphenyl-2 H-tetrazolium bromide]) assay demonstrated that all these compounds at the dose of 5-10 µM did not cause significant cytotoxicity (FIG. 36).

Example 11

Effect of apoE4 Domain Interaction Inhibitors on Aβ-Induced Lysosomal Leakage and Apoptosis in Neuronal Cells Methods and Materials Cell Culture—Neuro-2a cells were maintained in NB medium (50% Dulbecco's modified Eagle's medium and 50% F12 medium) containing 10% fetal bovine serum. Neuro-2a cells were transfected with apolipoprotein (apo) E3 or apoE4 genomic DNA by the LipofectAMINE method. Stably transfected cells were selected in 10% NB medium containing 400 µg/ml G418. The amount of apoE secreted into the culture medium by transfected cells was measured by immunoblot. ApoE3- and apoE4-transfected cells secreting 40 or 80 ng of apoE/ml of medium/24 h were chosen for the studies; cells secreting 80 ng of apoE/ml of medium/24 h were used unless otherwise noted.

Amyloid $\beta_{1-42}$ ($A\beta_{1-42}$) or $A\beta_{1-40}$ (1 mg) was dissolved in 100 µl of dimethyl sulfoxide and diluted in water to 1 ml. Aβ was incubated at 37° C. for 72 h to form aggregates before use.

DNA Fragmentation Assay—DNA fragmentation of apoptotic cells was determined with Cell Death Detection ELISA kits (Roche, Indianapolis, Ind.).

Measurement of Lysosomal Membrane Stability—Cells were treated with $A\beta_{1-42}$ or apoE as described and membrane stability and leakage of lysosomes were measured in the cytosol by Lucifer Yellow release and β-hexosaminidase activity. The cytosolic fraction was obtained by ultracentrifugation, and the cytosolic β-hexosaminidase activity was measured.

Results

ApoE4 Potentiates Aβ-induced Lysosomal Leakage—To determine if apoE has isoform-specific effects on Aβ-induced lysosomal leakage, neo-, apoE3-, and apoE4-transfected Neuro-2a cells were incubated with 20 µM $A\beta_{1-42}$ (or $A\beta_{1-40}$) for 20 h at 37° C. No significant lysosomal leakage was observed in untreated apoE3- or apoE4-transfected cells. After treatment with $A\beta_{1-42}$, however, it was readily apparent that more apoE4-transfected Neuro-2a cells than neo- or apoE3-transfected cells displayed a diffuse intracellular pattern of fluorescence, indicating lysosomal leakage into the cytosol.

Figure 37:
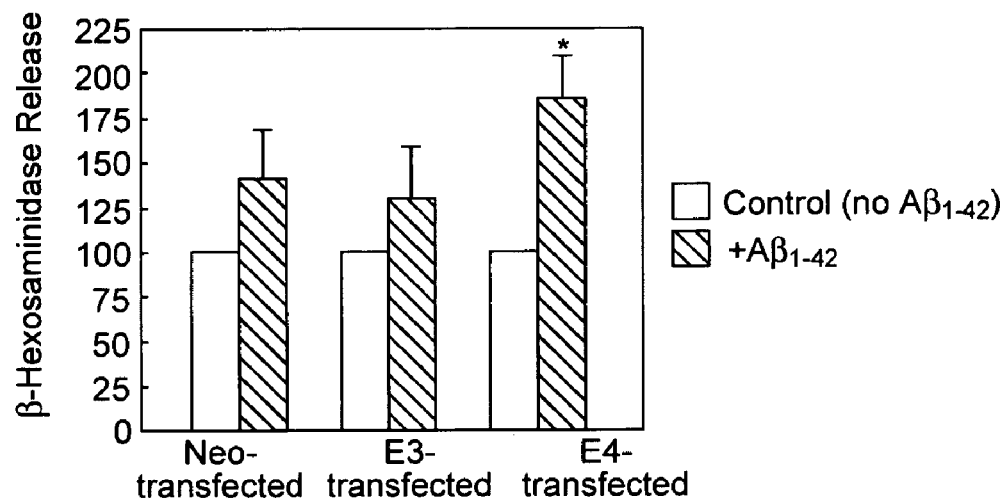
FIG. 37 depicts Aβ-induced lysosomal leakage in apoE3- and apoE4-transfected cells.

The effects of apoE3 and apoE4 on $A\beta_{1-42}$-induced lysosomal leakage were assayed by measuring the lysosomal enzyme β-hexosaminidase in the cytosol (FIG. 37). Aβ treatment increased cytosolic β-hexosaminidase activity to a significantly greater extent in apoE4-transfected cells than in neo- and apoE3-transfected cells (~85% versus ~40% and ~30%, respectively; p<0.001). The differences observed for the neo- versus the apoE3-transfected cells treated with Aβ were not statistically significant.

FIG. 37. Aβ-induced lysosomal leakage in apoE3- and apoE4-transfected cells. Quantitation of the lysosomal enzyme β-hexosaminidase activity in the cytosol indicates lysosomal leakage. The neo-, apoE3-, and apoE4-transfected cells were grown in 100-mm dishes to ~90% confluence and incubated with 20 µM of $A\beta_{1-42}$ for 24 h. After incubation the cells were washed and cytosolic fractions were isolated as described in *Materials and Methods*. The enzymatic activity of β-hexosaminidase was assayed in 20 µg of cytosolic protein for each sample. Values are the mean±S.D. of two separate experiments performed in duplicate. *ApoE4-transfected cells treated with $A\beta_{1-42}$ versus neo- and apoE3-transfected cells treated with $A\beta_{1-42}$ (p<0.001).

Figure 38:
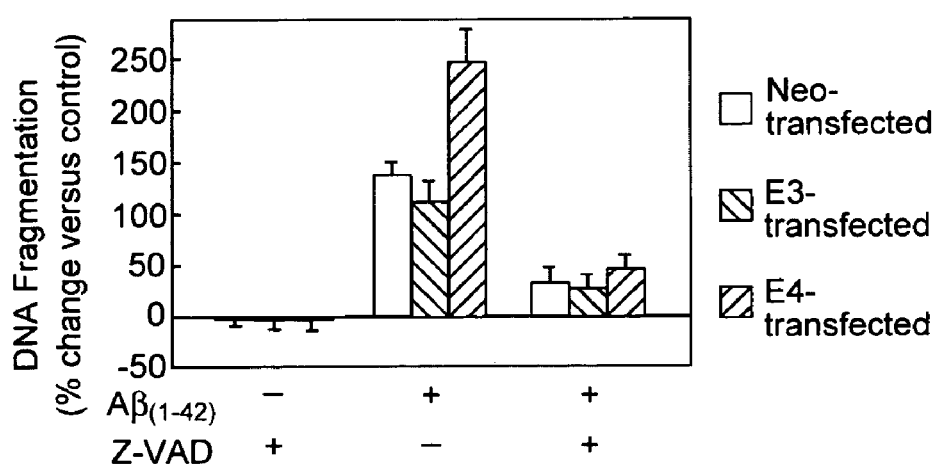
FIG. 38 depicts the effect of apoE4 on apoE3-induced apoptotic DNA fragmentation.

ApoE4 Potentiates $A\beta_{1-42}$-Induced Cell Death and Apoptosis—Transfected Neuro-2a cells were incubated with 20 µM $A\beta_{1-42}$ for 18 h at 37° C. To investigate the differential effects of apoE3 and apoE4 on Aβ-induced apoptosis, we measured DNA fragmentation in neo-, apoE3-, and apoE4-transfected Neuro-2a cells 18 h after the addition of 20 µM $A\beta_{1-42}$. DNA fragmentation was increased to a much greater extent in apoE4- than in neo- and apoE3-transfected cells (~250% versus ~140% and 110%, respectively, of that in Z-VAD-treated control cells) (FIG. 38). There was only a trend toward apoE3 being protective; however, the potentiation of $A\beta_{1-42}$-induced apoptosis by apoE4 was highly significant (p<0.001). Pretreatment with Z-VAD greatly reduced the Aβ-induced DNA fragmentation in all three cell lines and abolished almost all of the potentiation seen in the apoE4-transfected Neuro-2a cells (FIG. 38).

FIG. 38. ApoE4 enhances Aβ-induced apoptotic DNA fragmentation. Neuro-2a cells were incubated first with or without Z-VAD (100 µg/ml) for 2 h and then with $A\beta_{1-42}$ for 18 h. Control cells were not treated with $A\beta_{1-42}$. Apoptotic cell death was measured with a DNA fragmentation assay. Values are the mean±S.D. of three separate experiments. The effects of Z-VAD treatment alone were compared with results obtained in untreated control cells and showed no effect in any of the cell lines.

Conditioned Medium from ApoE3- and ApoE4-secreting Neuro-2a Cells: ApoE4 Potentiates Apoptosis—The possibility that apoE generated within the secretory pathway of the transfected cells might be responsible for the results seen after $A\beta_{1-42}$ treatment was considered. ApoE3- and apoE4-secreting Neuro-2a cells were cultured for 24 h, and the conditioned media were transferred to neo-transfected cells; 20 µM of $A\beta_{1-42}$ was added, and DNA fragmentation quantitated after 18 h. Aβ-induced DNA fragmentation was significantly greater in cells incubated with apoE4-conditioned medium than in those incubated with neo- or apoE3-conditioned medium (314% versus 232% and 202%, respectively; p<0.05). There was a trend toward less DNA fragmentation in cells incubated in apoE3-conditioned medium than in those incubated in neo-conditioned medium (p=0.067).

Small Molecules Identified by DOCK to Inhibit ApoE4 Domain Interaction Block the ApoE4 Potentiation of Aβ-induced Lysosomal Leakage and Apoptosis—As shown in FIGS. 39A and 39B, GIND-25, -28, and -105 block the lysosomal leakage and apoptosis associated with apoE4, but have no significant effect on cells incubated with medium alone or medium containing apoE3 plus $A\beta_{1-42}$.

FIGS. 39A and 39B. (39A) Small molecules (GIND-25, -28, and -105; 5 µM) that inhibit apoE4 domain interaction abolish the apoE4 potentiation of Aβ-induced lysosomal leakage. Neuro-2a cells were incubated with conditioned media collected from C6 astrocytic cells transfected with neo-, apoE3, or apoE4 (37° C. for 24 h). In some cases $A\beta_{1-42}$ (20 µM) was added to the cells. Lysosomal leakage was quantitated by assaying cytosolic 0-hexosaminidase activity. (39B) Small molecules (GIND-25, -28, and -105) that inhibit apoE4 domain interaction abolish the apoE4 potentiation of Aβ-induced apoptosis. Conditioned media were prepared as described above. Apoptosis was quantitated by measuring DNA fragmentation.

Example 12

Domain Interaction Promotes apoE4's Susceptibility to Proteolysis, which Generates Neurotoxic Fragments It has been demonstrated that apoE is subject to cleavage by a chymotrypsin-like serine protease that generates bio active carboxyl-terminal-truncated fragments of apoE [Huang Y. et al., (2001) *Proc. Natl. Acad. Sci. USA*, 98:8838-8843]. Higher levels of these apoE fragments in the brain of AD patients than in age- and sex-matched nondemented controls have been observed. ApoE4 fragmentation was specific for certain brain regions, occurring to a greater extent in the cortex and hippocampus, which are vulnerable to AD-related neurodegeneration, than in the cerebellum, which is not [Brecht W. et al., (2004) *J. Neurosci*, 24:2527-2534]. Furthermore, when expressed in cultured neuronal cells or added exogenously to the cultures, the truncated apoE4 was neurotoxic, leading to cell death and the formation of intracellular NFT-like inclusions in some of the dying cells [Huang Y. et al., (2001) *Proc. Natl. Acad. Sci. USA*, 98:8838-8843].

To determine the pathogenic potential of the apoE4 fragment in vivo, generated transgenic mice were generated that synthesize and secrete, at various levels, apoE4 that lacks the carboxyl-terminal 28 amino acids [apoE4(Δ272-299)] in neurons [Harris F M. et al., (2003) *Proc. Natl. Acad. Sci. USA*, 100:10966-10971]. The truncated apoE4 corresponds to one of the main truncated species generated in AD brains. Hippocampal or cortical neurons in the high-expresser mice had numerous cytoplasmic inclusion bodies containing truncated apoE4, which could be observed in mice as young as 2-4 months. H&E staining revealed degeneration of neurons expressing the truncated apoE4 at these ages. Gallyas silver'staining revealed NFT-like inclusions in neocortical neurons. Behavioral tests demonstrated impairments of learning and memory in 6-7-month-old transgenic mice expressing low levels of the truncated apoE4. However, a shorter truncated form of apoE4 [apoE4(Δ241-299)] lacking the lipid-binding domain (amino acids 244-272) did not induce neuropathology in transgenic mice, suggesting that the lipid-binding domain within the truncated apoE4 fragments may be responsible for the neurotoxic effect [Harris F M. et al., (2003) *Proc. Natl. Acad. Sci. USA*, 100:10966-10971].

To determine whether the fragmentation is isoform-specific, the amounts of apoE fragments (29-kDa and 14-20-kDa together) were measured by anti-apoE western blotting in brain lysates of AD patients (n=19) with or without apoE4 and age- and sex-matched controls (n=17) with corresponding apoE genotypes. The ratios of the apoE fragments to the full-length apoE were higher in AD patients than in controls with corresponding apoE genotypes (FIGS. 40A-C, $p<0.01$). In both groups, subjects with apoE4 had more apoE fragments than those without apoE4 (FIGS. 40A-C, $p<0.01$). These results suggest a relationship between apoE fragmentation and AD pathogenesis and that apoE4 is more susceptible than apoE3 to proteolytic cleavage in human brains.

Likewise, truncated fragments of apoE4 were found, in an age-dependent manner, in the brains of transgenic mice expressing human apoE4 in neurons. Importantly, the pattern of apoE fragmentation in NSE-apoE mice is similar to that in humans (compare FIGS. 41A and 41C). Moreover, transgenic mice with neuronal expression of apoE3 generated far fewer apoE fragments than the apoE4 mice (FIG. 41C), suggesting that apoE4 is more susceptible than apoE3 to proteolytic cleavage in mouse brains, as in human brains.

Figure 42:
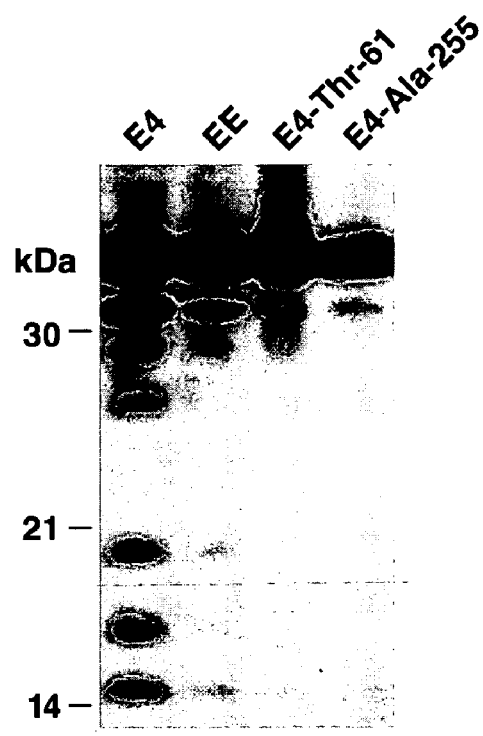
FIG. 42 depicts susceptibility of apoE4, apoE3, apoE4-Thr-61, and apoE4-Ala-255 to proteolysis.

To determine if domain interaction is responsible for the susceptibility of apoE4 to proteolysis, recombinant apoE4-Thr-61 or apoE4-Ala-255 (1 µg), both of which lack the intramolecular domain interaction, was incubated with partially purified AECE (10 µl) at 37° C. for 3 h. Anti-apoE western blotting showed that apoE4-Thr-61 and apoE4-Ala-255 were much more resistant to proteolysis than wildtype apoE4 (FIG. 42), suggesting that domain interaction is responsible for apoE4's susceptibility to proteolysis.

Figures 43A, 43B, 43C:
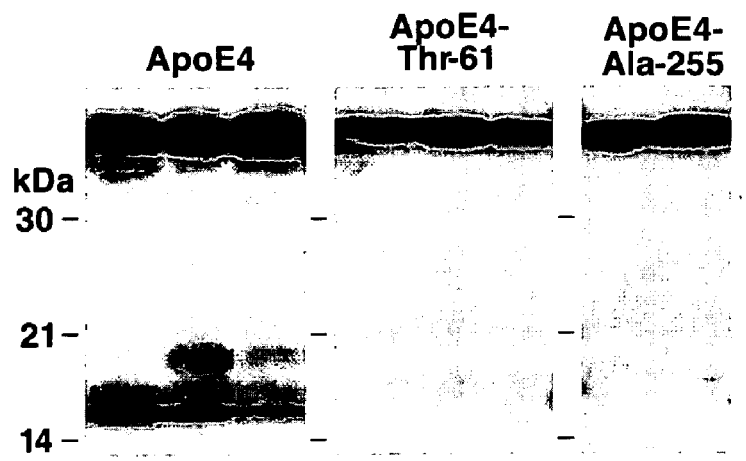
FIGS. 43A-C depict the susceptibility to proteolysis of apoE in brain lysates of wildtype apoE4 mice, apoE4-Thr-61 transgenic mice, and apoE4-Ala-255 transgenic mice.

To further prove the responsibility of domain interaction for apoE4's susceptibility to proteolysis, transgenic mice expressing apoE4-Thr-61 or apoE4-Ala-255 in CNS neurons were generated. Very strikingly, no apoE fragmentation was found in either apoE4-Thr-61 or apoE4-Ala-255 mouse brains (FIGS. 43B and 43C), whereas significant amounts of apoE fragments were found in wildtype apoE4 mouse brains at the same age (FIG. 43A). Since domain interaction is eliminated in both apoE4-Thr-61 and apoE4-Ala-255, these results strongly support the conclusion that apoE4 domain interaction is responsible for the susceptibility of apoE4 to proteolysis in vivo at least in transgenic mice.

FIGS. 40A-C. Isoform-specific fragmentation of apoE in human brains. Brain tissues from 19 AD patients (n=9 apoE3/3, ages 75±7; n=10 apoE4/3 and apoE4/4, ages 72±6) and 17 nondemented subjects (n=10 apoE3/3, age 72±6; n=7 apoE4/3, age 70±5) were collected 5-14 h after death, frozen immediately on dry ice, and stored at −80° C. until used. The tissue from the midfrontal gyrus (1-2 g) was homogenized with a Polytron homogenizer as described previously. The brain lysates (150 µg total proteins) were subjected to SDS-PAGE and analyzed with antibodies against full-length apoE (A) or carboxyl-terminal 28 amino acids of apoE (B). The ratios of the truncated apoEs (29 kDa and 14-20 kDa) to the full-length apoE were quantified by densitometry (C). w/o E4, subjects without apoE 4 (here only apoE3/3); w/E4, subjects with at least one apoE4 allele (apoE4/3 or apoE4/4).

FIGS. 41A-C. ApoE fragmentation in the brains of NSE-apoE or GFAP-apoE mice and humans. ApoE in brain lysates of NSE-apoE (A) or GFAP-apoE (B) mice or humans (C) as detected by western blotting with antibodies against full-length apoE or carboxyl-terminal apoE. Note that the apoE fragmentation occurs in NSE-apoE mouse brains (A), which is similar to that in human brains (C), but not in GFAβ-apoE mouse brains (B).

FIGS. 43A-C. ApoE4 domain interaction is necessary for the susceptibility of apoE4 to proteolysis in transgenic mice. ApoE in brain lysates of three wildtype apoE4 (A), three apoE4-Thr-61 (B), and two apoE4-Ala-255 (C) transgenic mice at the age of 2 months was detected by western blotting with antibodies against full-length apoE. ApoE fragmentation occurred in the brains of wildtype apoE4 transgenic mice but not in the brains of apoE4-Thr-61 or apoE4-Ala-255 transgenic mice.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. An apoE4 domain interaction inhibitor compound of Formula IV:

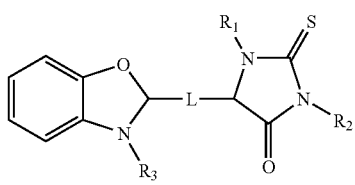

(IV)

wherein:
$R_1$ and $R_2$ are each independently —H or lower alkyl (e.g., $C_1$-$C_4$); with the proviso that at least one of $R_1$ and $R_2$ is alkylated;
$R_3$ is —$(CH_2)_n$—$SO_3$, or —$(CH_2)_n$—O—$SO_3$ wherein n=3-4; and
L is —$(CH_2)_m$, =CH—$(CH_2)_n$—CH=, —CH=CH—$(CH_2)$—, or —$(CH_2)$—CH=CH—, wherein m=0, or an integer from 1-3; and where n=1.

2. The apoE4 domain interaction inhibitor compound of claim 1, wherein $R_1$ and $R_2$ are each independently ethyl, methyl, propyl, or butyl.

3. The apoE4 domain interaction inhibitor compound of claim 1, wherein $R_3$ is —$(CH_2)_n$—$SO_3$, wherein n=3-4.

4. The apoE4 domain interaction inhibitor compound of claim 1, wherein L is =CH—$(CH_2)_n$—CH=, wherein n=1.

5. An apoE4 domain interaction inhibitor compound of Formula IV:

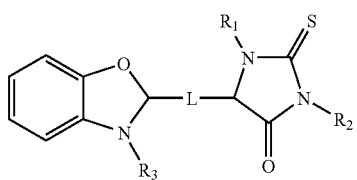

(IV)

wherein:
$R_1$ and $R_2$ are each independently —H or lower alkyl (e.g., $C_1$-$C_4$); with the proviso that at least one of $R_1$ and $R_2$ is alkylated;
$R_3$ is —$(CH_2)_n$—$SO_3$, or —$(CH_2)_n$—O—$SO_3$ wherein n=1-4; and
L is —$(CH_2)_m$, =CH—$(CH_2)_n$—CH=, —CH=CH—$(CH_2)$—, or —$(CH_2)$—CH=CH—, wherein m=0, or an integer from 1-3; and wherein n=1.

* * * * *

UNITED STATES PATENT AND TRADEMARK OFFICE
CERTIFICATE OF CORRECTION

| | | |
|---|---|---|
| PATENT NO. | : 7,964,598 B2 | Page 1 of 1 |
| APPLICATION NO. | : 11/244268 | |
| DATED | : June 21, 2011 | |
| INVENTOR(S) | : Robert W. Mahley et al. | |

It is certified that error appears in the above-identified patent and that said Letters Patent is hereby corrected as shown below:

Col. 1, line 20-23

Statement As To Federally Sponsored Research

"This invention was funded in part with funds from National Institutes of Health Program Project Grant HL41633. The U.S. Government has certain rights to this invention."

to read:

Col. 1, line 20-23

Statement As To Federally Sponsored Research

-- This invention was made with government support under Grant No. HL41633 awarded by National Institutes of Health. The U.S. government has certain rights in this invention. --

Signed and Sealed this
Twenty-seventh Day of September, 2011

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,964,598 B2 | Page 1 of 1 |
| APPLICATION NO. | : 11/244268 | |
| DATED | : June 21, 2011 | |
| INVENTOR(S) | : Mahley et al. | |

It is certified that error appears in the above-identified patent and that said Letters Patent is hereby corrected as shown below:

In the Specification

In Column 1, Lines 20-22, delete "This invention was funded in part with funds from National Institutes of Health Program Project Grant HL41633. The U.S. Government has certain rights to this invention." and insert --This invention was made with government support under HL041633 awarded by the National Institutes of Health. The government has certain rights in the invention.-- therefor Signed and Sealed this
Twenty-sixth Day of March, 2024

Katherine Kelly Vidal
*Director of the United States Patent and Trademark Office*